(12) United States Patent
Schrimpf et al.

(10) Patent No.: US 6,833,370 B1
(45) Date of Patent: Dec. 21, 2004

(54) HETEROCYCLE SUBSTITUTED AMINOAZACYCLES USEFUL AS CENTRAL NERVOUS SYSTEM AGENTS

(75) Inventors: Michael R. Schrimpf, Grayslake, IL (US); Kevin B. Sippy, Antioch, IL (US); Jerome F. Daanen, Racine, WI (US); Keith Brian Ryther, Round Lake Park, IL (US); Jianguo Ji, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/559,881

(22) Filed: Apr. 26, 2000

Related U.S. Application Data
(60) Provisional application No. 60/135,372, filed on May 21, 1999.

(51) Int. Cl.$^7$ .............. A61K 31/495; A61K 31/42; A61P 25/00; C07D 261/00; C07D 239/00
(52) U.S. Cl. .............. 514/255.05; 514/256; 514/274; 514/275; 514/301; 514/302; 514/313; 514/343; 514/372; 514/380; 544/316; 544/330; 544/332; 544/336; 544/406; 544/407; 544/408; 544/409; 546/114; 546/115; 546/116; 546/153; 546/155; 546/156; 546/162; 546/279.1; 548/213; 548/214; 548/244; 548/245; 548/246
(58) Field of Search .............. 548/213, 214, 548/244, 245, 246; 544/316, 330, 332, 336, 406, 407, 408, 409; 546/114, 115, 116, 153, 155, 156, 162, 279.1; 514/255.05, 256, 274, 275, 301, 302, 313, 343, 372, 380

(56) References Cited
U.S. PATENT DOCUMENTS

| | | | |
|---|---|---|---|
| 4,302,456 A | 11/1981 | Voorhees et al. | 424/251 |
| 4,409,228 A | 10/1983 | Nisato et al. | 424/267 |
| 4,592,866 A | 6/1986 | Cale, Jr. | 260/239.3 T |
| 4,705,853 A | 11/1987 | Cale, Jr. | 540/490 |
| 4,956,359 A | 9/1990 | Taylor, Jr. et al. | 514/210 |
| 5,037,841 A | 8/1991 | Schohe et al. | 514/373 |
| 5,157,035 A | 10/1992 | Stokbroekx et al. | 514/252 |
| 5,264,435 A | 11/1993 | Mizuchi et al. | 514/254 |
| 5,278,176 A | 1/1994 | Lin | 514/343 |
| 5,472,958 A | 12/1995 | Cunn, Jr. et al. | 514/210 |
| 5,604,245 A | 2/1997 | Le Fur et al. | 514/318 |
| 5,629,325 A | 5/1997 | Lin et al. | 514/318 |
| 5,670,656 A | 9/1997 | Cox et al. | 548/543 |
| 5,914,328 A | 6/1999 | Lin et al. | 514/252 |
| 5,948,793 A | 9/1999 | Abreo et al. | 514/318 |
| 5,985,878 A | 11/1999 | Stokbroekx et al. | 514/252 |

FOREIGN PATENT DOCUMENTS

| | | |
|---|---|---|
| EP | 0156433 | 2/1991 |
| EP | 0647639 | 4/1995 |
| EP | 0296560 | 2/1996 |
| WO | 9408922 | 4/1994 |
| WO | 9631475 | 10/1996 |

OTHER PUBLICATIONS

M. Williams et al., "Beyond the Tobacco Debate: Dissecting Out the Therapeutic Potential of Nicotine", Exp. Opin. Invest. Drugs 5, pp. 1035–1045 (1996).

Williams et al., J. Med. Chem., 42, pp. 1481–1500 (1999).

*Primary Examiner*—Brenda Coleman
(74) *Attorney, Agent, or Firm*—Portia Chen; Lawrence S. Pope

(57) ABSTRACT

Heterocyclic substituted aminoazacyclic compounds of formula I $$Z-R_3 \qquad \qquad I,$$

wherein Z is a defined aminoazacycle and $R_3$ is a defined heterocycle moiety, pharmaceutical compositions of these compounds, and use of said compositions to control synaptic transmission in mammals.

7 Claims, No Drawings

HETEROCYCLE SUBSTITUTED AMINOAZACYCLES USEFUL AS CENTRAL NERVOUS SYSTEM AGENTS

This application is a conversion of U.S. Provisional Application Ser. No. 60/135,372 filed on May 21, 1999.

TECHNICAL FIELD

The present invention is directed to a series of heterocyclic substituted aminoazacycles, a method for selectively controlling neurotransmitter release in mammals using these compounds, and pharmaceutical compositions including those compounds.

BACKGROUND OF INVENTION

Compounds that selectively control chemical synaptic transmission offer therapeutic utility in treating disorders that are associated with dysfunctions in synaptic transmission. This utility may arise from controlling either pre-synaptic or post-synaptic chemical transmission. The control of synaptic chemical transmission is, in turn, a direct result of a modulation of the excitability of the synaptic membrane. Presynaptic control of membrane excitability results from the direct effect an active compound has upon the organelles and enzymes present in the nerve terminal for synthesizing, storing, and releasing the neurotransmitter, as well as the process for active re-uptake. Postsynaptic control of membrane excitability results from the influence an active compound has upon the cytoplasmic organelles that respond to neurotransmitter action.

An explanation of the processes involved in chemical synaptic transmission will help to illustrate more fully the potential applications of the invention. (For a filler explanation of chemical synaptic transmission refer to Hoffman et al., "Neuro-transmission: The autonomic and somatic motor nervous systems." In: Goodman and Gilman's, The Pharmacological Basis of Therapeutics, 9th ed., J. G. Hardman, L. E. Limbird, P. B. Molinoff, R. W. Ruddon, and A. Goodman Gilman, eds., Pergamon Press, New York, (1996), pp. 105–139).

Typically, chemical synaptic transmission begins with a stimulus that depolarizes the transmembrane potential of the synaptic junction above the threshold that elicits an all-or-none action potential in a nerve axon. The action potential propagates to the nerve terminal where ion fluxes activate a mobilization process leading to neurotransmitter secretion and "transmission" to the postsynaptic cell. Those cells which receive communication from the central and peripheral nervous systems in the form of neurotransmitters are referred to as "excitable cells." Excitable cells are cells such as nerves, smooth muscle cells, cardiac cells and glands. The effect of a neurotransmitter upon an excitable cell may be to cause either an excitatory or an inhibitory postsynaptic potential (EPSP or IPSP, respectively) depending upon the nature of the postsynaptic receptor for the particular neurotransmitter and the extent to which other neurotransmitters are present. Whether a particular neurotransmitter causes excitation or inhibition depends principally on the ionic channels that are opened in the postsynaptic membrane (i.e., in the excitable cell).

EPSPs typically result from a local depolarization of the membrane due to a generalized increased permeability to cations (notably $Na^+$ and $K^+$), whereas IPSPs are the result of stabilization or hyperpolarization of the membrane excitability due to a increase in permeability to primarily smaller ions (including $K^+$ and $Cl^+$). For example, the neurotransmitter acetylcholine excites at skeletal muscle junctions by opening permeability channels for $Na^+$ and $K^+$. At other synapses, such as cardiac cells, acetylcholine can be inhibitory, primarily resulting from an increase in $K^+$ conductance.

The biological effects of the compounds of the present invention result from modulation of a particular subtype of acetylcholine receptor. It is, therefore, important to understand the differences between two receptor subtypes. The two distinct subfamilies of acetylcholine receptors are defined as nicotinic acetylcholine receptors and muscarinic acetylcholine receptors. (See Goodman and Gilman's, The Pharmacological Basis of Therapeutics, op. cit.).

The responses of these receptor subtypes are mediated by two entirely different classes of second messenger systems. When the nicotinic acetylcholine receptor is activated, the response is an increased flux of specific extracellular ions (e.g. $Na^+$, $K^+$ and $Ca^{++}$) through the neuronal membrane. In contrast, muscarinic acetylcholine receptor activation leads to changes in intracellular systems that contain complex molecules such as G-proteins and inositol phosphates. Thus, the biological consequences of nicotinic acetylcholine receptor activation are distinct from those of muscarinic receptor activation. In an analogous manner, inhibition of nicotinic acetylcholine receptors results in still other biological effects, which are distinct and different from those arising from muscarinic receptor inhibition.

As indicated above, the two principal sites to which drug compounds that affect chemical synaptic transmission may be directed are the presynaptic membrane and the postsynaptic membrane. Actions of drugs directed to the presynaptic site may be mediated through presynaptic receptors that respond to the neurotransmitter which the same secreting structure has released (i.e., through an autoreceptor), or through a presynaptic receptor that responds to another neurotransmitter (i.e., through a heteroreceptor). Actions of drugs directed to the postsynaptic membrane mimic the action of the endogenous neurotransmitter or inhibit the interaction of the endogenous neurotransmitter with a postsynaptic receptor.

Classic examples of drugs that modulate postsynaptic membrane excitability are the neuromuscular blocking agents which interact with nicotinic acetylcholine-gated channel receptors on skeletal muscle, for example, competitive (stabilizing) agents, such as curare, or depolarizing agents, such as succinylcholine.

In the central nervous system (CNS), postsynaptic cells can have many neurotransmitters impinging upon them. This makes it difficult to know the precise net balance of chemical synaptic transmission required to control a given cell. Nonetheless, by designing compounds that selectively affect only one pre- or postsynaptic receptor, it is possible to modulate the net balance of all the other inputs. Obviously, the more that is understood about chemical synaptic transmission in CNS disorders, the easier it would be to design drugs to treat such disorders.

Knowing how specific neurotransmitters act in the CNS allows one to predict the disorders that may be treatable with certain CNS active drugs. For example, dopamine is widely recognized as an important neurotransmitter in the central nervous systems in humans and animals. Many aspects of the pharmacology of dopamine have been reviewed by Roth and Elsworth, "Biochemical Pharmacology of Midbrain Dopamine Neurons", In: Psychopharmacology: The Fourth Generation of Progress, F. E. Bloom and D. J. Kupfer, Eds., Raven Press, NY, 1995, pp 227–243). Patients with Parkinson's disease have a primary loss of dopamine containing neurons of the nigrostriatal pathway, which results in profound loss of motor control. Therapeutic strategies to replace the dopamine deficiency with dopamine mimetics, as well as administering pharmacologic agents that modify dopamine release and other neurotransmitters have been found to have therapeutic benefit ("Parkinson's Disease", In: Psychopharmacology: The Fourth Generation of Progress, op. cit., pp 1479–1484).

New and selective neurotransmitter controlling agents are still being sought, in the hope that one or more will be useful in important, but as yet poorly controlled, disease states or behavior models. For example, dementia, such as is seen with Alzheimer's disease or Parkinsonism, remains largely untreatable. Symptoms of chronic alcoholism and nicotine withdrawal involve aspects of the central nervous system, as does the behavioral disorder Attention Deficit Hyperactivity Disorder (ADHD). Specific agents for treatment of these and related disorders are few in number or nonexistent.

A more complete discussion of the possible utility as CNS active agents of compounds with activity as cholinergic ligands selective for neuronal nicotinic receptors, (i.e., for controlling chemical synaptic transmission) may be found in U.S. Pat. No. 5,472,958, to Gunn et al., issued Dec. 5, 1995, the disclosure of is incorporated herein by reference.

Existing acetylcholine agonists are therapeutically suboptimal in treating the conditions discussed above. For example, such compounds have unfavorable pharmacokinetics (e.g., arecoline and nicotine), poor potency and lack of selectivity (e.g., nicotine), poor CNS penetration (e.g., carbachol) or poor oral bioavailability (egg., nicotine). In addition, other agents have many unwanted central agonist actions, including hypothermia, hypolocomotion and tremor and peripheral side effects, including miosis, lachrymation, defecation and tachycardia (Benowitz et al., in: Nicotine Psychopharmacology, S. Wonnacott, M. A. H. Russell, & I. P. Stolerman, eds., Oxford University Press, Oxford, 1990, pp. 112–157; and M. Davidson, et al., in Current Research in Alzheimer Therapy, E. Giacobini and R. Becker, ed.; Taylor & Francis: New York, 1988; pp 333–336).

Williams et al. reports the use of cholinergic channel modulators to treat Parkinson's and Alzheimer's Diseases (M. Williams et al., "Beyond the Tobacco Debate: Dissecting Out the Therapeutic Potential of Nicotine", Exp. Opin. Invest. Drugs 5, pp. 1035–1045 (1996). Salin-Pascual et al. reports short-term improvement of nonsmoking patients suffering from depression by treatment with nicotine patches (R. J. Salin-Pascual et al., "Antidepressant Effect of Transdermal Nicotine Patches in Non-Smoking Patients with Major Depression", J. Clin. Psychiatry, v. 57 pp. 387–389 (1996).

Various 2-pyridines substituted with a 4-aminopiperidine have been disclose by (U.S. Pat. No. 5,604,245) as serotoninergic agonists. Certain pyridazines substituted with an azacycle have been disclosed by (EP 156433B1) as anti-viral agents. Azacyclic pyridazines of the present invention are distinct in that the azacycle is substituted with an alkylamino or dialkylamino substituent. Pyrrolidine and azetidine azacycles substituted at the 3-position have been disclosed (cf U.S. Pat. No. 4,592,866 to A. D. Cale; U.S. Pat. No. 4,705,853 to A. D. Cale; U.S. Pat. No. 4,956,359 to Taylor et al.; and U.S. Pat. No. 5,037,841 to Schoehe et al. and European patent application EP296560A2, to Sugimoto et al.).

Certain nicotine related compounds having utility in enhancing cognitive function have been reported by Lin in U.S. Pat. No. 5,278,176, issued Jan. 11, 1994. Also, 2-(nitrophenoxymethyl)heterocyclic compounds with similar function have been reported by Gunn et al., U.S. Pat. No. 5,472,958, issued Dec. 5, 1995.

Certain (pyrid-3-yloxymethyl)heterocyclic compounds useful in controlling chemical synaptic transmission have been described by Lin et al. in U.S. Pat. No. 5,629,325, issued May 13, 1997.

WO 94/08922 describes pyridyl ether compounds which enhance cognitive function. U.S. patent application Ser. Nos. 08/474,873 and 08/485,537 describe certain substituted pyridyl ether compounds as well as other compounds which also act at the nicotinic acetylcholine receptor to stimulate or inhibit neurotransmitter release. WO 96/31475 describes certain 3-substituted pyridine derivatives which are described as being useful for a variety of disorders as modulators of acetylcholine receptors. While some of these references have alluded to pain control as a potential use of the compounds or analogs recited therein, the Applicants have discovered that compounds of formula I shown below have a surprising and unexpected analgesic effect.

In addition, cholinergic channel modulators may be useful in treating pain. The search for more potent and more effective pain controllers or analgesics continues to be a significant research goal in the medical community. A substantial number of medical disorders and conditions produce pain as part of the disorder or condition. Relief of this pain is a major aspect of ameliorating or treating the overall disease or condition. Pain and the possible allievation thereof is also attributable to the individual patient's mental condition and physical condition. One pain reliever, or a class, may not be effective for a particular patient, or group of patients, which leads to a need for finding additional compounds or pharmaceuticals which are effective analgesics. Opioid and non-opioid drugs are the two major classes of analgesics (Dray, A. and Urban, L., Ann. Rev. Pharmacol. Toxicol., 36: 253–280, 1996). Opioids, such as morphine, act at opioid receptors in the brain to block transmission of the pain signals in the brain and spinal cord (Cherney, N. I., Drug, 51:713–737, 1996). Opioids such as morphine have abuse and addiction liability. Non-opioids such as non-steroid anti-inflammatory agents (NSAIDs) typically, but not exclusively, block the production of prostaglandins to prevent sensitization of nerve endings that facilitate the pain signal to the brain (Dray, et al, Trends in Pharmacol. Sci., 15: 190–197, 1994; Carty, T. J. and Marfat, A., "COX-2 Inhibitors. Potential for reducing NSAID side-effects in treating inflammatory diseases", In: Emerging Drugs: Prospect for Improved Medicines. (W. C. Bowman, J. D. Fitzgerald, and J. B. Taylor, eds.), Ashley Publications Ltd., London, Chap. 19., pp. 391411). Most of the commonly prescribed over-the-counter (OTC) NSAIDs are also commonly associated with at least one side effect or another, such as stomach ulceration or pain. For example, NSAIDs such as aspirin are also known to cause irritation and ulceration of the stomach and duodenum.

Certain compounds, with primary therapeutic indications other than analgesia, have been shown to be effective in some types of pain control. These are classified as analgesic adjuvants, and include tricyclic antidepressants (TCAs) and some anticonvulsants such as gabapentin (Williams et al., J. Med. Chem. (1999), 42, 1481–1500). The exact mechanism of action of these drugs is not fully understood, but they are used increasingly for treatment, especially for pain resulting from nerve injury due to trauma, radiation, or disease.

The compounds of the present invention are novel and may have utility in treating disorders and medical conditions listed herein. The compounds of the present invention may also have utility when administered in combination with an opioid such as morphine, or a non-steroid anti-inflammatory agent such as aspirin, or a tricyclic antidepressant, or an anticonvulsant such as gabapentin or pregabalin for treating disorders and medical conditions listed herein.

SUMMARY OF THE INVENTION

The present invention discloses heterocyclic substituted aminoazacyclic compounds, a method for selectively controlling neurotransmitter release in mammals using these compounds, and pharmaceutical compositions including those compounds. More particularly, the present invention is directed to compounds of formula I

Z—R$_3$     I, or pharmaceutically acceptable salts and prodrugs thereof wherein, Z is selected from the group consisting of

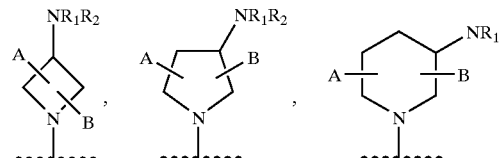

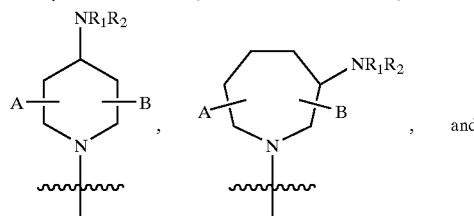

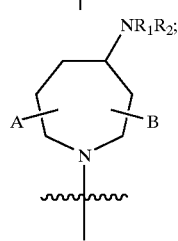

R$_1$ and R$_2$ are independently selected from the group consisting of hydrogen and alkyl;

A and B are independently absent or independently selected from the group consisting of alkenyl, alkoxy, alkoxycarbonyl, alkyl, alkynyl, carboxy, haloalkyl, halogen, hydroxy, and hydroxyalkyl;

R$_3$ is selected from the group consisting of

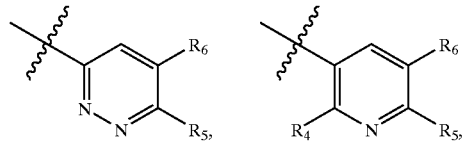

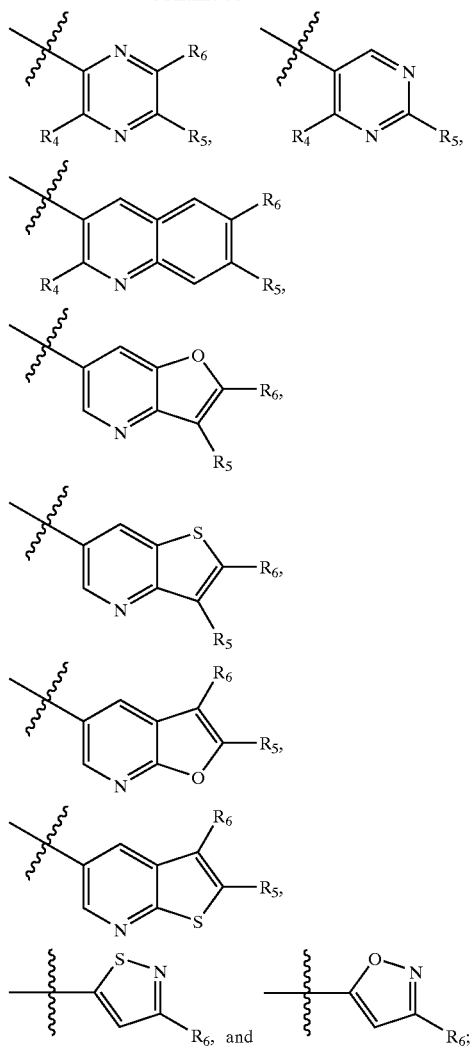

R$_4$ is selected from the group consisting of hydrogen, alkyl, and halogen;

R$_5$ is selected from the group consisting of hydrogen, alkoxy, alkyl, halogen, nitro, and —NR$_{10}$R$_{11}$ wherein R$_{10}$ and R$_{11}$ are independently selected from the group consisting of hydrogen and lower alkyl;

R$_6$ is selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, amino, aminoalkyl, aminocarbonyl, aminocarbonylalkyl, aminosulfonyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, 5-tetrazolyl, —NR$_7$SO$_2$R$_8$, —C(NR$_7$)NR$_8$R$_9$, —CH$_2$C(NR$_7$)NR$_8$R$_9$, —C(NOR$_7$)R$_8$, —C(NCN)R$_7$, —C(NNR$_7$R$_8$)R$_9$, —S(O)$_2$OR$_7$, and —S(O)$_2$R$_7$; and R$_7$, R$_8$, and R$_9$ are independently selected from the group consisting of hydrogen and alkyl;

provided that when R$_3$ is pyridazine then R$_1$ is alkyl.

DETAILED DESCRIPTION OF THE INVENTION

In one embodiment of the present invention are disclosed compounds of formula II

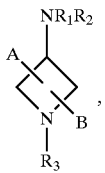

or pharmaceutically acceptable salts thereof wherein A, B, $R_1$, $R_2$, and $R_3$ are as defined in formula I.

In another embodiment are disclosed compounds of formula II wherein A is as defined in formula I; B is absent; $R_1$ and $R_2$ are independently selected from hydrogen and lower alkyl wherein hydrogen and methyl are preferred; $R_3$ is

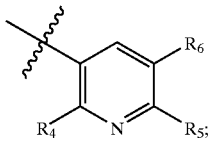

$R_4$ is hydrogen; $R_5$ is selected from hydrogen, halogen, and lower alkyl; and $R_6$ is selected from hydrogen, cyano, haloalkoxy, haloalkyl, halogen, hydroxy, lower alkoxy, lower alkyl, lower alkynyl, and nitro.

A representative compound of formula II includes, but is not limited to:
1-(6-chloro-3-pyridinyl)-3-azetidinylamine.

In another embodiment of the present invention are disclosed compounds of formula III

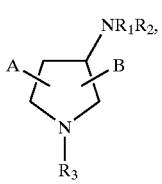

or pharmaceutically acceptable salts thereof wherein A, B, $R_1$, $R_2$, and $R_3$ are as defined in formula I.

In another embodiment are disclosed compounds of formula III wherein A is as defined in formula I; B is absent; $R_1$ and $R_2$ are independently selected from hydrogen and lower alkyl wherein hydrogen and methyl are preferred; $R_3$ is

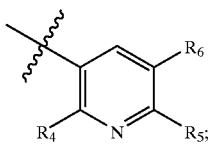

$R_4$ is hydrogen; $R_5$ is selected from hydrogen, halogen, and lower alkyl; and $R_6$ is selected from hydrogen, cyano, haloalkoxy, haloalkyl, halogen, hydroxy, lower alkoxy, lower alkyl, lower alkynyl, and nitro.

Representative compounds of formula III include, but are not limited to:
N-[(3S)-1-(6-chloro-3-pyridinyl)pyrrolidinyl]-N-methylamine;
(3S)-1-(6-chloro-3-pyridinyl)pyrrolidinylamine;
N-[(3S)-1-(6-chloro-3-pyridinyl)pyrrolidinyl]-N,N-dimethylamine;
(3R)-1-(6-chloro-3-pyridinyl)pyrrolidinylamine;
N-[(3R)-1-(6-chloro-3-pyridinyl)pyrrolidinyl]-N-methylamine;
N-[(3R)-1-(6-chloro-3-pyridinyl)pyrrolidinyl]-N,N-dimethylamine;
1-(6-chloro-3-pyridinyl)-3-pyrrolidinylamine;
(3S)-1-(3-pyridinyl)pyrrolidinylamine;
N-methyl-N-[(3S)-1-(3-pyridinyl)pyrrolidinyl]amine;
1-(3-pyridinyl)-3-pyrrolidinylamine;
(3R)-1-[5-(trifluoromethyl)-3-pyridinyl]pyrrolidinylamine;
N-methyl-N-{(3R) 1-[5-(trifluoromethyl)-3-pyridinyl]pyrrolidinyl}amine;
(3S)-1-[5-(trifluoromethyl)-3-pyridinyl]pyrrolidinylamine;
N-methyl-N-{(3S)-1-[5-(tri fluoromethyl)-3-pyridinyl]pyrrolidinyl} amine;
(3R)-1-(6-chloro-5-chloro-5-methyl-3-pyridinyl) pyrrolidinyl amine;
N-[(3R)-1-(6-chloro-5-methyl-3-pyridinyl)pyrrolidinyl]-N-methylamine;
(3S)-1-(6-chloro-5-methyl-3-pyridinyl)pyrrolidinylamine;
N-[(3S)-1-(6-chloro-5-methyl-3-pyridinyl)pyrrolidinyl]-N-methylamine;
(3S)-1-(5,6-dichloro-3-pyridinyl)pyrrolidinylamine;
N-[(3S)-1-(5,6-dichloro-3-pyridinyl)pyrrolidinyl]-N-methylamine;
(3R)-1-(5,6-dichloro-3-pyridinyl)pyrrolidinylamine;
N-[(3R)-1-(5,6-dichloro-3-pyridinyl)pyrrolidinyl]-N-methylamine;
(3S)-1-(6-chloro-5-methoxy-3-pyridinyl)pyrrolidinylamine;
N-[(3S)-1-(6-chloro-5-methoxy-3-pyridinyl)pyrrolidinyl]-N-methylamine;
(3S)-1-(6-fluoro-5-methyl-3-pyridinyl)pyrrolidinylamine;
N-[(3S)-1-(6-fluoro-5-methyl-3-pyridinyl) pyrrolidinylamine;
N-[(3S)-1-(6-fluoro-5-methyl-3-pyridinyl)pyrrolidinyl]-N-methylamine;
(3R)-1-(6-fluoro-5-methyl-3-pyridinyl)pyrrolidinylamine;
N-[(3R)-1-(6-fluoro-5-methyl-3-pyridinyl)pyrrolidinyl]-N-methylamine;
(3S)-1-(5-nitro-3-pyridinyl) pyrrolidinylamine;
N-methyl-N-[(3S)-1-(5-nitro-3-pyridinyl)pyrrolidinyl] amine;
(3R)-1-(5-nitro-3-pyridinyl)pyrrolidinylamine;
N-methyl-N-[(3R)-1-(5-nitro-3-pyridinyl)pyrrolidinyl] amine; and
(2S,3R)-2-(chloromethyl) 1-(3-pyridinyl)pyrrolidinylamine.

The following additional compounds, representative of formula III, may be prepared by one skilled in the art using known synthetic chemistry methodology or by using synthetic chemistry methodology described in the Schemes and Examples contained herein.
(3R)-1-(3-pyridinyl)pyrrolidinylamine;
N-methyl-N-[(3R)-1-(3-pyridinyl)pyrrolidinyl]amine;
(3R)-1-(6-chloro-5-methoxy-3-pyridinyl) pyrrolidinylamine;
N-[(3R)-1-(6-chloro-5-methoxy-3-pyridinyl)pyrrolidinyl]-N-methylamine;
(3S)-1-(5-methoxy-3-pyridinyl)pyrrolidinylamine;
N-[(3S)-1-(5-methoxy-3-pyridinyl)pyrrolidinyl]-N-methylamine;

(3R)-1-(5-methoxy-3-pyridinyl)pyrrolidinylamine;
N-[(3R)-1-(5-methoxy-3-pyridinyl)pyrrolidinyl]-N-methylamine;
(3S)-1-(6-bromo-3-pyridinyl)pyrrolidinylamine;
N-[(3S)-1-(6-bromo-3-pyridinyl)pyrrolidinyl]-N-methylamine;
(3R)-1-(6-bromo-3-pyridinyl)pyrrolidinylamine;
N-[(3R)-1-(6-bromo-3-pyridinyl)pyrrolidinyl]-N-methylamine;
(3S)-1-(5-fluoro-3-pyridinyl)pyrrolidinylamine;
N-[(3S)-1-(5-fluoro-3-pyridinyl)pyrrolidinyl]-N-methylamine;
(3Rd 1-(5-fluoro-3-pyridinyl)pyrrolidinylamine;
N-[(3R)-1-(5-fluoro-3-pyridinyl)pyrrolidinyl]-N-methylamine;
(3S)-1-(6-chloro-5-fluoro-3-pyridinyl)pyrrolidinylamine;
N-[(3S)-1-(6-chloro-5-fluoro-3-pyridinyl)pyrrolidinyl]-N-methylamine;
(3R)-1-(6-chloro-5-fluoro-3-pyridinyl)pyrrolidinylamine;
N-[(3R)-1-(chloro-5-fluoro-3-pyridinyl)pyrrolidinyl]-N-methylamine;
(3S)-1-(6-bromo-5-fluoro-3-pyridinyl)pyrrolidinylamine;
N-[(3S)-1-(6-bromo-5-fluoro-3-pyridinyl)pyrrolidinyl]-N-methylamine;
(3R)-1-(6-bromo-5-fluoro-3-pyridinyl)pyrrolidinylamine;
N-[(3R)-1-(6-bromo-5-fluoro-3-pyridinyl)pyrrolidinyl-N-methylamine;
(3S)-1-(5-bromo-6-chloro-3-pyridinyl)pyrrolidinylamine;
N-[(3S)-1-(5-bromo-6-chloro-3-pyridinyl)pyrrolidinyl]-N-methylamine;
(3R)-1-(5-bromo-6-chloro-3-pyridinyl)pyrrolidinylamine;
N-[(3R)-1-(5-bromo-6-chloro-3-pyridinyl)pyrrolidinyl]-N-methylamine;
(3S)-1-(6-bromo-5-chloro-3-pyridinyl)pyrrolidinylamine;
N-[(3S)-1-(6-bromo-5-chloro-3-pyridinyl)pyrrolidinyl]-N-methylamine;
(3R)-1-(6-bromo-5-chloro-3-pyridinyl)pyrrolidinylamine;
N-[(3R)-1-(6-bromo-5-chloro-3-pyridinyl)pyrrolidinyl]-N-methylamine;
(3S)-1-(6-bromo-5-ethoxy-3-pyridinyl)pyrrolidinylamine;
N-[(3S)-1-(6-bromo-5-ethoxy-3-pyridinyl)pyrrolidinyl]-N-methylamine;
(3R)-1-(6-bromo-5-ethoxy-3-pyridinyl)pyrrolidinylamine;
N-[(3R)-1-(6-bromo-5-ethoxy-3-pyridinyl)pyrrolidinyl]-N-methylamine;
(3S)-1-(5-cyano-3-pyridinyl)pyrrolidinylamine;
N-[(3S)-1-(5-cyano-3-pyridinyl)pyrrolidinyl]-N-methylamine;
(3R)-1-(5-cyano-3-pyridinyl)pyrrolidinylamine;
N-[(3R)-1-(5-cyano-3-pyridinyl)pyrrolidinyl]-N-methylamine;
(3S)-1-(5-ethynyl-3-pyridinyl)pyrrolidinylamine;
N-[(3S)-1-(5-ethynyl-3-pyridinyl)pyrrolidinyl]-N-methylamine;
(3R)-1-(5-ethynyl-3-pyridinyl)pyrrolidinylamine;
N-[(3R)-1-(5-ethynyl-3-pyridinyl)pyrrolidinyl]-N-methylamine;
(3S)-1-furo[3,2-b]pyridin-6-ylpyrrolidinylamine;
N-[(3S)-1-furo[3,2-b]pyridin-6-ylpyrrolidinyl]-N-methylamine;
(3R)-1-furo[3,2-b]pyridin-6-ylpyrrolidinylamine;
N-[(3R)-1-furo[3,2-b]pyridin-6-ylpyrrolidinyl]-N-methylamine;
1-(6-chloro-3-pyridinyl)-3-methyl-3-pyrrolidinylamine;
N-[1-(6-chloro-3-pyridinyl)-3-methyl-3-pyrrolidinyl]-N-methylamine;
1-(3-pyridinyl)-3-methyl-3-pyrrolidinylamine; and
N-[1-(3-pyridinyl)-3-methyl-3-pyrrolidinyl]-N-methylamine.

In another embodiment of the present invention are disclosed compounds of formula

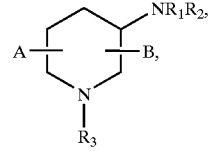

IV or pharmaceutically acceptable salts thereof wherein A, B, $R_1$, $R_2$, and $R_3$ are as defined in formula I.

In another embodiment are disclosed compounds of formula IV wherein A is as defined in formula I; B is absent; $R_1$ and $R_2$ are independently selected from hydrogen and lower alkyl wherein hydrogen and methyl are preferred; $R_3$ is

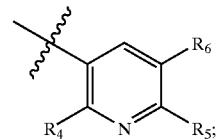

$R_4$ is hydrogen; $R_5$ is selected from hydrogen, halogen, and lower alkyl; and $R_6$ is selected from hydrogen, cyano, haloalkoxy, haloalkyl, halogen, hydroxy, lower alkoxy, lower alkyl, lower alkynyl, and nitro.

Representative compounds of formula IV include, but are not limited to:
1-(6-chloro-3-pyridinyl)-3-piperidinylamine;
(3R,4R)-1-(6-chloro-3-pyridinyl)-4-methylpiperidinylamine;
(3R,4S)-1-(6-chloro-3-pyridinyl)-4-methylpiperidinylamine;
(3S)-1-(3-pyridinyl)piperidinylamine;
N-methyl-N-[(3S)-1-(3-pyridinyl)piperidinyl]amine;
(3R)-1-(3-pyridinyl)piperidinylamine;
N-methyl-N-[(3R)-1-(3-pyridinyl)piperidinyl]amine;
(3S)-1-(6-chloro-3-pyridinyl)piperidinylamine;
N-[(3S)-1-(6-chloro-3-pyridinyl)piperidinyl]-N-methylamine;
(3R)-1-(6-chloro-3-pyridinyl)piperidinylamine;
N-(3R)-1-(6-chloro-3-pyridinyl)piperidinyl]-N-methylamine; and
N-[(3S)-1-(6-chloro-5-methyl-3-pyridinyl)piperidinyl]-N-methylamine.

The following additional compounds, representative of formula IV, may be prepared by one skilled in the art using known synthetic chemistry methodology or by using synthetic chemistry methodology described in the Schemes and Examples contained herein.
(3S)-1-(5,6-dichloro-3-pyridinyl)piperidinylamine;
N-[(3S)-1-(5,6-dichloro-3-pyridinyl)piperidinyl]-N-methylamine;
(3R)-1-(5,6-dichloro-3-pyridinyl)piperidinylamine;
N-[(3R)-1-(5,6-dichloro-3-pyridinyl)piperidinyl]-N-methylamine;
(3S)-1-(6-chloro-5-methoxy-3-pyridinyl)piperidinylamine;
N-[(3S)-1-(6-chloro-5-methoxy-3-pyridinyl)piperidinyl]-N-methylamine;
(3R)-1-(6-chloro-5-methoxy-3-pyridinyl)piperidinylamine;
N-[(3R)-1-(6-chloro-5-methoxy-3-pyridinyl)piperidinyl]-N-methylamine;

(3S)-1-(6-chloro-5-methyl-3-pyridinyl)piperidinylamine;
(3R)-1-(6-chloro-5-methyl-3-pyridinyl)piperidinylamine;
N-[(3R)-1-(6-chloro-5-methyl-3-pyridinyl)piperidinyl]-N-methylamine;
(3S)-1-(5-methoxy-3-pyridinyl)piperidinylamine;
N-[(3R)-1-(5-methoxy-3-pyridinyl)piperidinyl]-N-methylamine;
(3R)-1-(5-methoxy-3-pyridinyl)piperidinylamine;
N-[(3R)-1-(5-methoxy-3-pyridinyl)piperidinyl]-N-methylamine;
(3S)-1-(6-bromo-3-pyridinyl)piperidinylamine;
N-[(3S)-1-(6-bromo-3-pyridinyl)piperidinyl]-N-methylamine;
(3R)-1-(6-bromo-3-pyridinyl)piperidinylamine;
N-[(3R)-1-(6-bromo-3-pyridinyl)piperidinyl]-N-methylamine;
(3R)-1-(5-fluoro-3-pyridinyl)piperidinylamine;
N-[(3R)-1-(5-fluoro-3-pyridinyl)piperidinyl]-N-methylamine;
(3R)-1-(5-fluoro-3-pyridinyl)piperidinylamine;
N-[(3R)-1-(5-fluoro-3-pyridinyl)piperidinyl]-N-methylamine;
(3R)-1-(6-chloro-5-fluoro-3-pyridinyl)piperidinylamine;
N-[(3S)-1-(6-chloro-5-fluoro-3-pyridinyl)piperidinyl]-N-methylamine;
(3R)-1-(6-chloro-5-fluoro-3-pyridinyl)piperidinylamine;
N-[(3R)-1-(6-chloro-5-fluoro-3-pyridinyl)piperidinyl]-N-methylamine;
(3S)-1-(6-bromo-5-fluoro-3-pyridinyl)piperidinylamine;
N-[(3S)-1-(6-bromo-5-fluoro-3-pyridinyl)piperidinyl]-N-methylamine;
(3R)-1-(6-bromo-5-fluoro-3-pyridinyl)piperidinylamine;
N-[(3R)-1-(6-bromo-5-fluoro-3-pyridinyl)piperidinyl]-N-methylamine;
(3S)-1-(6-bromo-6-chloro-3-pyridinyl)piperidinylamine;
N-[(3S)-1-(5-bromo-6-chloro-3-pyridinyl)piperidinyl]-N-methylamine;
(3R)-1-(5-bromo-6-chloro-3-pyridinyl)piperidinylamine;
N-[(3R)-1-(5-bromo-6-chloro-3-pyridinyl)piperidinyl]-N-methylamine;
(3S)-1-(6-bromo-5-chloro-3-pyridinyl)piperidinylamine;
N-[(3S)-1-(6-bromo-5-chloro-3-pyridinyl)piperidinyl]-N-methylamine;
(3R)-1-(6-bromo-5-chloro-3-pyridinyl)piperidinylamine;
N-[(3R)-1-(6-bromo-5-chloro-3-pyridinyl)piperidinyl]-N-methylamine;
(3S)-1-(6-bromo-5-ethoxy-3-pyridinyl)piperidinylamine;
N-[(3S)-1-(6-bromo-5-ethoxy-3-pyridinyl)piperidinyl]-N-methylamine;
(3R)-1-(6-bromo-5-ethoxy-3-pyridinyl)piperidinylamine;
N-[(3R)-1-(6-bromo-5-ethoxy-3-pyridinyl)piperidinyl]-N-methylamine;
(3S)-1-(5-cyano-3-pyridinyl)piperidinylamine;
N-[(3S)-1-(5-cyano-3-pyridinyl)piperidinyl]-N-methylamine;
(3R)-1-(5-cyano-3-pyridinyl)piperidinylamine;
N-[(3R)-1-(5-cyano-3-pyridinyl)piperidinyl]-N-methylamine;
(3S)-1-(5-ethynyl-3-pyridinyl)piperidinylamine;
N-[(3S)-1-(5-ethynyl-3-pyridinyl)piperidinyl]-N-methylamine;
(3R)-1-(5-ethynyl-3-pyridinyl)piperidinylamine;
N-[(3R)-1-(5-ethynyl-3-pyridinyl)piperidinyl]-N-methylamine;
(3S)-1-furo[3,2-b]pyridin-6-ylpiperidinylamine;
N-[(3S)-1-furo[3,2-b]pyridin-6-ylpiperidinyl]-N-methylamine;
(3R)-1-furo[3,2-b]pyridin-6-ylpiperidinylamine; and
N-[(3R)-1-furo[3,2-b]pyridin-6-ylpiperidinyl]-N-methylamine.

In another embodiment of the present invention are disclosed compounds of formula V

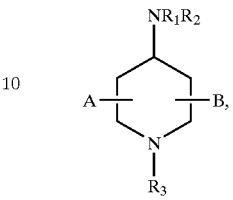

or pharmaceutically acceptable salts thereof wherein A, B, $R_1$, $R_2$, and $R_3$ are as defined in formula I.

In another embodiment are disclosed compounds of formula V wherein A is as defined in formula I; B is absent; $R_1$ and $R_2$ are independently selected from hydrogen and lower alkyl wherein hydrogen and methyl are preferred; $R_3$ is

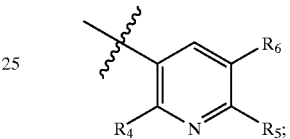

$R_4$ is hydrogen; $R_5$ is selected from hydrogen, halogen, and lower alkyl; and $R_6$ is selected from hydrogen, cyano, haloalkoxy, haloalkyl, halogen, hydroxy, lower alkoxy, lower alkyl, lower alkynyl, and nitro.

A representative compound of formula V includes, but is not limited to:
1-(6-chloro-3-pyridinyl)-4-piperidinylamine.

In another embodiment of the present invention are disclosed compounds of formula VI

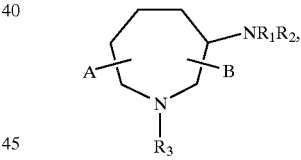

or pharmaceutically acceptable salts thereof wherein A, B, $R_1$, $R_2$, and $R_3$ are as defined in formula I.

In another embodiment are disclosed compounds of formula VI wherein A is as defined in formula I; B is absent; $R_1$ and $R_2$ are independently selected from hydrogen and lower alkyl wherein hydrogen and methyl are preferred; $R_3$ is

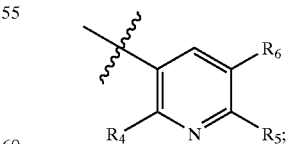

$R_4$ is hydrogen; $R_5$ is selected from hydrogen, halogen, and lower alkyl; and $R_6$ is selected from hydrogen, cyano, haloalkoxy, haloalkyl, halogen, hydroxy, lower alkoxy, lower alkyl, lower alkynyl, and nitro.

The following additional compounds, representative of formula VI, may be prepared by one skilled in the art using known synthetic chemistry methodology or by using synthetic chemistry methodology described in the Schemes and Examples contained herein.

(3S)-1-(3-pyridinyl)azepanylamine;
N-methyl-N-[(3S)-1-(3-pyridinyl)azepanyl]amine;
(3R)-1-(3-pyridinyl)azepanylamine;
N-methyl-N-[(3R)-1-(3-pyridinyl)azepanyl]amine;
(3S)-1-(6-chloro-3-pyridinyl)azepanylamine;
N-[(3S)-1-(6-chloro-3-pyridinyl)azepanyl]-N-methylamine;
(3R)-1-(6-chloro-3-pyridinyl)azepanylamine;
N-[(3R)-1-(6-chloro-3-pyridinyl)azepanyl]-N-methylamine;
(3S)-1-(5,6-dichloro-3-pyridinyl)azepanylamine;
N-[(3S)-1-(5,6-dichloro-3-pyridinyl)azepanyl]-N-methylamine;
(3R)-1-(5,6-dichloro-3-pyridinyl)azepanylamine;
N-[(3R)-1-(5,6-dichloro-3-pyridinyl)azepanyl]-N-methylamine;
(3S)-1-(6-chloro-5-methoxy-3-pyridinyl)azepanylamine;
N-[(3S)-1-(6-chloro-5-methoxy-3-pyridinyl)azepanyl]-N-methyl amine;
(3R)-1-(6-chloro-5-methoxy-3-pyridinyl)azepanylamine;
N-[(3R)-1-(6-chloro-5-methoxy-3-pyridinyl)azepanyl]-N-methylamine;
(3S)-1-(6-chloro-5-methyl-3-pyridinyl)azepanylamine;
N-[(3S)-1-(6-chloro-5-methyl-3-pyridinyl)azepanyl]-N-methylamine;
(3R)-1-(6-chloro-5-methyl-3-pyridinyl)azepanylamine;
N-[(3R)-1-(6-chloro-5-methyl-3-pyridinyl)azepanyl]-N-methylamine;
(3S)-1-(5-methoxy-3-pyridinyl)azepanylamine;
N-[(3S)-1-(5-methoxy-3-pyridinyl)azepanyl]-N-methylamine;
(3R)-1-(5-methoxy-3-pyridinyl)azepanylamine;
N-[(3R)-1-(5-methoxy-3-pyridinyl)azepanyl]-N-methylamine;
(3S)-1-(6-bromo-3-pyridinyl)azepanylamine;
N-[(3S)-1-(6-bromo-3-pyridinyl)azepanyl]-N-methylamine;
(3R)-1-(6-bromo-3-pyridinyl)azepanylamine;
N-[(3R)-1-(6-bromo-3-pyridinyl)azepanyl]-N-methylamine;
(3S)-1-(5-fluoro-3-pyridinyl)azepanylamine;
N-[(3S)-1-(5-fluoro-3-pyridinyl)azepanyl]-N-methylamine;
(3R)-1-(5-fluoro-3-pyridinyl)azepanylamine;
N-[(3R)-1-(5-fluoro-3-pyridinyl)azepanyl]-N-methylamine;
(3S)-1-(6-chloro-5-fluoro-3-pyridinyl)azepanylamine;
N-[(3S)-1-(6-chloro-5-fluoro-3-pyridinyl)azepanyl]-N-methylamine;
(3R)-1-(6-chloro-5-fluoro-3-pyridinyl)azepanylamine;
N-[(3R)-1-(6-chloro-5-fluoro-3-pyridinyl)azepanyl]-N-methylamine;
(3S)-1-(6-bromo-5-fluoro-3-pyridinyl)azepanylamine;
N-[(3S)-1-(6-bromo-5-fluoro-3-pyridinyl)azepanyl]-N-methylamine;
(3R)-1-(6-bromo-5-fluoro-3-pyridinyl)azepanylamine;
N-[(3R)-1-(6-bromo-5-fluoro-3-pyridinyl)azepanyl]-N-methylamine;
(3S)-1-(5-bromo-6-chloro-3-pyridinyl)azepanylamine;
N-[(3S)-1-(5-bromo-6-chloro-3-pyridinyl)azepanyl]-N-methylamine;
(3R)-1-(5-bromo-6-chloro-3-pyridinyl)azepanylamine;
N-[(3R)-1-(5-bromo-6-chloro-3-pyridinyl)azepanyl]-N-methylamine;
(3S)-1-(6-bromo-5-chloro-3-pyridinyl)azepanylamine;
N-[(3S)-1-(6-bromo-5-chloro-3-pyridinyl)azepanyl]-N-methylamine;
(3R)-1-(6-bromo-5-chloro-3-pyridinyl)azepanylamine;
N-[(3R)-1-(6-bromo-5-chloro-3-pyridinyl)azepanyl]-N-methylamine;
(3 S)-1-(6-bromo-5-ethoxy-3-pyridinyl)azepanylamine;
N-[(3S)-1-(6-bromo-5-ethoxy-3-pyridinyl)azepanyl]-N-methylamine;
(3R)-1-(6-bromo-5-ethoxy-3-pyridinyl)azepanylamine;
N-[(3R)-1-(6-bromo-5-ethoxy-3-pyridinyl)azepanyl]-N-methylamine;
(3S)-1-(5-cyano-3-pyridinyl)azepanylamine;
N-[(3S)-1-(5-cyano-3-pyridinyl)azepanyl]-N-methylamine;
(3R)-1-(5-cyano-3-pyridinyl)azepanylamine;
N-[(3R)-1-(5-cyano-3-pyridinyl)azepanyl]-N-methylamine;
(3S)-1-(5-ethynyl-3-pyridinyl)azepanylamine;
N-[(3S)-1-(5-ethynyl-3-pyridinyl)azepanyl]-N-methylamine;
(3R)-1-(5-ethynyl-3-pyridinyl)azepanylamine;
N-[(3R)-1-(5-ethynyl-3-pyridinyl)azepanyl]-N-methylamine;
(3S)-1-furo[3,2-b]pyridin-6-ylazepanylamine;
N-[(3S)-1-furo[3,2-b]pyridin-6-ylazepanyl]-N-methylamine;
(3R)-1-furo[3,2-b]pyridin-6-ylazepanylamine; and
N-[(3R)-1-furo[3,2-b]pyridin-6-ylazepanyl]-N-methylamine.

In another embodiment of the present invention are disclosed compounds of formula VII

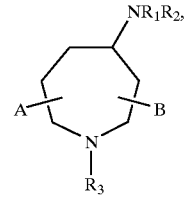

or pharmaceutically acceptable salts thereof wherein A, B, $R_1$, $R_2$, and $R_3$ are as defined in formula I.

In another embodiment are disclosed compounds of formula VII wherein A is as defined in formula I; B is absent; $R_1$ and $R_2$ are independently selected from hydrogen and lower alkyl wherein hydrogen and methyl are preferred; $R_3$ is

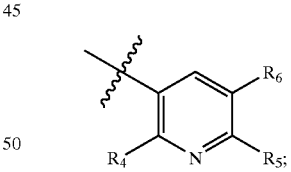

$R_4$ is hydrogen; $R_5$ is selected from hydrogen, halogen, and lower alkyl; and $R_6$ is selected from hydrogen, cyano, haloalkoxy, haloalkyl, halogen, hydroxy, lower alkoxy, lower alkyl, lower alkynyl, and nitro.

The following additional compounds, representative of formula VII, may be prepared by one skilled in the art using known synthetic chemistry methodology or by using synthetic chemistry methodology described in the Schemes and Examples contained herein.

(4S)-1-(3-pyridinyl)azepanylamine;
N-methyl-N-[(4S)-1-(3-pyridinyl)azepanyl]amine;
(4R)-1-(3-pyridinyl)azepanylamine;
N-methyl-N-[(4R)-1-(3-pyridinyl)azepanyl]amine;
(4S)-1-(6-chloro-3-pyridinyl)azepanylamine;
N-[(4S)-1-(6-chloro-3-pyridinyl)azepanyl]-N-methylamine;

(4R)-1-(6-chloro-3-pyridinyl)azepanylamine;
N-[(4R)-1-(6-chloro-3-pyridinyl)azepanyl]-N-methylamine;
(4S)-1-(5,6-dichloro-3-pyridinyl)azepanylamine;
N-[(4S)-1-(5,6-dichloro-3-pyridinyl)azepanyl]-N-methylamine;
(4R)-1-(5,6-dichloro-3-pyridinyl)azepanylamine;
N-[(4R)-1-(5,6-dichloro-3-pyridinyl)azepanyl]-N-methylamine;
(4S)-1-(6-chloro-5-methoxy-3-pyridinyl)azepanylamine;
N-[(4S)-1-(6-chloro-5-methoxy-3-pyridinyl)azepanyl]-N-methylamine;
(4R)-1-(6-chloro-5-methoxy-3-pyridinyl)azepanylamine;
N-[(4R)-1-(6-chloro-5-methoxy-3-pyridinyl)azepanyl]-N-methylamine;
(4S)-1-(6-chloro-5-methyl-3-pyridinyl)azepanylamine;
N-[(4S)-1-(6-chloro-5-methyl-3-pyridinyl)azepanyl]-N-methylamine;
(4R)-1-(6-chloro-5-methyl-3-pyridinyl)azepanylamine;
N-[(4R)-1-(6-chloro-5-methyl-3-pyridinyl)azepanyl]-N-methylamine;
(4S)-1-(5-methoxy-3-pyridinyl)azepanylamine;
N-[(4S)-1-(5-methoxy-3-pyridinyl)azepanyl]-N-methylamine;
(4R)-1-(5-methoxy-3-pyridinyl)azepanylamine;
N-[(4R)-1-(5-methoxy-3-pyridinyl)azepanyl]-N-methylamine;
(4S)-1-(6-bromo-3-pyridinyl)azepanylamine;
N-[(4S)-1-(6-bromo-3-pyridinyl)azepanyl]-N-methylamine;
(4R)-1-(6-bromo-3-pyridinyl)azepanylamine;
N-[(4R)-1-(6-bromo-3-pyridinyl)azepanyl]-N-methylamine;
(4S)-1-(5-fluoro-3-pyridinyl)azepanylamine;
N-[(4S)-1-(5-fluoro-3-pyridinyl)azepanyl]-N-methylamine;
(4R)-1-(5-fluoro-3-pyridinyl)azepanylamine;
N-[(4R)-1-(5-fluoro-3-pyridinyl)azepanyl]-N-methylamine;
(4S)-1-(6-chloro-5-fluoro-3-pyridinyl)azepanylamine;
N-[(4S)-1-(6-chloro-5-fluoro-3-pyridinyl)azepanyl]-N-methylamine;
(4R)-1-(6-chloro-5-fluoro-3-pyridinyl)azepanylamine;
N-[(4R)-1-(6-chloro-5-fluoro-3-pyridinyl)azepanyl]-N-methylamine;
(4S)-1-(6-bromo-5-fluoro-3-pyridinyl)azepanylamine;
N-[(4S)-1-(6-bromo-5-fluoro-3-pyridinyl)azepanyl]-N-methylamine;
(4R)-1-(6-bromo-5-fluoro-3-pyridinyl)azepanylamine;
N-[(4R)-1-(6-bromo-5-fluoro-3-pyridinyl)azepanyl]-N-methylamine;
(4S)-1-(5-bromo-6-chloro-3-pyridinyl)azepanylamine;
N-[(4S)-1-(5-bromo-6-chloro-3-pyridinyl)azepanyl]-N-methylamine;
(4R)-1-(5-bromo-6-chloro-3-pyridinyl)azepanylamine;
N-[(4R)-1-(5-bromo-6-chloro-3-pyridinyl)azepanyl]-N-methylamine;
(4S)-1-(6-bromo-5-chloro-3-pyridinyl)azepanylamine;
N-[(4S)-1-(6-bromo-5-chloro-3-pyridinyl)azepanyl]-N-methylamine;
(4R)-1-(6-bromo-5-chloro-3-pyridinyl)azepanylamine;
N-[(4R)-1-(6-bromo-5-chloro-3-pyridinyl)azepanyl]-N-methyl amine;
(4S)-1-(6-bromo-5-ethoxy-3-pyridinyl)azepanylamine;
N-[(4S)-1-(6-bromo-5-ethoxy-3-pyridinyl)azepanyl]-N-methylamine;
(4R)-1-(6-bromo-5-ethoxy-3-pyridinyl)azepanylamine;
N-[(4R)-1-(6-bromo-5-ethoxy-3-pyridinyl)azepanyl]-N-methylamine;
(4S)-1-(5-cyano-3-pyridinyl)azepanylamine;
N-[(4S)-1-(5-cyano-3-pyridinyl)azepanyl]-N-methylamine;
(4R)-1-(5-cyano-3-pyridinyl)azepanylamine;
N-[(4R)-1-(5-cyano-3-pyridinyl)azepanyl]-N-methylamine;
(4S)-1-(5-ethynyl-3-pyridinyl)azepanylamine;
N-[(4S)-1-(5-ethynyl-3-pyridinyl)azepanyl]-N-methylamine;
(4R)-1-(5-ethynyl-3-pyridinyl)azepanylamine;
N-[(4R)-1-(5-ethynyl-3-pyridinyl)azepanyl]-N-methylamine;
(4S)-1-furo[3,2-b]pyridin-6-ylazepanylamine;
N-[(4S)-1-furo[3,2-b]pyridin-6-ylazepanyl]-N-methylamine;
(4R)-1-furo[3,2-b]pyridin-6-ylazepanylamine; and
N-[(4R)-1-furo[3,2-b]pyridin-6-ylazepanyl]-N-methylamine.

Another embodiment of the present invention relates to pharmaceutical compositions comprising a therapeutically effective amount of a compound of formula I or a pharmaceutically acceptable salt thereof in combination with a pharmaceutically acceptable carrier.

Another embodiment of the present invention relates to a method for selectively controlling neurotransmitter release in a mammal comprising administering to a mammal in need of such treatment a therapeutically effective amount of a compound of formula I.

Another embodiment of the present invention relates to a method of treating a disorder, such as Alzheimer's disease, Parkinson's disease, memory dysfunction, Tourette's syndrome, sleep disorders, attention deficit hyperactivity disorder, neurodegeneration, inflammation, neuroprotection, anxiety, depression, mania, schizophrenia, anorexia and other eating disorders, AIDS-induced dementia, epilepsy, urinary incontinence, Crohn's disease, migraines, premenstraul syndrome, erectile dysfunction, substance abuse, smoking cessation, inflammatory bowel syndrome, and pain, in a host mammal in need of such treatment comprising administering a therapeutically effective amount of a compound of formula I.

Another embodiment of the present invention relates to a method for controlling pain in a mammal in need of such treatment comprising administering a therapeutically effective amount of a compound of formula I in combination with an opioid and a pharmaceutically acceptable carrier.

Another embodiment of the present invention relates to a method for controlling pain in a mammal in need of such treatment comprising administering a therapeutically effective amount of a compound of formula I in combination with a non-steroid anti-inflammatory agent and a pharmaceutically acceptable carrier:

Another embodiment of the present invention relates to a method for controlling pain in a mammal in need of such treatment comprising administering a therapeutically effective amount of a compound of formula I in combination with a tricyclic antidepressant and a pharmaceutically acceptable carrier.

Another embodiment of the present invention relates to a method for controlling pain in a mammal in need of such treatment comprising administering a therapeutically effective amount of a compound of formula I in combination with an anticonvulsant such as gabapentin or pregabalin and a pharmaceutically acceptable carrier.

In another embodiment of the present invention are disclosed compounds of formula VIII

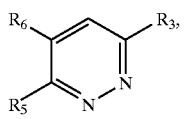

VIII or pharmaceutically acceptable salts or prodrugs thereof wherein, $R_3$ is selected from the group consisting of

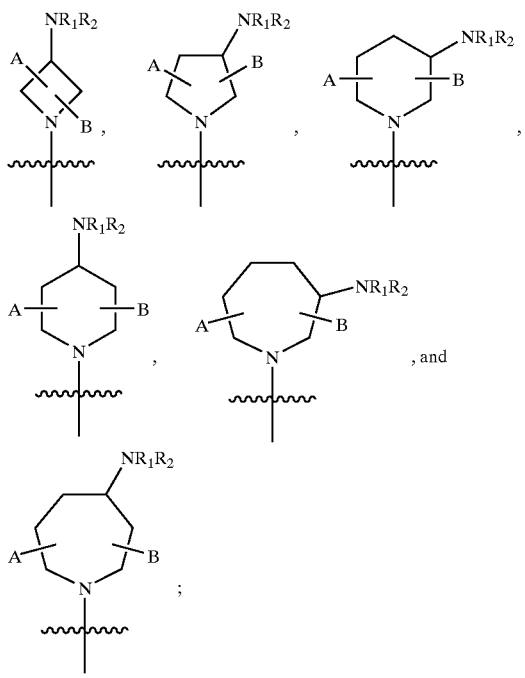

$R_1$ is alkyl preferably methyl; $R_2$ is selected from hydrogen and alkyl preferably selected from hydrogen and methyl; and $R_5$, $R_6$, A and B are as defined in formula I.

Another embodiment of the present invention relates to pharmaceutical compositions comprising a therapeutically effective amount of a compound of formula VIII or a pharmaceutically acceptable salt thereof in combination with a pharmaceutically acceptable carrier.

Another embodiment of the present invention relates to a method for selectively controlling neurotransmitter release in a mammal comprising administering to a mammal in need of such treatment a therapeutically effective amount of a compound of formula VIII.

Another embodiment of the present invention relates to a method of treating a disorder, such as Alzheimer's disease, Parkinson's disease, memory dysfunction, Tourette's syndrome, sleep disorders, attention deficit hyperactivity disorder, neurodegeneration, inflammation, neuroprotection, anxiety, depression, mania, schizophrenia, anorexia and other eating disorders, AIDS-induced dementia, epilepsy, urinary incontinence, Crohn's disease, migraines, premenstraul syndrome, erectile dysfunction, substance abuse, smoking cessation, inflammatory bowel syndrome, and pain, in a host mammal in need of such treatment comprising administering a therapeutically effective amount of a compound of formula VIII.

Another embodiment of the present invention relates to a method for controlling pain in a mammal in need of such treatment comprising administering a therapeutically effective amount of a compound of formula VIII in combination with an opioid and a pharmaceutically acceptable carrier.

Another embodiment of the present invention relates to a method for controlling pain in a mammal in need of such treatment comprising administering a therapeutically effective amount of a compound of formula VIII in combination with a non-steroid anti-inflammatory agent and a pharmaceutically acceptable carrier.

Another embodiment of the present invention relates to a method for controlling pain in a mammal in need of such treatment comprising administering a therapeutically effective amount of a compound of formula VIII in combination with a tricyclic antidepressant and a pharmaceutically acceptable carrier.

Another embodiment of the present invention relates to a method for controlling pain in a mammal in need of such treatment comprising administering a therapeutically effective amount of a compound of formula VIII in combination with an anticonvulsant such as gabapentin or pregabalin and a pharmaceutically acceptable carrier.

Definition of Terms

As used throughout this specification and the appended claims, the following terms have the following meanings.

The term "alkenyl," as used herein, refers to a straight or branched chain hydrocarbon containing from 2 to 10 carbons, wherein 2 to 6 carbon atoms are preferred, and containing at least one carbon—carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy," as used herein, refers to an alkyl group, as defined herein, appended to the parent molecular moiety through an oxy moiety, as defined herein. Representative examples of alkoxy include, but are not limited to, methoxy, ethoxy, propoxy, 2-propoxy, butoxy, tert-butoxy, pentyloxy, and hexyloxy.

The term "alkoxyalkoxy," as used herein, refers to an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl," as used herein, refers to an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkyl," as used herein, refers to a straight or branched chain hydrocarbon containing from 1 to 10 carbon atoms, wherein 1 to 6 carbon atoms are preferred. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy," as used herein, refers to an alkylcarbonyl group, as defined herein, appended to the parent molecular moiety through an oxy moiety, as defined herein. Representative examples of alkylcarbonyloxy include, but are not limited to, acetyloxy, ethylcarbonyloxy, and tert-butylcarbonyloxy.

The term "alkylthio," as used herein, refers to an alkyl group, as defined herein, appended to the parent molecular moiety through a thio moiety, as defined herein. Representative examples of alkylthio include, but are not limited, methylsulfanyl, ethylsulfanyl, tert-butylsulfanyl, and hexylsulfanyl.

The term "alkynyl," as used herein, refers to a straight or branched chain hydrocarbon group containing from 2 to 10 carbon atoms, wherein 2 to 6 carbon atoms are preferred, and containing at least one carbon—carbon triple bond. Representative examples of alkynyl include, but are not limited, to acetylenyl, 1-propynyl, 2-propynyl, 3-butynyl, 2-pentynyl, and 1-butynyl.

The term "amino," as used herein, refers to a —NR$_{20}$R$_{21}$ group wherein R$_{20}$ and R$_{21}$ are independently selected from hydrogen, alkyl, and alkylcarbonyl as defined herein. Representative examples of amino include, but are not limited, amino, methylamino, dimethylamino, ethylamino, and methylcarbonylamino.

The term "aminoalkyl," as used herein, refers to an amino group, as defined herein, appended to the parent molecular moiety through an alkyl group, as defined herein. Representative examples of aminoalkyl include, but are not limited, aminomethyl, (methylamino)methyl, 2-aminoethyl, and (dimethylamino)methyl.

The term "aminocarbonyl," as used herein, refers to an amino group, as defined herein, appended to the parent molecular moiety through a carbonyl group, as defined herein. Representative examples of aminocarbonyl include, but are not limited, aminocarbonyl, dimethylaminocarbonyl, methylaminocarbonyl, and ethylaminocarbonyl.

The term "aminocarbonylalkyl," as used herein, refers to an aminocarbonyl group, as defined herein, appended to the parent molecular moiety through an alkyl group, as defined herein. Representative examples of aminocarbonylalkyl include, but are not limited to, 2-amino-2-oxoethyl, 2-(methylamino)-2-oxoethyl, 4-amino-4-oxobutyl, and 4-(dimethylamino)-4-oxobutyl.

The term "aminosulfonyl," as used herein, refers to an amino group, as defined herein, appended to the parent molecular moiety through a sulfonyl group, as defined herein. Representative examples of aminosulfonyl include, but are not limited, aminosulfonyl, dimethylaminosulfonyl, methylaminosulfonyl, and ethylaminosulfonyl.

The term "aryl," as used herein, refers to a monocyclic-ring system, or a fused bicyclic-ring system wherein one or more of the fused rings are aromatic. Representative examples of aryl include, but are not limited to, azulenyl, indanyl, indenyl, naphthyl, phenyl, and tetrahydronaphthyl.

The aryl groups of this invention can be substituted with 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, amino, aminosulfonyl, carboxy, carboxyalkyl, cyano, cyanoalkyl, formyl, formylalkyl, halogen, haloalkyl, hydroxy, hydroxyalkyl, mercapto, and nitro.

The term "carbonyl," as used herein, refers to a —C(O)— group.

The term "carboxy," as used herein, refers to a —CO$_2$H group.

The term "carboxyalkyl," as used herein, refers to a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano," as used herein, refers to a —CN group.

The term "cyanoalkyl," as used herein, refers to a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "formyl," as used herein, refers to a —C(O)H group.

The term "formylalkyl," as used herein, refers to a formyl group, as defined herein, appended to the parent molecular moiety through an alkyl group, as defined herein. Representative examples of formylalkyl include, but are not limited to, formylmethyl and 2-formylethyl.

The term "halo" or "halogen," as used herein, refers to —Cl, —Br, —I or —F.

The term "haloalkoxy," as used herein, refers to at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heterocycle" or "heterocyclic," as used herein, refers to a monocyclic, bicyclic, or tricyclic ring system. Monocyclic ring systems are exemplified by any 3- or 4-membered ring containing a heteroatom independently selected from oxygen, nitrogen and sulfur; or a 5-, 6 or 7-membered ring containing one, two or three heteroatoms wherein the heteroatoms are independently selected from nitrogen, oxygen and sulfur. The 5-membered ring has from 0–2 double bonds and the 6- and 7-membered ring have from 0–3 double bonds. Representative examples of monocyclic ring systems include, but are not limited to, azetidinyl, azepinyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl(thiomorpholine sulfone), thiopyranyl, triazinyl, triazolyl, and trithianyl. Bicyclic ring systems are exemplified by any of the above monocyclic ring systems fused to an aryl group as defined herein, a cycloalkyl group as defined herein, or another monocyclic ring system. Representative examples of bicyclic ring systems include but are not limited to, for example, benzimidazolyl, benzothiazolyl, benzothienyl, benzoxazolyl, benzofuranyl, benzopyranyl, benzothiopyranyl, benzodioxinyl, 1,3-benzodioxolyl, cinnolinyl, indazolyl, indolyl, indolinyl, indolizinyl, naphthyridinyl, isobenzofuranyl, isobenzothienyl, isoindolyl, isoindolinyl, isoquinolinyl, phthalazinyl, pyranopyridyl, quinolinyl, quinolizinyl, quinoxalinyl, quinazolinyl, tetrahydroisoquinolinyl, tetrahydroquinolinyl, and thiopyranopyridyl. Tricyclic rings systems are exemplified by any of the above bicyclic ring systems fused to an aryl group as defined herein, a cycloalkyl group as defined herein, or a monocyclic ring system. Representative examples of tricyclic ring systems include, but are not limited to, acridinyl, carbazolyl, carbolinyl, dibenzofuranyl, dibenzothiophenyl, naphthofuranyl, naphthothiophenyl, oxanthrenyl, phenazinyl, phenoxathiinyl, phenoxazinyl, phenothiazinyl, thianthrenyl, thioxanthenyl, and xanthenyl.

The heterocycles of this invention can be substituted with 1, 2, or 3 substituents independently selected from alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, amino, aminosulfonyl, carboxy, carboxyalkyl, cyano, cyanoalkyl, formyl, formylalkyl, halogen, haloalkyl, hydroxy, hydroxyalkyl, mercapto, and nitro.

The term "hydroxy," as used herein, refers to an —OH group.

The term "hydroxyalkyl," as used herein, refers to a hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, and 2-ethyl-4-hydroxyheptyl.

The term "lower alkoxy," as used herein, is a subset of alkoxy as defined herein and refers to a lower alkyl group, as defined herein, appended to the parent molecular moiety through an oxy group, as defined herein. Representative examples of lower alkoxy include, but are not limited to, methoxy, ethoxy, propoxy, 2-propoxy, butoxy, and tert-butoxy.

The term "lower alkyl," as used herein, is a subset of alkyl as defined herein and refers to a straight or branched chain hydrocarbon group containing from 1 to 4 carbon atoms. Examples of lower alkyl are methyl, ethyl, n-propyl, iso-propyl, n-butyl, iso-butyl, sec-butyl, and tert-butyl.

The term "lower alkynyl," as used herein, is a subset of alkynyl as defined herein and refers to a straight or branched chain hydrocarbon group containing from 2 to 4 carbon atoms and containing at least one carbon—carbon triple bond. Representative examples of lower alkynyl include, but are not limited, to acetylenyl, 1-propynyl, 2-propynyl, and 3-butynyl.

The term "mercapto," as used herein, refers to a —SH group.

The term "mercaptoalkyl," as used herein, refers to a mercapto group, as defined herein, appended to the parent molecular moiety through an alkyl group, as defined herein. Representative examples of mercaptoalkyl include, but are not limited to, sulfanylmethyl, 2-sulfanylethyl and 3-sulfanylpropyl.

The term "nitrogen protecting group" or "N-protecting group," as used herein, refers to those groups intended to protect an amino group against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (Cbz), formyl, phenylsulfonyl, pivaloyl, tert-butoxycarbonyl (Boc), trifluoroacetyl, and triphenylmethyl (trityl). Commonly used N-protecting groups are disclosed in T. W. Greene and P. G. M. Wuts, Protective Groups in Organic Synthesis, 3rd edition, John Wiley & Sons, New York (1999).

The term "nitro," as used herein, refers to a —NO$_2$ group.

The term "oxo," as used herein, refers to a =O moiety.

The term "oxy," as used herein, refers to a —O— moiety.

The term "sulfonyl," as used herein, refers to a —SO$_2$— group.

The term "thio," as used herein, refers to a —S— moiety.

Compounds of the present invention can exist as stereoisomers, wherein asymmetric or chiral centers are present. Stereoisomers are designated "R" or "S," depending on the configuration of substituents around the chiral carbon atom. The terms "R" and "S" used herein are configurations as defined in (IUPAC 1974 Recommendations for Section E, Fundamental Stereochemistry, Pure Appl. Chem., (1976), 45: 13–30). In particular, the stereochemistry at the ring carbon atom that is attached to the —NR$_1$R$_2$ nitrogen, shown in formula I, may independently be either (R) or (S) unless specifically noted otherwise.

The present invention contemplates various stereoisomers and mixtures thereof which are specifically included within the scope of this invention. Stereoisomers include enantiomers, diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

The compounds of the present invention can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts are well-known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

In Vitro Data

Determination of Nicotinic Acetylcholine Receptor Binding Potencies

Compounds of the invention were subjected to in vitro assays against the nicotinic acetylcholine receptor as described below and were found to be effective binders to the receptor. The In Vitro protocols for determination of nicotinic acetylcholine channel receptor binding potencies of ligands were determined as follows.

Binding of [$^3$H]-cytisine ([$^3$H]-CYT) to neuronal nicotinic acetylcholine receptors was accomplished using crude synaptic membrane preparations from whole rat brain (Pabreza et al., Molecular Pharmacol., 1990, 39:9). Washed membranes were stored at −80° C. prior to use. Frozen aliquots were slowly thawed and resuspended in 20 volumes of buffer (containing: 120 mM NaCl, 5 mM KCl, 2 mM MgCl$_2$, 2 mM CaCl$_2$ and 50 mM Tris-Cl, pH 7.4 @4° C.). After centrifuging at 20,000× g for 15 minutes, the pellets were resuspended in 30 volumes of buffer The test compounds were dissolved in water to make 10 mM stock solutions. Each solution was then diluted (1:100) with buffer (as above) and further taken through seven serial log dilution to produce test solution from 10$^{-5}$ to 10$^{-11}$ M.

Homogenate (containing 125–150 μg protein) was added to triplicate tubes containing the range of concentration of test compound described above and [$^3$H]-CYT (1.25 nM) in a final volume of 500 μL. Samples were incubated for 60 minutes at 4° C., then rapidly filtered through Whatman GF/B filters presoaked in 0.5% polyethyleneimine using 3×4 mL of ice-cold buffer. The filters are counted in 4 ml of Ecolume® (ICN). Nonspecific binding was determined in the presence of 10 μm nicotine and values were expressed as a percentage of total binding. IC$_{50}$ values were determined with the RS-1 (BBN) nonlinear least squares curve fitting program and IC$_{50}$ values were converted to Ki values using the Cheng and Prusoff correction (K$_i$=IC$_{50}$/(1+[ligand]/Kd of ligand).

The results are detailed in Table 1.

TABLE 1

Binding Data

| Example Number | Average K(nM) |
|---|---|
| 1 | 44 |
| 2 | 0.10 |
| 3 | 61 |
| 4 | 0.22 |
| 5 | 5.5 |
| 6 | 100 |
| 7 | 0.12 |
| 8 | 0.23 |
| 9 | 2.0 |
| 10 | 0.15 |
| 11 | 3.0 |
| 12 | 114 |
| 13 | 1.0 |
| 14 | 6.3 |
| 15 | 0.03 |
| 16 | 5.1 |
| 17 | 0.03 |
| 18 | 0.58 |
| 19 | 0.050 |
| 20 | 0.59 |
| 21 | 0.13 |
| 22 | 13 |
| 23 | 0.13 |
| 24 | 4.1 |
| 25 | 0.34 |
| 26 | 1.5 |
| 27 | 0.44 |
| 28 | 39 |
| 29 | 0.70 |
| 30 | 12 |
| 31 | 3.5 |
| 32 | 195 |
| 37 | 92 |
| 38 | 0.51 |
| 39 | 85 |
| 40 | 5.4 |
| 41 | 0.89 |
| 42 | 83 |
| 43 | 1.1 |
| 44 | 205 |
| 45 | 0.35 |
| 46 | 60 |
| 47 | 0.38 |
| 48 | 166 |
| 49 | 4.8 |
| 50 | 174 |
| 51 | 714 |

In Vivo Data

Determination of Effectiveness of Nicotinic Acetylcholine Receptor Ligands as Analgesic Agents in the Mouse Hot Plate Paradigm An in vivo protocol was utilized to determine the effectiveness of nicotinic acetylcholine receptor ligands as analgesic agents in the mouse hot plate paradigm.

Separate groups of mice (n=8/group) were utilized for each dose group. All drugs were administered by the intraperitoneal route of administration. Test drugs were dissolved in water to make a 6.2 mm stock solution. Animals were dosed with this solution (10 mL/kg body weight) for a 62 micromol/kg dose. Lower doses were administered similarly, following serial dilution of the stock solution in half log increments. Animals were dosed 30 minutes prior to testing in the hot plate. The hot-plate utilized was an automated analgesia monitor (Model #AHP16AN, Omnitech Electronics, Inc. of Columbus, Ohio). The temperature of the hot plate was maintained at 55° C. and a cut-off time of 180 seconds was utilized. Latency until the tenth jump was recorded as the dependent measure. An increase in the tenth jump latency relative to the control was considered an effect.

Table 2 shows the minimally effective dose (MED), among the doses tested, at which a significant effect, as described above, was observed for the present compounds. The data shows that selected compounds of the invention show a significant antinociceptive effect at doses ranging from 0.62 to 62 µmol/kg

TABLE 2

Mouse Hot Plate Data

| Example Number | (MED) µmol/kg |
| --- | --- |
| 1 | 62 |
| 2 | 6.2 |
| 3 | 62 |
| 4 | 1.9 |
| 5 | 62 |
| 7 | 6.2 |
| 8 | 19 |
| 9 | 62 |
| 15 | 6.2 |
| 16 | 1.9 |
| 17 | 6.2 |
| 18 | 6.2 |
| 19 | 6.2 |
| 20 | 19 |
| 21 | 6.2 |
| 22 | 19 |
| 23 | 62 |
| 24 | 62 |
| 25 | 6.2 |
| 29 | 19 |
| 31 | 6.2 |
| 38 | 6.2 |
| 41 | 19 |
| 42 | 62 |
| 43 | 0.62 |
| 45 | 0.62 |
| 46 | 62 |
| 47 | 1.9 |
| 49 | 62 |

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration.

The selected dosage level will depend upon the activity of the particular compound, the route of administration, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.001 to about 1000 mg/kg/day. For purposes of oral administration, more preferable doses can be in the range of from about 0.001 to about 5 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracistemally, intravaginally, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar— agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar—agar, tragacanth and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Compounds of the present invention that are formed by in vivo conversion of a different compound that was administered to a mammal are intended to be included within the scope of the present invention.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

The present compounds may have activity against disorders which are mediated through the central nervous system. The following references describe various disorders affected by nicotinic acetylcholine receptors: 1) Williams, M.; Arneric, S. P.: Beyond the Tobacco Debate: dissecting out the therapeutic potential of nicotine. Exp. Opin. Invest. Drugs (1996)5(8): 1035–1045; 2) Arneric, S. P.; Sullivan, J. P.; Williams, W.: Neuronal nicotinic acetylcholine receptors. Novel targets for central nervous system theraputics. In: Psychopharmacology: The Fourth Generation of Progress. Bloom F E, Kupfer D J (Eds.), Raven Press, New York (1995): 95–109; 3) Arneric, S. P.; Holladay, M. W.; Sullivan, J: P.: Cholinergic channel modulators as a novel therapeutic strategy for Alzheimer's disease. Exp. Opin. Invest. Drugs (1996) 5(1): 79–100; 4) Lindstrom, J.: Nicotinic Acetylcholine Receptors in Health and Disease. Molecular Neurobiology (1997)15: 193–222; and 5) Lloyd, G K; Menzaghi, F; Bontempi B; Suto, C; Siegel, R; Akong, M; Stauderman, K; Velicelebi, G; Johnson, E; Harpold, M M; Rao, T S; Sacaan, A I; Chavez-Noriega, L E; Washburn, M S; Vernier, J M; Cosford, N D P; McDonald, L A: The potential of subtype-selective neuronal nicotinic acetylcholine receptor agonists as therapeutic agents. Life Sciences (1998)62(17/18): 1601–1606. These disorders include, but are not limited to the following: pain (references 1 and 2), Alzheimer's disease (references 1–5), Parkinson's disease (references 1, 4 and 5), memory dysfunction, Tourette's syndrome (references 1, 2 and 4), sleep disorders (reference 1), attention deficit hyperactivity disorder (references 1 and 3), neurodegeneration, inflammation, neuroprotection (references 2 and 3), amyotrophic atral sclerosis, anxiety (references 1, 2 and 3), depression (reference 2), mania, schizophrenia (references 1, 2 and 4), anorexia and other eating disorders, AIDS-induced dementia, epilepsy (references 1, 2 and 4), urinary incontinence (reference I), Crohn's disease, migraines, PMS, erectile disjunction, substance abuse, smoking cessation (references 1 and 2) and inflammatory bowel syndrome (references 1 and 4) among others.

Abbreviations

Abbreviations which have been used in the descriptions of the Schemes and the Examples that follow are: Ac for acetyl; AcOH for acetic acid; BINAP for 2,2'-bis (diphenylphosphino)-1,1'-binaphthyl; Boc for tert-butoxycarbonyl; $(Boc)_2O$ for di-tert-butyl dicarbonate; dba for dibenzylideneacetone; DMF for N,N-dimethylformamide; dppf for 1,1'-bis(diphenylphosphino)ferrocene; EtOAc for ethyl acetate; $Et_2O$ for diethyl ether; EtOH for ethanol; eq for equivalents; formalin for a solution of formaldehyde (37% by weight) in water; HPLC for high pressure liquid chromatography; LAH for lithium aluminum hydride; MeOH for methanol; Ms for mesylate ($SO_2CH_3$); Tf for triflate ($SO_2CF_3$); TFA for trifluoroacetic acid; THF for tetrahydrofuran; TMS for trimethylsilyl; Ts for tosylate; and TsOH for para-toluenesulfonic acid.

Preparation of Compounds of the Present Invention

The compounds and processes of the present invention will be better understood in connection with the following synthetic Schemes and methods which illustrate a means by which the compounds of the present invention can be prepared.

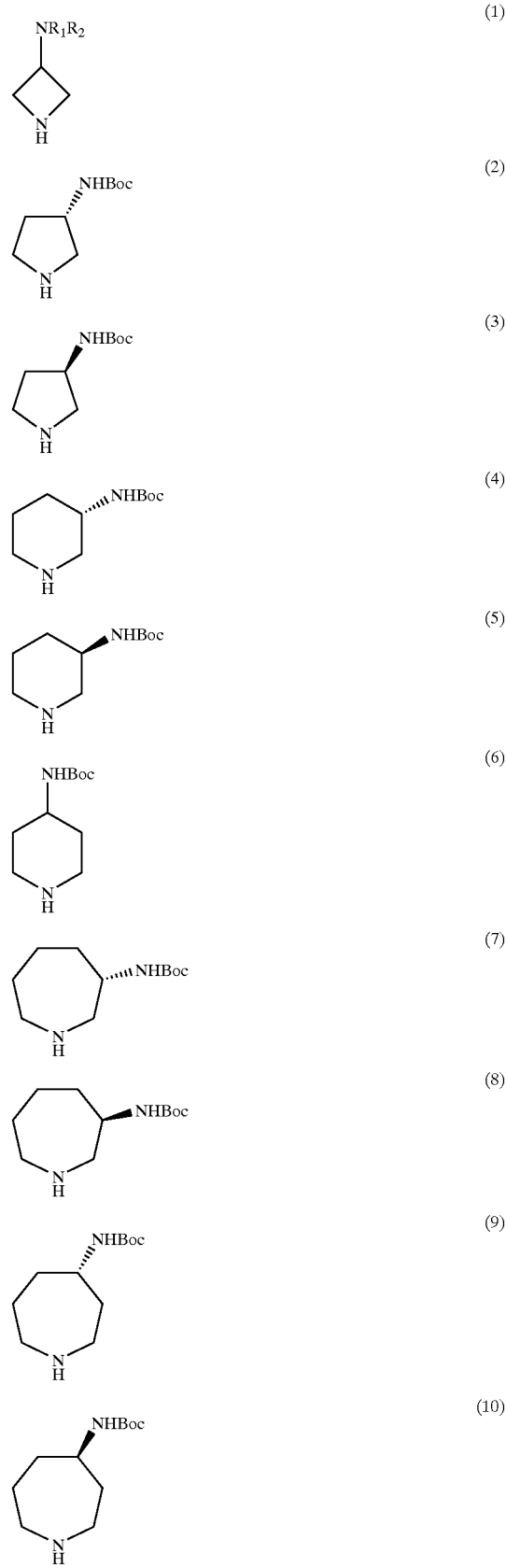

Scheme 1

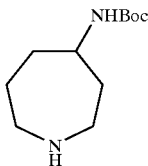

(11)

Azetidines of general formula (1), wherein $R_1$ and $R_2$ are selected from hydrogen, alkyl and a nitrogen protecting group such as Boc or Cbz, can be prepared as described in (Okada, T. et al, Chem. Pharm. Bull. (1993) 41(1) 126–131). Pyrrolidines (2) and (3) can be purchased (TCI) or prepared as described in (Moon S. H and Lee S., Syn. Comm., (1998) 28(21) 3919–3926). Piperidines (4) and (5) can be prepared as described in (Moon S. H and Lee S., Syn. Comm., (1998) 28(21) 3919–3926). Piperidine (6) can be purchased (Astatech) or prepared from an amine and 4-piperidinone under reductive amination conditions. Azepanes (7) and (8) can be prepared as described in (Moon S. H and Lee S., Syn. Comm., (1998) 28(21) 3919–3926). Alternatively, azepanes (9) and (10) can be prepared from the racemate (11) which can be prepared as described in (DeRuiter, J. et al, J. Heterocyclic Chem. (1992) 779–786). The racemate (11) can be separated into individual enantiomers (9) and (10) via techniques well known to those skilled in the art of organic chemistry such as chiral column chromatography or by the use of a chiral auxiliary.

Scheme 2

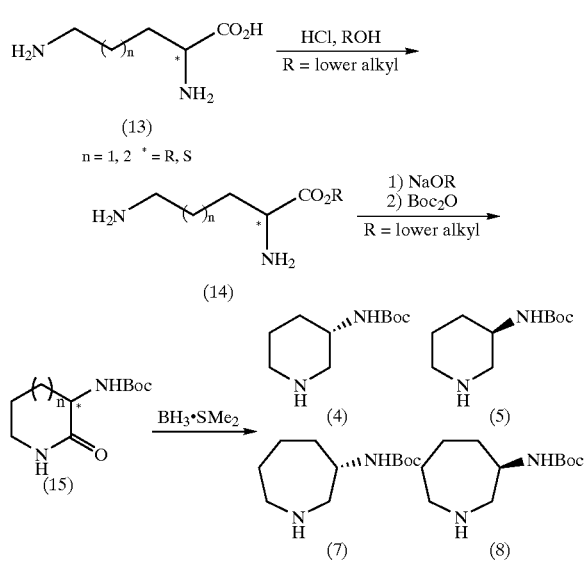

An alternative synthesis of piperidines (4) and (5) and azepanes (7) and (8) can be used as described in Scheme 2. Chiral amino acids of general formula (13), purchased commercially or prepared using chemistry methodology known to those skilled in the art of organic chemistry, can be treated with acid in an alcoholic solvent such as methanol to provide esters of general formula (14). Esters of general formula (14) can be treated with an alkoxide such as methoxide to effect ring closure and then treated with di-tert-butyl dicarbonate to provide lactams of general formula (15). Lactams of general formula (15) can be treated with a reducing agent such as borane-methyl sulfide complex or borane-tetrahydrofuran complex to provide mono protected diamines of general formula (4), (5), (7) or (8). Since stereochemistry is retained in this synthesis, optically pure amino acids of general formula (13) provide individual enantiomers of general formula (4), (5), (7) or (8).

Scheme 3

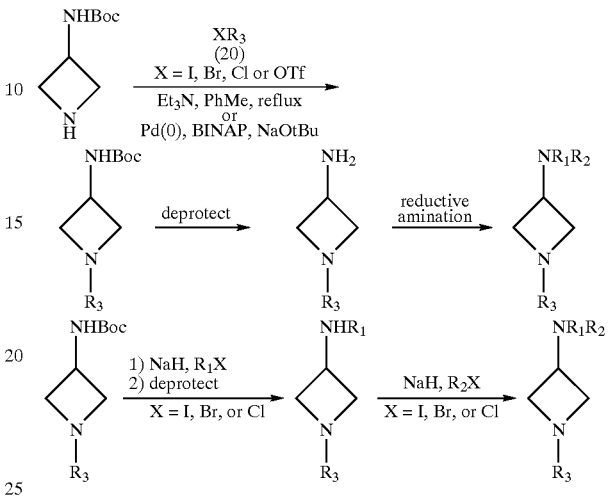

Coupling of heterocyclic halides or heterocyclic triflates to mono protected diamines can be accomplished as described in Scheme 3. Diamines of general formula (1–11) from Scheme 1, wherein tert-butyl 3-azetidinylcarbamate shown in Scheme 3 is a representative mono protected diamine, can be treated with a heterocyclic halide/triflate of general formula (20), wherein $R_3$ is as defined in formula I and X is selected from I, Br, Cl, or OTf, and a base such as triethyl amine to provide Boc protected heterocyclic diamines. Alternatively, less-reactive heterocycles can be coupled using palladium-mediated procedures as described in (Wagaw and Buchwald, JOC (1996) 61, 7240–7241). Diamines of general formula (1–11) can be treated with heterocyclic halides of general formula (20), a palladium catalyst such as $Pd_2(dba)_3$, a base such as sodium tert-butoxide or cesium carbonate or potassium phosphate and either BINAP, CyMAP, or MOP to provide Boc protected heterocyclic diamines.

Boc protected heterocyclic diamines can be treated with an acid such as trifluoroacetic acid or 4.5N HCl in 1,4-dioxane to provide heterocyclic diamines of the present invention. The free amine can be further elaborated under reductive amination conditions well known to those skilled in the art of organic chemistry to provide both mono and di N-alkyl heterocyclic diamines. Alternatively, Boc protected heterocyclic diamines can be treated with sodium hydride and an alkylating agent such as iodomethane or ethyl bromide and then deprotected with acid to provide mono N-alkyl heterocyclic diamines of the present invention. This process can be repeated (sodium hydride and alkylating agent) to provide di N-alkyl heterocyclic diamines of the present invention.

It may be preferable to effect transformations of the $R_4$, $R_5$, and $R_6$ substituents of $R_3$, wherein $R_3$, $R_4$, $R_5$, and $R_6$ are as defined in formula I, after $R_3$ has been coupled to a diamine of general formula (1–11) from Scheme 1. As such, compounds of the present invention may be further transformed to other distinct compounds of the present invention. These transformations involve Stille, Suzuki, Heck, and Negishi coupling reactions all of which are well known to those skilled in the art of organic chemistry. Shown below in Schemes 4–6 are representative methods of such transformations of compounds of the present invention to other compounds of the present invention.

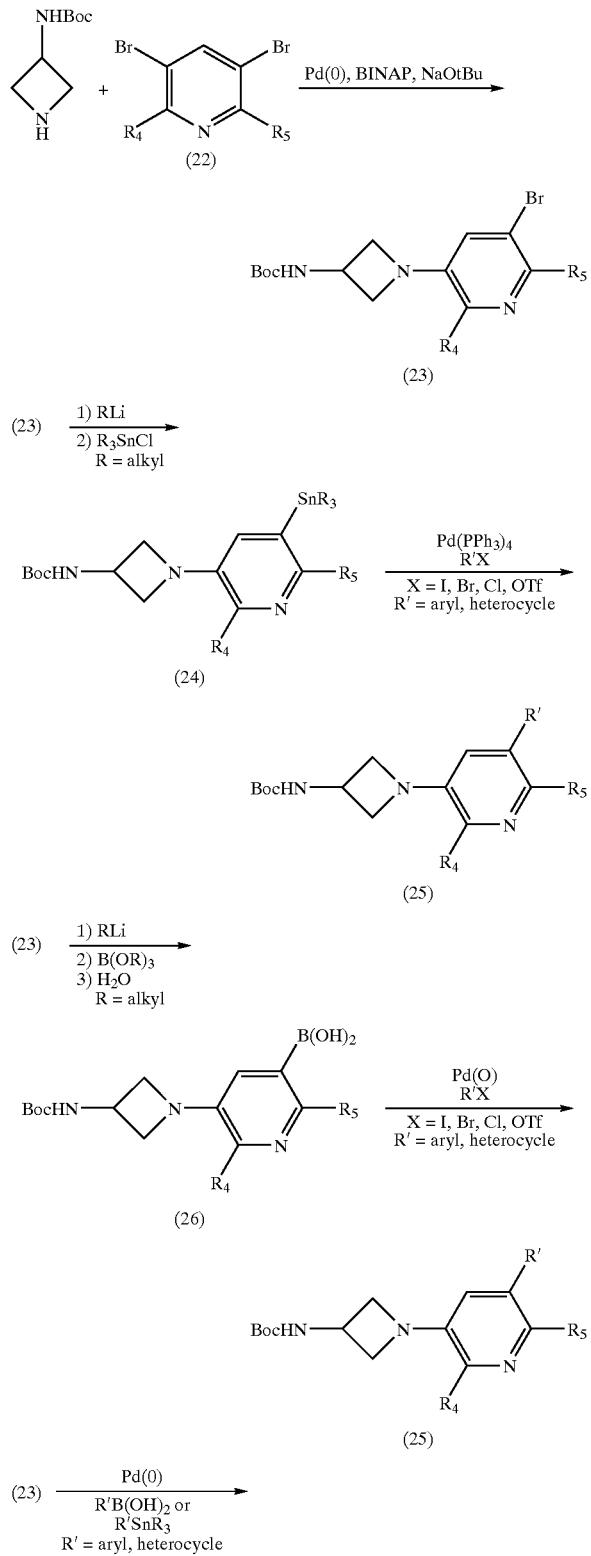

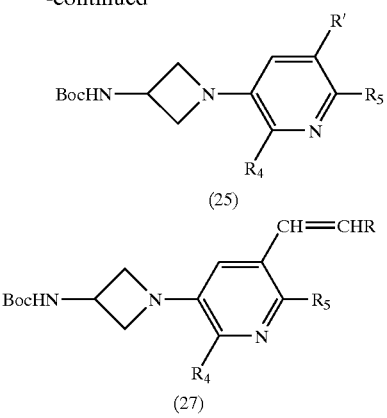

Compounds of general formula (23), (25), and (27), wherein $R_4$ and $R_5$ are as defined in formula I, R is alkyl, and R' is an aryl group or a heterocycle, can be prepared as described in Scheme 4. Diamines of general formula (1–11) from Scheme 1, wherein tert-butyl 3-azetidinylcarbamate shown in Scheme 4 is a representative mono protected diamine, can be treated with BINAP, a palladium catalyst, sodium tert-butoxide, and a dibromoheterocycle such as a compound of general formula (22), to provide bromides of general formula (23). Bromides of general formula (23) can be treated with an organolithium reagent and trialkyltin chloride to provide stannanes of general formula (24). Stannanes of general formula (24) can be treated with a palladium catalyst and an aryl or heterocyclic halide (or triflate) to provide compounds of general formula (25).

Bromides of general formula (23) can also be treated with an organolithium reagent, trialkoxy boranes, and water to provide boronic acids of general formula (26). Boronic acids of general formula (26) can be treated with a palladium catalyst and an aryl or heterocyclic halide (or triflate) to provide compounds of general formula (25).

Bromides of general formula (23) can also be treated with a palladium catalyst and aryl or heterocyclic boronic acids (or aryl or heterocyclic stannanes) to provide compounds of general formula (25).

Bromides of general formula (23) can also be treated with a palladium catalyst and alkenes or alkynes to provide compounds of general formula (27).

An alternate method for functionalizing heterocycles, defined as $R_3$ in formula I, that are coupled to diamines (1–11) from Scheme 1 involves ortho-directed metalation as described in (Gribble et al., Tetrahedron Lett. (1980) 21, 4137). The metalated species can be trapped with various electrophiles to afford intermediates which can be further elaborated as described in Schemes 4–6.

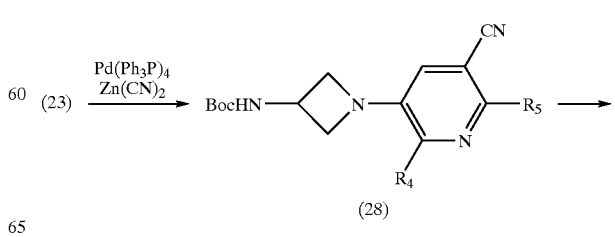

-continued

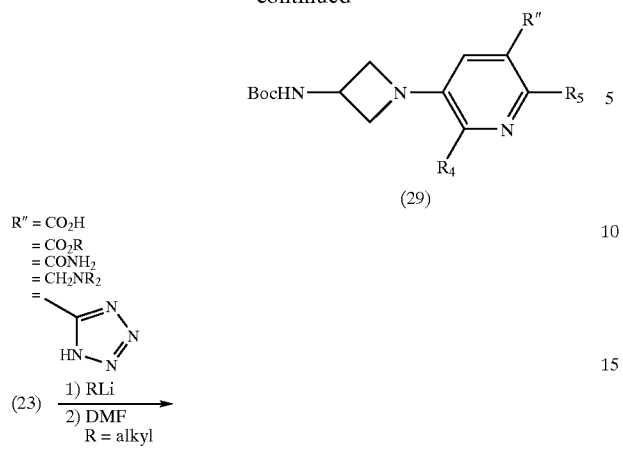

R" = CO₂H
= CO₂R
= CONH₂
= CH₂NR₂
=

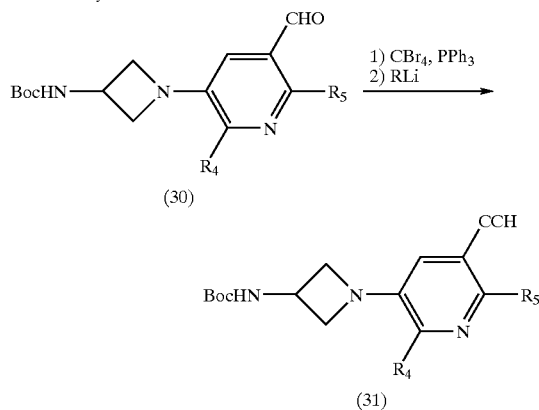

Bromides of general formula (23) from Scheme 4, can be further elaborated to nitriles of general formula (28). Nitriles of general formula (28) can be subjected to conditions well known to those skilled in the art of organic chemistry to provide carboxylic acids, esters, amides, and aminomethyl compounds of general formula (29). Aminomethyl compounds of general formula (29) can be treated with trimethylsilyl azide as described in (Wittenberger and Donner, JOC (1993) 58, 4139) to provide tetrazoles of general formula (29).

Bromides of general formula (23) from Scheme 4, can also be further elaborated to aldehydes of general formula (30). Aldehydes of general formula (30) can be treated with carbon tetrabromide, triphenylphosphine, and butyllithium as described in (Tetrahedron Lett. (1972) 3769–3772) to provide terminal alkynes of general formula (31). Aldehydes of general formula (30) can also be elaborated in ways well known to those skilled in the art of organic chemistry such as formation of oximes, hydrazones, olefins, and mono and disubstituted amino compounds. Grignard reagents can also be added to aldehydes of general formula (30) to provide secondary alcohols which can be oxidized to ketones.

Scheme 6

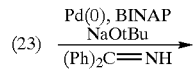

-continued

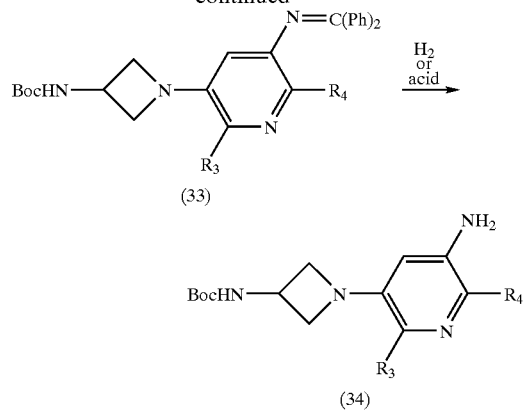

Bromides of general formula (23) from Scheme (4), can be treated with diphenylmethanimine and then treated with acid or treated with a palladium catalyst under a hydrogen atmosphere to provide amines of general formula (34). Amines of general formula (34) can be engaged in acylation, sulfonylation, and/or alkylation processes well known to those skilled in the art of organic chemistry. Combinations of alkylations, sufonylations, and acylations may be employed to prepare other compounds of the present invention.

Scheme 7

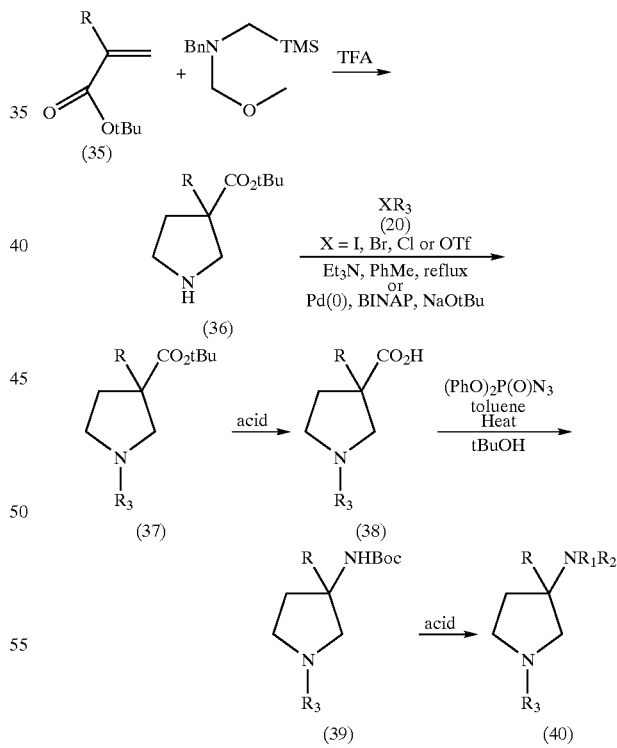

Pyrrolidines of general formula (40), wherein $R_1$, $R_2$, and $R_3$ are as defined in formula I and R is alkyl, can be prepared as described in Scheme 7. α,β-Unsaturated tert-butyl esters of general formula (35) can be treated with N-benzyl-N-(methoxymethyl)-N-[[(trimethylsilyl)methyl]amine in the presence of a catalytic amount of acid such as trifluoroacetic acid to provide pyrrolidines of general formula (36). Pyrrolidines of general formula (36) can be treated with heterocyclic halides (or triflates) of general formula (20), a base such as sodium tert-butoxide or triethylamine, a palladium catalyst, and BINAP to provide pyrrolidines of general formula (37). Pyrrolidines of general formula (37) can be treated with an acid such as trifluoroacetic acid and then treated with diphenylphosphoryl azide in toluene with heat followed by addition of tert-butanol to provide N-Boc pyrrolidines of general of formula (39). N-Boc pyrrolidines of general of formula (39) can be processed using standard conditions to provide amino or alkylamino or dialkylaminopyrrolidines of general formula (40).

Scheme 8

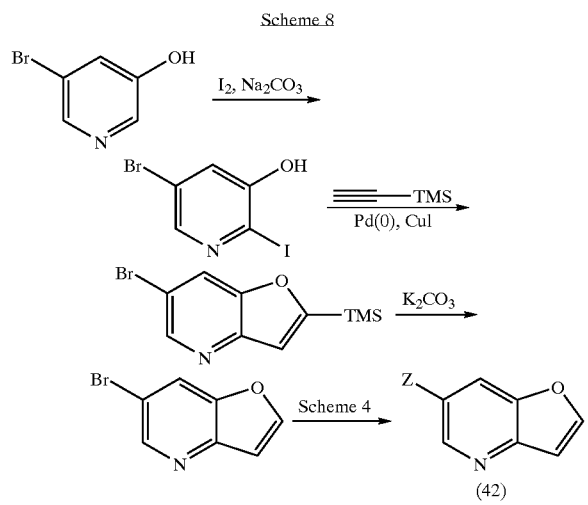

6-Substituted-furo[3,2-b]pyridines of general formula (42), wherein Z is as defined in formula I, can be prepared as described in Scheme 8. 5-Bromo-3-hydroxypyridine can be treated with iodine and a base such as sodium carbonate to provide 5-bromo-3-hydroxy-2-iodopyridine. 5-Bromo-3-hydroxy-2-iodopyridine can be treated with ethynyl (trimethyl)silane, a palladium catalyst and copper(I) iodide to provide 6-bromo-2 (trimethylsilyl)furo[3,2-b]pyridine. 6-Bbromo-2-(trimethylsilyl)furo[3,2-b]pyridine can be treated with a base such as potassium carbonate to provide 6-bromo-furo[3,2-b]pyridine. 6-Bromo-furo[3,2-b]pyridine can be processed as described in previous Schemes, in particular Scheme 4, to provide 6-substituted-furo[3,2-b]pyridines of general formula (42).

The compounds and processes of the present invention will be better understood in connection with the following Examples which are intended as an illustration of and not a limitation upon the scope of the invention.

EXAMPLE 1

N-[(3S)-1-(6-chloro-3-pyridinyl)pyrrolidinyl]-N-methylamine hydrochloride

EXAMPLE 1A tert-butyl (3S)-1-(6-chloro-3-pyridinyl) pyrrolidinylcarbamate tert-Butyl (3S)-pyrrolidinylcarbamate (1.86 g, 10 mmol; TCI) in toluene (100 mL) was heated to reflux under a Dean-Stark trap until 25 mL of solvent had been distilled. The solution was cooled to ambient temperature, and tris (dibenzylideneacetone)dipalladium (Pd$_2$(dba)$_3$, 0.92 g, 1 mmol; Alfa Aesar), 2,2'-bis(diphenylphosphino)-1,1'-binaphthyl (BINAP, 1.25 g, 2 mmol; Strem), 2-chloro-5-iodopyridine (2.39 g, 10 mmol; Aldrich), and sodium tert-butoxide (1.25 g, 13 mmol) were added in succession. The mixture was warmed to 70° C. under nitrogen until the reaction was complete (16 hours). The reaction mixture was diluted with ether (150 mL) and filtered through a plug of diatomaceous earth, with a diethyl ether rise. The filtrate was concentrated under reduced pressure, and the residue purified by chromatography on SiO$_2$ (ethyl acetate/hexanes, 25% to 100%) to provide the title compound (1.4 g, 47%). MS (CI/NH$_3$) m/z 298/300 (M+H)$^+$.

EXAMPLE 1B tert-butyl (3S)-1-(6-chloro-3-pyridinyl)pyrrolidinyl (methyl)carbamate The product from Example 1A (0.49 g, 1.6 mmol) in DMF (10 mL) was treated with NaH (60% dispersion, 0.069 g, 1.7 mmol) at −32 C. After 20 minutes, iodomethane (0.11 mL, 1.7 mmol) was added, and the mixture was allowed to warm to ambient temperature until the reaction was complete (2 hours). The reaction mixture was poured into ice water, and the solution was extracted with ethyl acetate. The extracts were washed with brine, dried (MgSO$_4$) and concentrated. The residue was passed through a short plug of silica gel with diethyl ether, and concentrated to provide the title compound as an oil (0.45 g, 88%). MS (CI/NH$_3$) m/z 312/314 (M+H)$^+$.

EXAMPLE 1C

N-[(3S)-1-(6-chloro-3-pyridinyl)pyrrolidinyl]-N-methylamine hydrochloride

The product from Example 1B (0.46 g, 1.47 mmol) in dichloromethane (5 mL) was cooled to 0° C. and treated with trifluoroacetic acid (2 mL) in dichloromethane (2 mL). The solution was allowed to warm to ambient temperature and stir for 4 hours. The volatiles were removed under reduced pressure, and the residue purified by chromatography on SiO$_2$ (dichloromethane/methanol/NH$_4$OH, 90:10:1). The free base was taken up in ethyl acetate and concentrated under reduced pressure to remove residual ammonia. The process was repeated twice more using toluene in place of ethyl acetate. Finally, the free base was taken up in ethanol-ethyl acetate (1:1) and treated with HCl (1M in ether, 1 equivalent). The precipitate was isolated by filtration and dried under reduced pressure to provide the title compound (0.364 g, 99%). mp>250° C.; $^1$H NMR (300 MHz, CD$_3$OD) δ 2.27 (m, 1H), 2.53 (m, 1H), 2.79 (s, 3H), 3.38 (td, J=9, 6 Hz, 1H), 3.53–3.68 (m, 3H), 3.97 (m, 1H), 7.14 (dd, J=9, 3 Hz, 1H), 7.27 (d, J=9 Hz, 1H), 7.75 (d, J=3 Hz, 1H); MS (CI/NH$_3$) m/z 212/214 (M+H)$^+$; 229/231 (M+NH$_4$)$^+$; Anal. Calcd for C$_{10}$H$_{14}$N$_3$Cl.HCl: C, 48.40; H, 6.09; N, 16.93. Found: C, 48.35; H, 5.97; N, 17.02.

EXAMPLE 2

(3S)-1-(6-chloro-3-pyridinyl)pyrrolidinylamine dihydrochloride

The product from Example 1A (0.90 g, 3.0 mmol) in 1,4-dioxane (10 mL) was cooled to 0° C. and treated with 4M HCl/1,4-dioxane (10 mL). The solution was allowed to warm to ambient temperature and stir for 8 hours. Ethyl acetate (100 mL) was added and the resulting mixture was stirred for 10 minutes, filtered, and the filtercake washed with excess ethyl acetate. The solid was recrystallized from ethanol/ethyl acetate to provide the title compound (0.73 g, 90%). mp>250° C.; $^1$H NMR (300 MHz, CD$_3$OD) δ 2.25 (m, 1H), 2.54 (s, 1H), 3.52 (m, 2H), 3.68 (m, 2H), 4.02 (m, 1H), 7.12 (dd, J=9, 3 Hz, 1H), 7.48 (d, J=9 Hz, 1H), 7.93 (d, J=3 Hz, 1H); MS (CI/NH$_3$: m/z 198/200 (M+H)$^+$, 215/217 (M+NH$_4$)$^+$; Anal. Calcd for C$_9$H$_{12}$ClN$_3$.2HCl: C, 39.95; H, 5.22; N, 15.53. Found: C, 39.89; H, 5.48; N, 15.27.

EXAMPLE 3

N-[(3S)-1-(6-chloro-3-pyridinyl)pyrrolidinyl]-N,N-dimethylamine 4-methylbenzenesulfonate The product from Example 2 (0.19 g, 0.96 mmol) in formic acid (4 mL) and 37% formaldehyde in water (7 mL) was warmed at 70° C. for 8 hours. The volatiles were removed under reduced pressure, and the residue was taken up in water (5 mL), poured into 5% sodium bicarbonate solution, and the solution was extracted with dichloromethane. The extracts were washed with brine, dried (MgSO$_4$) and concentrated under reduced pressure, and the residue purified by chromatography on deactivated SiO$_2$ [pretreated with ethyl acetate/hexane/diethylamine (50:48:2), eluting with ethyl acetate and then ethanol:dichloromethane (10:90)]. The free base was taken up in ethyl acetate and concentrated under reduced pressure to remove residual diethylamine. The process was repeated twice more using toluene in place of ethyl acetate. Finally, the free base was taken up in ethanol:ethyl acetate (1:1) and treated with p-toluenesulfonic acid monohydrate (0.118 g, 0.60 mmol). The precipitate was isolated by filtration and dried under reduced pressure to provide the title compound (0.152 g, 55%). mp 190–191.5° C.; $^1$H NMR (300 MHz, CD$_3$OD) δ 2.28 (m, 1H), 2.35 (s, 3H), 2.57 (m, 1H), 2.98 (s, 3H), 3.35 (m, 1H), 3.58 (m, 2H), 3.72 (m, 1H), 7.12 (dd, J=9, 3 Hz, 1H), 7.22 (d, J=7 Hz, 2H), 7.28 (d, J=9 Hz, 1H), 7.68 (d, J=7 Hz, 2H), 7.74 (d, J=3 Hz, 1H); MS (CI/NH$_3$): m/z 226/228 (M+H)$^+$, 243/245 (M+NH$_4$)$^+$; Anal. Calcd for C$_{11}$H$_{16}$ClN$_3$.C$_7$H$_8$O$_3$S: C, 54.33; H, 6.08; N, 10.56. Found: C, 54.01; H, 6.18; N, 10.41.

EXAMPLE 4

(3R)-1-(6-chloro-3-pyridinyl)pyrrolidinylamine 4-methylbenzenesulfonate

EXAMPLE 4A tert-butyl (3R)-1-(6-chloro-3-pyridinyl)pyrrolidinylcarbamate tert-Butyl (3R)-pyrrolidinylcarbamate (1.86 g, 10 mmol; TCI) and 2-chloro-5-iodopyridine (2.39 g, 10 mmol) were processed as described in Example 1A to provide the title compound (1.30 g, 44%). MS (CI/NH$_3$): m/z 298 (M+H)$^+$.

EXAMPLE 4B (3R)-1-(6-chloro-3-pyridinyl)pyrrolidinylamine 4-methylbenzenesulfonate The product from Example 4A (0.86 g, 2.9 mmol) in dichloromethane (4 mL) was cooled to 0° C. and treated with trifluoroacetic acid (3 mL) in dichloromethane (3 mL). The solution was allowed to warm to ambient temperature and stir for 4 hours. The volatiles were removed under reduced pressure and the residue purified by chromatography on SiO$_2$ (dichloromethane:methanol:NH$_4$OH 89:10:1). The free base was taken up in ethyl acetate and concentrated under reduced pressure to remove residual ammonia. The process was repeated twice more using toluene in place of in ethyl acetate. Finally, the free base was taken up in ethanol:ethyl acetate (1:1) and treated with p-toluenesulfonic acid monohydrate (1 equivalent). The precipitate was isolated by filtration and dried under reduced pressure to provide the title compound (0.13 g, 22%). mp 224.5–225.5° C.; $^1$H NMR (300 MHz, CD$_3$OD) δ 2.19 (m, 1H), 2.36 (s, 3H), 2.48 (m, 1H), 3.40 (m, 2H), 3.49 (m, 2H), 4.05, (m, 1H), 7.10 (dd, J=9, 3 Hz, 1H), 7.23 (d, J=7 Hz, 2H), 7.27 (d, J=9 Hz, 1H), 7.70 (m, 2H); MS (CI/NH$_3$) m/z 198/200 (M+H)$^+$, 215/217 (M+NH$_4$)$^+$; Anal. Calcd for C$_9$H$_{12}$ClN$_3$.C$_7$H$_8$O$_3$S: C, 51.96; H, 5.45; N, 11.36. Found: C, 51.97; H, 5.54; N, 11.21.

EXAMPLE 5

N-[(3R)-1-(6-chloro-3-pyridinyl)pyrrolidinyl]-N-methylamine hydrochloride

EXAMPLE 5A tert-butyl (3R)-1-(6-chloro-3-pyridinyl)pyrrolidinyl (methyl)carbamate The product from Example 4A (0.31 g, 1.0 mmol) in DMF (10 mL) was treated with NaH (60% dispersion, 0.060 g, 1.5 mmol) and iodomethane (0.065 mL, 1.05 mmol) according to the procedure of Example 1B to provide the title compound as an oil (0.31 g, 98%). MS (CI/NH$_3$) m/z 312/314.

EXAMPLE 5B

N-[(3R)-1-(6-chloro-3-pyridinyl)pyrrolidinyl]-N-methylamine hydrochloride

The product from Example 5A (0.31 g, 1.00 mmol) in 8 mL ethyl acetate:ethanol (1:1) was cooled to 0° C. and treated with 4M HCl/1,4-dioxane (4 mL). The solution was heated at reflux for 8 hours. The precipitate was isolated by filtration and the solid washed with excess ethyl acetate. The solid was recrystallized from ethanol/ethyl acetate and dried under reduced pressure to provide the title compound (0.14 g, 69%). mp 265° C. (dec); $^1$H NMR (300 MHz, CD$_3$OD) δ 2.28 (m, 1H), 2.54 (s, 3H), 2.80 (s, 3H), 3.38 (m, 2H), 3.60 (m, 2H), 3.98 (m, 1H), 7.14 (dd, J=9, 3 Hz, 1H), 7.28 (d, J=9 Hz, 1H), 7.75 (d, J=3 Hz, 1H); MS (CI/NH$_3$) m/z 212/214 (M+H)$^+$, 229/231 (M+NH$_4$)$^+$; Anal. Calcd for C$_{10}$H$_{14}$ClN$_3$.HCl: C, 48.40; H, 6.09; N, 16.93. Found: C, 48.28; H, 6.20; N, 16.83.

EXAMPLE 6

N-[(3R)-1-(6-chloro-3-pyridinyl)pyrrolidinyl]-N,N-dimethylamine 4-methylbenzenesulfonate The product from Example 4B (0.32, 1.6 mmol) in formic acid (6 mL) and 37% formaldehyde in water (10 mL) was converted to the title compound (0.13 g, 50%) according to the procedure of Example 3. $^1$H NMR (300 MHz, CD$_3$OD) δ 2.28 (m, 1H), 2.36 (s, 3H), 2.57 (m, 1H), 2.98 (s, 3H), 3.38 (m, 1H), 3.57 (m, 2H), 3.72 (m, 1H), 7.13 (dd, J=9, 3 Hz, 1H), 7.22 (d, J=7 Hz, 2H), 7.27 (d, J=9 Hz, 1H), 7.68 (d, J=7 Hz, 2H), 7.74 (d, J=3 Hz, 1H). MS (CI/NH$_3$): m/z 226/228 (M+H)$^+$, 243/245 (M+NH$_4$)$^+$; Anal. Calcd for C$_{11}$H$_{16}$ClN$_3$.C$_7$H$_8$O$_3$S 0.5 H$_2$O: C, 53.13; H, 6.19; N, 10.33. Found: C, 52.91; H, 6.21; N, 10.17.

EXAMPLE 7

1-(6-chloro-3-pyridinyl)-3-pyrrolidinylamine 4-methylbenzenesulfonate

EXAMPLE 7A tert-butyl 1-(6-chloro-3-pyridinyl)-3-pyrrolidinylcarbamate tert-Butyl 3-pyrrolidinylcarbamate (0.377 g, 2.03 mmol; TCI) and 2-chloro-5-iodopyridine (0.484 g, 2.03 mmol;

Aldrich) were processed according to the procedure of Example 1A to provide the title compound (0.29 g, 48%). MS (CI/NH$_3$) m/z 298/300 (M+H)$^+$.

EXAMPLE 7B 1-(6-chloro-3-pyridinyl)-3-pyrrolidinylamine 4-methylbenzenesulfonate The product from Example 7A (0.290 g, 0.976 mmol) in dichloromethane (5 mL) was treated with trifluoroacetic acid (5 mL). After stirring at ambient temperature for 18 hours, the reaction mixture was concentrated and the residue purified by chromatography on SiO$_2$ (dichloromethane:methanol:NH$_4$OH, 95:5:0.5 to 90:10:1) to provide the free base of the title compound as an oil (0.157 g, 82%). The free base in ethanol (2 mL) was treated with p-toluenesulfonic acid monohydrate (0.155 g, 0.816 mmol) and the resulting solid collected by filtration and recrystallized from ethanol to afford the title compound (0.132 g, 37%). $^1$H NMR (300 MHz, CD$_3$OD) δ 2.19 (m, 1H), 2.36 (s, 3H), 2.48 (m, 1H), 3.40 (m, 2H), 3.49 (m, 2H), 4.05, (m, 1H), 7.10 (dd, J=9, 3 Hz, 1H), 7.23 (d, J=7 Hz, 2H), 7.27 (d, J=9 Hz, 1H), 7.70 (m, 2H); MS (CI/NH$_3$) m/e 198/200, 215/217 (M+NH$_4$); Anal. Calcd for C$_9$H$_{12}$ClN$_3$·C$_7$H$_8$O$_3$S: C, 51.96; H, 5.45; N, 11.36. Found: C, 52.05; H, 5.64; N, 11.42.

EXAMPLE 8

(3S)-1-(3-pyridinyl)pyrrolidinylamine 4-methylbenzenesulfonate

The product from Example 2 (0.17 g, 0.86 mmol) in methanol (4 mL), and triethylamine (0.24 mL, 1.73 mmol) was treated with 10% Pd/C (0.01 g) and hydrogen (4 atm). After stirring for 12 hours at ambient temperature, the reaction mixture was filtered and the volatiles removed under reduced pressure. The free base was taken up in toluene and concentrated under reduced pressure to remove residual triethylamine. This process was repeated twice more. Finally, the free base was taken up in ethanol:ethyl acetate (1:1) and treated with p-toluenesulfonic acid monohydrate (0.0816 g, 0.43 mmol). The precipitate was isolated by filtration and dried under reduced pressure to provide the title compound (0.140 g, 71%). $^1$H NMR (300 MHz, CD$_3$OD) δ 2.20 (m, 1H), 2.36 (s, 3H), 2.51 (m, 1H), 3.42 (m, 1H), 3.60 (m, 2H), 4.07 (m, 1H), 7.12 (ddd, J=9, 3, 2 Hz, 1H), 7.23 (d, J=7 Hz, 2H), 7.29 (dd, J=9, 4 Hz, 1H), 7.70 (d, J=7 Hz, 2H), 7.90 (dd, J=4, 2 Hz, 2H), 7.95 (d, J=3 Hz, 1H); MS (CI/NH$_3$) m/z 164 (M+H)$^+$, 181 (M+NH$_4$)$^+$; Anal. Calcd for C$_9$H$_{13}$N$_3$·C$_7$H$_8$O$_3$S (0.25 H$_2$O): C, 56.53; H, 6.38; N, 12.36. Found: C, 56.68; H, 6.30; N, 12.11.

EXAMPLE 9

N-methyl-N-[(3S)-1-(3-pyridinyl)pyrrolidinyl]amine dihydrochloride

The product from Example 1C (0.15 g, 0.71 mmol) in methanol (4 mL), and triethylamine (0.20 mL, 1.44 mmol) was treated with 10% Pd/C (0.0112 g) and hydrogen (4 atm). The mixture was stirred for 8 hours at ambient temperature. The reaction mixture was filtered and the volatiles removed under reduced pressure. The free base was taken up in toluene and concentrated under reduced pressure to remove residual triethylamine. This process was repeated twice more. Finally, the free base was taken up in ethanol:ethyl acetate (1:1) and treated with HCl (1M in diethyl ether, 2 equiv). The precipitate was isolated by filtration and dried under reduced pressure to provide the title compound (0.120 mg, 91%). $^1$H NMR (300 MHz, CD$_3$OD) δ 2.38 (m, 1H), 2.59 (s, 1H), 2.81 (s, 3H), 3.55 (m, 1H), 3.70 (m, 2H), 3.83 (m, 1H), 4.08 (m, 1H), 7.81 (m, 2H), 8.08 (d, J=5 Hz, 1H), 8.14 (d, J=3 Hz, 1H); MS (CI/NH$_3$): m/z 178 (M+H)$^+$, 195 (M+NH$_4$)$^+$; Anal. Calcd for C$_{10}$H$_{15}$N$_3$·2HCl 1.5 H$_2$O: C, 43.33; H, 7.27; N, 15.16. Found: C, 43.12; H, 6.86; N, 14.92.

EXAMPLE 10

1-(3-pyridinyl)-3-pyrrolidinylamine bis(4-methylbenzenesulfonate)

EXAMPLE 10A tert-butyl 1-(3-pyridinyl)-3-pyrrolidinylcarbamate tert-Butyl 3-pyrrolidinylcarbamate (0.099 g, 0.53 mmol; TCI) and 3-bromopyridine (0.050 mL, 0.52 mmol; Aldrich) were processed according to the procedure of Example 1A to provide the title compound (0.092 g, 66%). MS (CI/NH$_3$) m/z 264 (M+H)$^+$.

EXAMPLE 10B 1-(3-pyridinyl)-3-pyrrolidinylamine bis(4-methylbenzenesulfonate)

The product from Example 10A (0.092 g, 0.30 mmol) was converted to the title compound (0.021 g, 14%) according to the procedure of Example 7B. $^1$H NMR (300 MHz, CD$_3$OD) δ 2.27 (m, 1H), 2.36 (s, 6H), 2.54 (m, 1H), 3.54 (m, 2H), 3.66 (m, 1H), 3.78 (m, 1H), 4.13 (m, 1H), 7.22 (d, J=8 Hz, 4H), 7.68 (d, J=8 Hz, 4H), 7.72 (m, 1H), 7.80 (dd, J=9, 5 Hz, 1H), 8.05 (d, J=5 Hz, 1H), 8.07 (d, J=3 Hz); MS (CI/NH$_3$) m/z 164 (M+H)$^+$; Anal. Calcd for C$_9$H$_{13}$N$_3$·2C$_7$H$_8$O$_3$S: C, 54.42; H, 5.76; N, 8.28. Found: C, 54.30; H, 5.76; N, 8.23.

EXAMPLE 11

(3R)-1-[5-(trifluoromethyl)-3-pyridinyl]pyrrolidinylamine dihydrochloride

EXAMPLE 11A tert-butyl (3R)-1-[5-(trifluoromethyl)-3-pyridinyl]pyrrolidinylcarbamate tert-Butyl (3R)-pyrrolidinylcarbamate (0.37 g, 2 mmol; TCI), 3-chloro-5-trifluoromethylpyridine (0.50 g, 2.8 mmol; Maybridge). 2-dicyclohexylphosphino-2'-dimethylamino-1,1'-biphenyl (CyMAP; 0.031 g, 0.08 mmol; Strem), and potassium phosphate (0.63 g, 3.0 mmol) were processed according to the procedure of Example 1A to provide the title compound (0.37 g, 56%). MS (CI/NH$_3$) m/z 332 (M+H)$^+$.

EXAMPLE 11B (3R)-1-[5-(trifluoromethyl)-3-pyridinyl]pyrrolidinylamine dihydrochloride The product from Example 11A (0.20 g, 0.60 mmol) in ethyl acetate:ethanol (6 mL, 1:1) was cooled to 0° C. and treated with 4M HCl/1,4-dioxane (0.6 mL) according to the procedure of Example 5B to provide the title compound (0.15 g, 85%). mp 234–235° C.; $^1$H NMR (300 MHz, CD$_3$OD) δ 2.30 (m, 1H), 2.57 (m, 1H), 3.62 (m, 2H), 3.75 (m, 1H), 3.88 (m, 1H), 4.16 (m, 1H), 7.90 (bs, 1H), 8.38 (d,

EXAMPLE 12

N-methyl-N-{(3R)-1-[5-(trifluoromethyl)-3-pyridinyl]pyrrolidinyl}amine hydrochloride

EXAMPLE 12A tert-butyl methyl {(3R)-1-[5-(trifluoromethyl)-3-pyridinyl]pyrrolidinyl}carbamate The product from Example 11A (0.26 g, 0.78 mmol) in DMF (10 mL) was treated with NaH (60% dispersion, 0.045 g, 1.5 mmol) and iodomethane (0.051 mL, 0.82 mmol) according to the procedure of Example 1B to provide the title compound as an oil (0.21 g, 98%).

EXAMPLE 12B

N-methyl-N-{(3R)-1-[5-(trifluoromethyl)-3-pyridinyl]pyrrolidinyl}amine hydrochloride The product from Example 12A (0.20 g, 0.60 mmol) in ethyl acetate:ethanol (6 mL, 1:1) was cooled to 0° C. and treated with 4M HCl/1,4-dioxane (0.6 mL) according to the procedure of Example 5B to provide the title compound (0.14 g, 69%). mp 265° C. (dec); $^1$H NMR (300 MHz, CD$_3$OD) δ 2.32 (m, 1H), 2.57 (m, 1H), 2.83 (s, 3H), 3.51 (m, 1H), 3.61–3.80 (m, 3H), 4.03 (m, 1H), 7.34 (bs, 1H), 8.23 (bs, 2H); MS (CI/NH$_3$) m/z 246 (M+H)$^+$; Anal. Calcd for $C_{10}H_{15}N_3$.HCl 0.25 H$_2$O: C, 46.16; H, 5.46; N, 14.68. Found C, 46.14; H, 5.37; N, 14.68.

EXAMPLE 13

(3S)-1-[5-(trifluoromethyl)-3-pyridinyl]pyrrolidinylamine dihydrochloride

EXAMPLE 13A tert-butyl (3S)-1-[5-(trifluoromethyl)-3-pyridinyl]pyrrolidinylcarbamate tert-Butyl (3S)pyrrolidinylcarbamate (0.37 g, 2 mmol; TCI), 3-chloro-5-trifluoromethylpyridine (0.50 g, 2.8 mmol; Maybridge), 2-dicyclohexylphosphino-2'-dimethylamino-1,1'-biphenyl (CyMAP; 0.031 g, 0.08 mmol; Strem), and potassium phosphate (0.63 g, 3.0 mmol) were processed according to the procedure of Example 1A to provide the title compound (0.47 g, 71%). MS (CI/NH$_3$) m/z 332 (M+H)$^+$.

EXAMPLE 13B (3S)-1-[5-(trifluoromethyl)-3-pyridinyl]pyrrolidinylamine dihydrochloride The product from Example 13A (0.22 g, 0.66 mmol) in ethyl acetate:ethanol (6 mL, 1:1) was cooled to 0° C. and treated with 4M HCl/1,4-dioxane (1.0 mL) according to the procedure of Example 5B to provide the title compound (0.13 g, 65%). mp 235–236° C.; $^1$H NMR (300 MHz, CD$_3$OD) δ 2.30 (m, 1H), 2.57 (m, 1H), 3.62 (m, 2H), 3.75 (m, 1H), 3.88 (m, 1H), 4.16 (m, 1H), 7.90 (bs, 1H), 8.38 (d, J=3 Hz, 1H), 8.48 (bs, 1H); MS (CI/NH$_3$) m/z 232 (M+H)$^+$, 249 (M+NH$_4$)$^+$; Anal. Calcd for $C_{10}H_{15}N_{32}$HCl: C, 39.49; H, 4.64; N, 13.82. Found: C, 39.41; H, 4.68; N, 13.56.

EXAMPLE 14

N-methyl-N-{(3S)-1-[5-(trifluoromethyl)-3-pyridinyl]pyrrolidinyl}amine hydrochloride

EXAMPLE 14A tert-butyl methyl {(3S)-1-[5-(trifluoromethyl)-3-pyridinyl]pyrrolidinyl}carbamate The product from Example 13A (0.46 g, 1.42 mmol) in DMF (10 mL) was treated with NaH (60% dispersion, 0.060 g, 1.5 mmol) and iodomethane (0.093 mL, 0.1.49 mmol) according to the procedure of Example 1B to provide the title compound as an oil (0.48 g, 77%).

EXAMPLE 14B

N-methyl-N-{(3S)-1-[5-(trifluoromethyl)-3-pyridinyl]pyrrolidinyl}amine hydrochloride The product from Example 14A (0.48 g, 1.39 mmol) in ethyl acetate:ethanol (10 mL, 1:1) was cooled to 0° C. and treated with 4M HCl/1,4-dioxane (3 mL) according to the procedure of Example 5B to provide the title compound (0.15 g, 65%). mp 240–243° C. (dec); $^1$H NMR (300 MHz, CD$_3$OD) δ 2.37 (m, 1H), 2.60 (m, 1H), 2.83 (s, 3H), 3.51 (m, 1H), 3.61–3.70 (m, 2H), 3.85 (m, 1H), 4.03 (m, 1H), 7.81 (bs, 1H), 8.36 (d, J=3 Hz, 1H), 8.42 (bs, 1H); MS (CI/NH$_3$) m/z 246 (M+H)$^+$, 263 (M+NH$_4$)$^+$; Anal. Calcd for $C_{10}H_{15}N_{31.75}$ HCl: C, 42.75; H, 5.14; N, 13.60. Found: C, 42.61; H, 5.21; N, 13.53.

EXAMPLE 15

(3R)-1-(6-chloro-5-methyl-3-pyridinyl)pyrrolidinylamine hydrochloride

EXAMPLE 15A tert-butyl (3R)-1-(6-chloro-5-methyl-3-pyridinyl)pyrrolidinylcarbamate tert-Butyl (3R)pyrrolidinylcarbamate (0.90 g, 4.8 mmol; TCI), 2-chloro-3-methyl-5-iodopyridine (1.22 g, 5.2 mmol), prepared as described in (U.S. Pat. No. 5,733,912), and Cs$_2$CO$_3$ (2.45 g, 13 mmol) were processed according to the procedure in Example 1A to provide the title compound as an oil (0.362 g, 24%). MS (CI/NH$_3$) m/z 312 (M+H)$^+$.

EXAMPLE 15B (3R)-1-(6-chloro-5-methyl-3-pyridinyl)pyrrolidinylamine hydrochloride The product from Example 15A (0.198 g 0.64 mmol) was converted to the title compound (0.122 g, 77%) according to the procedure in Example 1C. $^1$H NMR (300 MHz, CD$_3$OD) δ 2.27 (m, 1H), 2.37 (s, 1H), 2.53 (m, 1H), 3.40–3.46 (m, 2H), 3.55–3.67 (m, 2H), 4.08 (m, 1H), 7.17 (d, J=2 Hz, 1H), 7.63 (d, J=3 Hz, 1H); MS (CI/NH$_3$) m/z 212/214 (M+H)$^+$; Anal. Calcd for $C_{10}H_{14}N_3$Cl.HCl.H$_2$O: C, 44.79; H, 5.909; N, 15.67. Found: C, 44.97; H, 5.74; N, 15.32.

EXAMPLE 16

N-[(3R)-1-(6-chloro-5-methyl-3-pyridinyl)pyrrolidinyl]-N-methylamine dihydrochloride

EXAMPLE 16A tert-butyl (3R)-1-(6-chloro-5-methyl-3-pyridinyl)pyrrolidinyl(methyl)carbamate The product of Example 15A (0.230 g, 0.7 mmol) was converted to the title compound (0.193 g, 80%) according to the procedure in Example 1B. MS (CI/NH$_3$) m/Z 326/328 (M+H)$^+$.

EXAMPLE 16B

N-[(3R)-1-(6-chloro-5-methyl-3-pyridinyl)pyrrolidinyl]-N-methylamine dihydrochloride The product of Example 16A (0.186 g 0.6 mmol) was converted to the title compound (0.147 g, 98%) according to the procedure of Example 1C. $^1$H NMR (300 MHz, CD$_3$OD) δ 2.28 (m, 1H), 2.39 (s, 1H), 2.54 (m, 1H), 2.80 (s, 3H), 3.39 (m, 1H), 3.57–3.71 (m, 3H), 4.00 (m, 1H), 7.27 (d, J=2 Hz, 1H), 7.70 (d, J=3 Hz, 1H); MS (CI/NH$_3$) m/z 226/228 (M+H)$^+$; Anal. Calcd for C$_{11}$H$_{16}$N$_3$Cl.1.6HCl: C, 46.51; H, 6.25; N, 14.79. Found: C, 46.52; H, 5.86; N, 14.60.

EXAMPLE 17

(3S)-]-(6-chloro-5-methyl-3-pyridinyl)pyrrolidinylamine dihydrochloride

EXAMPLE 17A tert-butyl (3S)-1-(6-chloro-5-methyl-3-pyridinyl)pyrrolidinylcarbamate tert-Butyl (3S)-pyrrolidinylcarbamate (0.45 g, 2.4 mmol; TCI), tris(dibenzylideneacetone)dipalladium (Pd$_2$(dba)$_3$, 0.09 g, 0.1 mmol; Alfa Aesar), (R)-(+)-2-(diphenylphosphino)-2'-methoxy-1,1'-binaphthyl [(R)-MOP, 0.15 g, 3 mmol; Strem], 2-chloro-3-methyl-5-iodopyridine (0.562 g, 2.2 mmol), prepared as described in (U.S. Pat. No. 5,733,912), and Cs$_2$CO$_3$ (1.16 g, 0.36 mmol) in toluene (50 mL) were warmed at 80° C. under nitrogen for 8 hours. The reaction mixture was diluted with ethyl acetate (50 mL) and filtered through a plug of diatomaceous earth, with an ethyl acetate rinse. The filtrate was concentrated under reduced pressure and the residue purified by chromatography on SiO$_2$ (ethyl acetate/hexane, 10% to 30%) to provide the title compound (0.254 g, 35%). MS (CI/NH$_3$) m/z 312 (M+H)$^+$.

EXAMPLE 17B (3 S)-1-(6-chloro-5-methyl-3-pyridinyl)pyrrolidinylamine dihydrochloride The product from Example 17A (0.351 g 1.1 mmol) was converted to the title compound (0.309 g, 98%) according to the procedure in Example 1C. $^1$H NMR (300 MHz, CD$_3$OD) δ 2.25 (m, 1H), 2.45 (s, 1H), 2.53 (m, 1H), 3.46–3.57 (m, 2H), 3.60–3.77 (m, 2H), 4.12 (m, 1H), 7.52 (d, J=3 Hz, 1H), 7.82 (d, J=3 Hz, 1H); MS (CI/NH$_3$) m/z 212/214 (M+H)$^+$; Anal. Calcd for C$_{10}$H$_{14}$N$_3$Cl.2HCl: C, 42.20; H, 5.97; N, 14.76. Found: C, 42.37; H, 5.59; N, 14.54.

EXAMPLE 18

N-[(3S)-1-(6-chloro-5-methyl-3-pyridinyl)pyrrolidinyl]-N-methylamine dihydrochloride

EXAMPLE 18A tert-butyl (3S)-1-(6-chloro-5-methyl-3-pyridinyl)pyrrolidiny](methyl)carbamate The product from Example 17A (0.355 g 1.1 mmol) was converted to the title compound (0.268 g, 72%) according to the procedure in Example 1B. MS (CI/NH$_3$) m/z 326/328 (M+H)$^+$.

EXAMPLE 18B

N-[(3S)-1-(6-chloro-5-methyl-3-pyridinyl)pyrrolidinyl]-N-methylamine dihydrochloride The product from Example 18A (0.255 g, 0.8 mmol) was converted to the title compound (0.122 g, 77%) according to the procedure in Example 1C. $^1$H NMR (300 MHz, CD$_3$OD) δ 2.27 (m, 1H), 2.40 (s, 1H), 2.55 (m, 1H), 2.80 (s, 3H), 3.44 (m, 1H), 3.57–3.72 (m, 3H), 4.00 (m, 1H), 7.32 (d, J=3 Hz, 1H), 7.72 (d, J=3 Hz, 1H); MS (CI/NH$_3$) m/z 226/228 (M+H)$^+$; Anal. Calcd for C$_{11}$H$_{16}$N$_3$Cl.2.1HCl: C, 43.19; H, 6.00; N, 13.74. Found: C, 43.33; H, 6.02; N, 13.49.

EXAMPLE 19

(3S)-1-(5,6-dichloro-3-pyridinyl)pyrrolidinylamine dihydrochloride

EXAMPLE 19A tert-butyl (3S)-1-(5,6-dichloro-3-pyridinyl)pyrrolidinylcarbamate tert-Butyl (3S)pyrrolidinylcarbamate (0.23 g, 1.2 mmol; TCI) and 2,3-dichloro-5-iodopyridine (0.230 g, 1.0 mmol), prepared as described in (U.S. Pat. No. 5,733,912), were processed according to the procedure of Example 17A to provide the title compound (0.248 g, 68%). MS (CI/NH$_3$) m/z 332/334/336 (M+H)$^+$.

EXAMPLE 19B (3S)-1-(5,6-dichloro-3-pyridinyl)pyrrolidinylamine dihydrochloride The product from Example 19A (0.312 g, 0.94 mmol) was converted to the title compound (0.242 g, 96%) according to the procedure of Example 1C. $^1$H NMR (300 MHz, CD$_3$OD) δ 2.20 (m, 1H), 2.50 (m, 1H), 3.39–3.47 (m, 2H), 3.54–3.68 (m, 2H), 4.07 (m, 1H), 7.26 (d, J=3 Hz, 1H), 7.71 (d, J=3 Hz, 1H); MS (CI/NH$_3$) m/z 232/234 (M+H)$^+$, 249/251 (M+NH$_4$)$^+$; Anal. Calcd for C$_9$H$_{11}$N$_3$Cl$_2$.HCl.0.3H$_2$O: C, 39.46; H, 4.64; N, 15.34. Found: C, 39.70; H, 4.48; N, 14.98.

EXAMPLE 20

N-[(3S)-1-(5,6-dichloro-3-pyridinyl)pyrrolidinyl]-N-methylamine hydrochloride

EXAMPLE 20A tert-butyl (3R)-1-(5,6-dichloro-3-pyridinyl)pyrrolidinyl(methyl)carbamate The product from Example 19A (0.355 g 1.1 mmol) was converted to the title compound (0.268 g, 72%) according to the procedure in Example 1B. MS (CI/NH$_3$) m/z 326/328 (M+H)$^+$.

EXAMPLE 20B

N-[(3S)-1-(5,6-dichloro-3-pyridinyl)pyrrolidinyl]-N-methylamine hydrochloride

The product from Example 20A (0.201 g 0.6 mmol) was converted to the title compound (0.135 g, 81%) according to the procedure in Example 1C. $^1$H NMR (300 MHz, CD$_3$OD) δ 2.26 (m, 1H), 2.40 (s, 1H), 2.54 (m, 1H), 2.80 (s, 3H), 3.41 (r, 1H), 3.53–3.67 (m, 3H), 4.00 (m, 1H), 7.29 (d, J=3 Hz, 1H), 7.74 (d, J=3 Hz, 1H); MS (CI/NH$_3$) m/z 246/248 (M+H)$^+$, 263/267 (M+NH$_4$)$^+$; Anal. Calcd for C$_{10}$H$_{13}$N$_3$Cl$_2$.1HCl.0.1C$_2$H$_6$O: C, 42.66; H, 5.12; N, 14.65. Found: C, 42.76; H, 4.78; N, 14.37.

EXAMPLE 21

(3R)-1-(5,6-dichloro-3-pyridinyl)pyrrolidinylamine dihydrochloride

EXAMPLE 21A tert-butyl (3R)-1-(5,6-dichloro-3-pyridinyl)pyrrolidinylcarbamate tert-Butyl (3R)-pyrrolidinylcarbamate (0.43 g, 2.3 mmol; TCI) and 2,3-dichloro-5-iodopyridine (0.600 g, 2.2 mmol), prepared as described in (U.S. Pat. No. 5,733,912), were processed according to the procedure in Example 17A to provide the title compound (0.353 g, 52%). MS (CI/NH$_3$): m/z 332/334/336 (M+H)$^+$.

EXAMPLE 21B (3R)-1-(5,6-dichloro-3-pyridinyl)pyrrolidinylamine dihydrochloride The product from Example 21A (0.340 g 1.0 mmol) was converted to the title compound (0.187 g, 68%) according to the procedure in Example 1C. $^1$H NMR (300 MHz, CD$_3$OD) δ 2.20 (m, 1H), 2.51 (m, 1H), 3.39–3.47 (m, 2H), 3.54–3.69 (m, 2H), 4.07 (m, 1H), 7.25 (d, J=3 Hz, 1H), 7.71 (d, J=3 Hz, 1H); MS (CI/NH$_3$) m/z 232/234 (M+H); 249/251 (M+NH$_4$)$^+$; Anal. Calcd for ±4H$_{11}$N$_3$Cl$_2$HCl: C, 40.25; H, 4.50; N, 15.65. Found: C, 40.47; H, 4.63; N, 15.40.

EXAMPLE 22

N-[(3R)-1-(5,6-dichloro-3-pyridinyl)pyrrolidinyl]-N-methylamine hydrochloride

EXAMPLE 22A tert-butyl (3R)-1-(5,6-dichloro-3-pyridinyl) pyrrolidinyl(methyl)carbamate The product from Example 21A (0.500 g 1.5 mmol) was converted to the title compound (0.480 g, 92%) according to the procedure in Example 1B. MS (CI/NH$_3$) m/z 326/328 (M+H)$^+$.

EXAMPLE 22B

N-[(3R)-1-(5,6-dichloro-3-pyridinyl)pyrrolidinyl]-N-methylamine hydrochloride

The product from Example 22A (0.460 g 1.3 mmol) was converted to the title compound (0.278 g, 74%) according to the procedure in Example 1C. $^1$H NMR (300 MHz, CD$_3$OD) δ2.26 (m, 1H), 2.40 (s, 1H), 2.52 (m, 1H), 2.80 (s, 3H), 3.41 (m, 1H), 3.53–3.67 (m, 3H), 4.00 (m, 1H), 7.29 (d, J=3 Hz, 1H), 7.74 (d, J=3 Hz, 1H); MS (CI/NH$_3$) m/z 246/248 (M+H)$^+$, 263/267 (M+NH$_4$)$^+$; Anal. Calcd for C$_{10}$H$_{13}$N$_3$Cl$_2$.1HCl: C, 42.50; H, 4.99; N, 14.87. Found: C, 42.52; H. 4.76; N, 14.61.

EXAMPLE 23

(3S)-1-(6-chloro-5-methoxy-3-pyridinyl) pyrrolidinylamine dihydrochloride

EXAMPLE 23A 3-bromo-5-hydroxypyridine

3-Benzyloxy-5-bromopyridine (15.0 g, 56.8 mmol), prepared as described in (U.S. Pat. No. 5,733,912), and 30% HBr/acetic acid (200 mL) were stirred at ambient temperature for 16 hours. The reaction was diluted with diethyl ether (500 mL) and the resulting white solid (12.9 g) was isolated by filtration. The solid was taken up in methanol (300 mL) and concentrated NH$_4$OH (50 mL) was added. After stirring at ambient temperature for 12 hours, the mixture was concentrated under reduced pressure to provide the title compound as a white solid (9.8 g, 89%). MS (DCI/NH$_3$) m/z 174/176 (M+H)$^+$.

EXAMPLE 23B 5-bromo-2-chloro-3-hydroxypyridine

The product from Example 23A (9.8 g, 56.3 mmol) and NaOH (2.40 g, 100 mmol) in water (100 mL) were treated with aqueous NaOCl (35 mL of 10% solution). After stirring at ambient temperature for 16 hours, the mixture was quenched with acetic acid (5 ml) and then extracted with ethyl acetate (500 mL). The organic phase was dried (MgSO$_4$) and concentrated. The residue was purified on SiO$_2$ (dichloromethane:methanol, 97:3) to provide the title compound as a yellow solid (11.20 g, 96%). MS (DCI/NH$_3$) m/z 208/210 (M+H)$^+$.

EXAMPLE 23C 5-bromo-2-chloro-3-methoxypyridine

A suspension of NaH (0.181 g, 7.5 mmol) in dry DMF (30 mL) and diethyl ether (6 mL) was treated with the product from Example 23B (1.2 g, 5.8 mmol) in diethyl ether (5 mL). After stirring at ambient temperature for 30 minutes, the mixture was treated with a solution of iodomethane (1.06 g, 7.5 mmol) in diethyl ether (3 mL). After stirring for 30 minutes, the mixture was quenched with water (20 mL), extracted with diethyl ether (100 mL), dried (MgSO$_4$) and concentrated under reduced pressure. The crude was purified on SiO$_2$ (ethyl acetate:hexane, 1:4) to provide the title compound as a colorless oil (0.32 g, 25% provide). MS (CI/NH$_3$) m/z 222/224/226 (M+H)$^+$.

EXAMPLE 23D tert-butyl (3S)-1-(6-chloro-5-methoxy-3-pyridinyl) pyrrolidinylcarbamate tert-Butyl (3S)-pyrrolidinylcarbamate (0.45 g, 2.4 mmol; TCI) and the product from Example 23C were processed according to the procedure of Example 17A to provide the title compound (0.487 g, 72%). MS (CI/NH$_3$): m/z 328/330 (M+H)$^+$.

EXAMPLE 23E (3S)-1-(6-chloro-5-methoxy-3-pyridinyl) pyrrolidinylamine dihydrochloride The product of Example 23D (0.110 g, 0.34 mmol) was converted to the title compound (0.061 g, 69%) according to the procedure in Example 1C. $^1$H NMR (300 MHz, CD$_3$OD) δ 2.25 (m, 1H), 2.52 (m, 1H), 3.41–3.52 (m, 2H), 3.60–3.75 (m, 2H), 3.99 (s, 1H), 4.10 (m, 1H), 6.87 (d, J=3 Hz, 1H), 7.43 (d, J=3 Hz, 1H); MS (CI/NH$_3$) m/z 228/230 (M+H)$^+$; Anal. Calcd for C$_{10}$H$_{14}$N$_3$ClO.1.8HCl.0.4CH$_4$O: C, 40.80; H, 5.73; N, 13.73. Found: C, 40.83; H, 5.63; N, 13.41.

EXAMPLE 24

N-[(3S)-1-(6-chloro-5-methoxy-3-pyridinyl) pyrrolidinyl]-N-methylamine dihydrochloride

EXAMPLE 24A tert-butyl (3S)-1-(6-chloro-5-methoxy-3-pyridinyl) pyrrolidinyl(methyl)carbamate The product from Example 23D (0.340 g, 10.0 mmol) was converted to the title compound (0.311 g, 88%) according to the procedure in Example 1B. MS (CI/NH$_3$) m/z 342/344 (M+H)$^+$.

EXAMPLE 24B

N-[(3S)-1-(6-chloro-5-methoxy-3-pyridinyl) pyrrolidinyl]-N-methylamine dihydrochloride The product from Example 24A (0.295 g, 0.85 mmol) was converted to the title compound (0.188 g, 79%) according to the procedure in Example 1C. $^1$H NMR (300 MHz, CD$_3$OD) δ 2.30 (m, 1H), 2.55 (m, 1H), 2.81 (s, 3H), 3.44 (m, 1H), 3.58–3.74 (m, 3H), 3.97 (s, 1H), 4.01 (m, 1H), 6.85 (d, J=2 Hz, 1H), 7.41 (d, J=2 Hz, 1H); MS (CI/NH$_3$) m/z 242/244 (M+H)$^+$; Anal. Calcd for C$_{11}$H$_{16}$N$_3$ClO.1.7HCl: C, 43.50; H, 5.87; N, 13.84. Found: C, 43.71; H, 5.73; N, 13.61.

EXAMPLE 25

(3S)-1-(6-fluoro-5-methyl-3-pyridinyl) pyrrolidinylamine hydrochloride

EXAMPLE 25A tert-butyl (3S)-1-(6-fluoro-5-methyl-3-pyridinyl) pyrrolidinylcarbamate tert-Butyl (3S)-pyrrolidinylcarbamate (0.45 g, 2.4 mmol; TCI) and 2-fluoro-3-methyl-5-iodopyridine (0.525 g, 2.3 mmol), prepared as described in (U.S. Pat. No. 5,733,912), were processed according to the procedure of Example 17A to provide the title compound (0.258 g, 38%). MS (CI/NH$_3$) m/z 296 (M+H)$^+$.

EXAMPLE 25B (3S)-1-(6-fluoro-5-methyl-3-pyridinyl) pyrrolidinylamine hydrochloride The product from Example 25A (351 mg 1.1 mmol) was converted to the title compound (0.309 g, 98%) according to the procedure in Example 1C. $^1$H NMR (300 MHz, CD$_3$OD) δ 2.20 (m, 1H), 2.27 (s, 1H), 2.49 (m, 1H), 3.36–3.47 (m, 2H), 3.50–3.62 (m, 2H), 4.06 (m, 1H), 7.15 (dd, J=6, 3 Hz, 1H), 7.32 (t, J=3 Hz, 1H); MS (CI/NH$_3$) m/z 196 (M+H)$^+$, 213 (M+NH$_4$)$^+$; Anal. Calcd for C$_{10}$H$_{14}$N$_3$F.1.4HCl: C, 48.77; H, 6.30; N, 17.06. Found: C, 48.87; H, 6.09; N, 16.96.

EXAMPLE 26

N-[(3S)-1-(6-fluoro-5-methyl-3-pyridinyl) pyrrolidinyl]-N-methylamine dihydrochloride

EXAMPLE 26A tert-butyl (3S)-1-(6-fluoro-5-methyl-3-pyridinyl) pyrrolidinyl(methyl)carbamate The product from Example 25A (0.300 g, 1.0 mmol) was converted to the title compound (0.271 g, 86%) according to the procedure in Example 1B. MS (CI/NH$_3$) m/z 310 (M+H)$^+$.

EXAMPLE 26B

N-[(3S)-1-(6-fluoro-5-methyl-3-pyridinyl) pyrrolidinyl]-N-methylamine dihydrochloride The product from Example 26A (0.271 g 0.9 mmol) was converted to the title compound (0.131 g, 61%) according to the procedure in Example 1C. $^1$H NMR (300 MHz, CD$_3$OD) δ 2.25 (m, 1H), 2.26 (s, 1H), 2.52 (m, 1H), 2.79 (s, 3H), 3.44 (m, 1H), 3.52–3.62 (m, 3H), 3.96 (m, 1H), 7.16 (dd, J=8, 3 Hz, 1H), 7.34 (t, J=3 Hz, 1H); MS (CI/NH$_3$) m/z 210 (M+H)$^+$, 227 (M+NH$_4$)$^+$; Anal. Calcd for C$_{11}$H$_{16}$N$_3$F.1.6HCl: C, 49.37; H, 6.63; N, 15.70. Found: C, 49.61; H, 6.57; N, 15.65.

EXAMPLE 27

(3R)-1-(6-fluoro-5-methyl-3-pyridinyl) pyrrolidinylamine hydrochloride

EXAMPLE 27A tert-butyl (3R)-1-(6-fluoro-5-methyl-3-pyridinyl) pyrrolidinylcarbamate tert-Butyl (3R)-pyrrolidinylcarbamate (0.45 g, 2.4 mmol; TCI) and 2-fluoro-3-methyl-5-iodopyridine (0.525 g, 2.2 mmol), prepared as described in (U.S. Pat. No. 5,733,912), were processed according to the procedure in Example 17A to provide the title compound (0.257 g, 39%). MS (CI/NH$_3$) m/z 296 (M+H)$^+$.

EXAMPLE 27B (3R)-1-(6-fluoro-5-methyl-3-pyridinyl) pyrrolidinylamine hydrochloride The product from Example 27A (0.255 g, 0,9 mmol) was converted to the title compound (0.127 g, 63%) according to the procedure of Example 1C. $^1$H NMR (300 MHz, CD$_3$OD) δ 2.18 (m, 1H), 2.27 (s, 1H), 2.49 (m, 1H), 3.36–3.45 (m, 2H), 3.55–3.63 (m, 2H), 4.05 (m, 1H), 7.15 (dd, J=9, 3 Hz, 1H), 7.33 (t, J=2 Hz, 1H); MS (CI/NH$_3$) m/z 196 (M+H)$^+$, 213 (M+NH$_4$)$^+$; Anal. Calcd for C$_{10}$H$_{14}$N$_3$F.1HCl: C, 51.84; H, 6.53; N, 18.14. Found: C, 51.60; H, 6.28; N, 18.12.

EXAMPLE 28

N-[(3R)-1-(6-fluoro-5-methyl-3-pyridinyl) pyrrolidinyl]-N-methylamine dihydrochloride

EXAMPLE 28A tert-butyl (3R)-1-(6-fluoro-5-methyl-3-pyridinyl) pyrrolidiny](methyl)carbamate The product from Example 27A (0.300 g, 1.0 mmol) was converted to the title compound (0.203 g, 65%) according to the procedure in Example 1B. MS (CI/NH$_3$) m/z 310 (M+H)$^+$.

EXAMPLE 28B

N-[(3R)-1-(6-fluoro-5-methyl-3-pyridinyl) pyrrolidinyl]-N-methylamine dihydrochloride The product from Example 28A (0.271 g, 0.9 mmol) was converted to the title compound (0.131 g, 61%) according to the procedure in Example 1C. $^1$H NMR (300 MHz, CD$_3$OD) δ 2.24 (m, 1H), 2.26 (s, 1H), 2.52 (m, 1H), 2.79 (s, 3H), 3.44 (m, 1H), 3.52–3.62 (m, 3H), 3.96 (m, 1H), 7.18 (dd, J=6, 3 Hz, 1H), 7.34 (t J=2 Hz, 1H); MS (CI/NH$_3$) m/z 210 (M+H)$^+$, 227 (M+NH$_4$)$^+$; Anal. Calcd for C$_{11}$H$_{16}$N$_3$F.1.5HCl.0.1CH$_4$O: C, 49.90; H, 6.75; N, 15.73. Found: C, 49.99; H, 6.39; N, 15.47.

EXAMPLE 29

(3S)-1-(5-nitro-3-pyridinyl)pyrrolidinylamine fumarate

EXAMPLE 29A tert-butyl (3S)-1-(5-nitro-3-pyridinyl) pyrrolidinylcarbamate tert-Butyl (3S)pyrrolidinylcarbamate (0.44 g, 2.3 mmol; TCI), and 3-chloro-5-nitropyridine (0.40 g, 2.0 mmol), porepared as described in (Batkowski, Tadeusz. Rocz. Chem. (967) 41(4), 729–741) were processed according to the procedure of Example 1A to provide the title compound (0.60 g, 94%). MS (CI/NH$_3$) m/z 309 (M+H)$^+$.

EXAMPLE 29B (3S)-1-(5-nitro-3-pyridinyl)pyrrolidinylamine fumarate

The product from Example 29A (0.40 g, 1.3 mmol) in dichloromethane (6 mL) was treated with trifluoroacetic acid (2 mL) in dichloromethane (2 mL) according to the procedure of Example 1C. The free base was dissolved in methanol:diethyl ether (1:9) and treated with fumaric acid (1 equivalent in methanol:diethyl ether (1:9)). The precipitate was isolated by filtration and dried under reduced pressure to provide the title compound (0.25 g, 92%). mp 213–214° C.; $^1$H NMR (300 MHz, CD$_3$OD) δ 2.14 (m, 1H), 2.46 (m, 1H), 3.42 (m, 1H), 3.60–3.75 (m, 2H), 3.98 (m, 1H), 4.16 (m, 1H), 7.68 (t, J=3 Hz, 1H), 8.25 (d, J=3 Hz, 1H), 8.65 (d, J=3 Hz, 1H); MS (CI/NH$_3$) m/z 209 (M+H)$^+$, 226 (M+NH$_4$)$^+$; Anal. Calcd for C$_{10}$H$_{15}$N$_3$.C$_2$H$_2$O$_2$: C, 49.62; H, 5.30; N, 21.04. Found: C, 49.64; H, 5.27; N, 21.07.

EXAMPLE 30

N-methyl-N-[(3S)-1-(5-nitro-3-pyridinyl) pyrrolidinyl]amine fumarate

EXAMPLE 30A tert-butyl methyl [(3S)-1-(5-nitro-3-pyridinyl) pyrrolidinyl]carbamate The product from Example 29A (0.16 g, 0.52 mmol) in DMF (5 mL) was treated with NaH (60% suspension, 44 mg, 1.08 mmol) according to the procedure of Example 1B to provide the title compound (0.16 g, 95%). MS (CI/NH$_3$) m/z 323 (M+H)$^+$.

EXAMPLE 30B

N-methyl-N-[(3S)-1-(5-nitro-3-pyridinyl) pyrrolidinyl]amine fumarate

The product from Example 30A (0.16 g 0.50 mmol) in dichloromethane (4 mL) was processed according to the procedure of Example 29B to provide the title compound (0.10 g, 91%). mp 183–185° C.; $^1$H NMR (300 MHz, CD$_3$OD) δ 2.32 (m, 1H), 2.55 (m, 1H), 2.80 (s, 3H), 3.51 (m, 1H), 3.67 (m, 2H), 3.78 (m, 1H), 3.98 (m, 1H), 6.65 (s, 4H), 7.72 (t, J=3 Hz, 1H), 8.29 (d, J=3 Hz, 1H), 8.67 (d, J=3 Hz, 1H); MS (CI/NH$_3$) m/z 223 (M+H)$^+$, 240 (M+NH$_4$)$^+$; Anal. Calcd for C$_{10}$H$_{15}$N$_3$ C$_4$H$_4$O$_4$ 0.75H$_2$O: C, 47.79; H, 5.59; N, 15.92. Found: C, 47.47; H, 5.19; N, 15.76.

EXAMPLE 31

(3R)-1-(5-nitro-3-pyridinyl)pyrrolidinylamine fumarate

EXAMPLE 31A tert-butyl (3R)-1-(5-nitro-3-pyridinyl) pyrrolidinylcarbamate tert-Butyl (3R)-pyrrolidinylcarbamate (0.70 g, 3.75 mmol, TCI), and 3-chloro-5-nitropyridine (0.61 g, 3.0 mmol; Aldrich) were processed according to the procedure of Example 1A to provide the title compound (0.94 g, 97%). MS (CI/NH$_3$) m/z 309 (M+H)$^+$.

EXAMPLE 31B (3R)-1-(5-nitro-3-pyridinyl)pyrrolidinylamine fumarate

The product from Example 31A (0.42 g, 1.36 mmol) was processed according to the procedure of Example 29B to provide the title compound (0.26 g, 92%). mp 212–213° C.; $^1$H NMR (300 MHz, CD$_3$OD) δ 2.14 (m, 1H), 2.46 (m, 1H), 3.42 (m, 1H), 3.60–3.75 (m, 2H), 3.98 (m, 1H), 4.16 (m, 1H), 7.68 (t, J=3 Hz, 1H), 8.25 (d, J=3 Hz, 1H), 8.65 (d, J=3 Hz, 1H); MS (CI/NH$_3$): m/z 209 (M+H)$^+$, 226 (M+NH$_4$)$^+$; Anal. Calcd for C$_{10}$H$_{15}$N$_3$.C$_2$H$_2$O$_2$: C, 49.62; H, 5.30; N, 21.04. Found: C, 49.59; H, 5.22; N, 21.11.

EXAMPLE 32

N-methyl-N-[(3R)-1-(5-nitro-3-pyridinyl) pyrrolidinyl]amine fumarate

EXAMPLE 32A tert-butyl methyl[(3R)-1-(5-nitro-3-pyridinyl) pyrrolidinyl]carbamate The product from Example 31A (0.42 g, 1.36 mmol) in DMF (10 mL) was treated with NaH (60% suspension, 0.11 g, 2.72 mmol) according to the procedure of Example 1B to provide the title compound (0.45 g, 96%). MS (CI/NH$_3$): m/z 323 (M+H)$^+$.

EXAMPLE 32B

N-methyl-N-[(3R)-1-(5-nitro-3-pyridinyl) pyrrolidinyl]amine fumarate

The product from Example 32A (0.45 g, 1.4 mol) in dichloromethane (10 mL) was processed according to the procedure of Example 29B to provide the title compound (0.24 g, 78%). mp 184–185° C.; $^1$H NMR (300 MHz, CD$_3$OD) δ 2.32 (m, 1H), 2.54 (m, 1H), 2.79 (s, 3H), 3.51 (m, 1H), 3.67 (m, 2H), 3.78 (m, 1H), 3.98 (m, 1H), 6.64 (s, 4H), 7.71 (t, J=3 Hz, 1H), 8.29 (d, J=3 Hz, 1H), 8.68 (d, J=3 Hz, 1H); MS (CI/NH$_3$) m/z 223 (M+H)$^+$, 240 (M+NH$_4$)$^+$; Anal. Calcd for C$_{10}$H$_{15}$N$_3$.C$_4$H$_4$O$_4$: C, 49.70; H, 5.36; N, 16.59. Found: C, 49.55; H, 5.33; N, 16.60.

EXAMPLE 37

1-(6-chloro-3-pyridinyl)-4-piperidinylamine 4-methylbenzenesulfonate

EXAMPLE 37A tert-butyl 1-(6-chloro-3-pyridinyl)-4-piperidinylcarbamate tert-butyl 4-piperidinylcarbamate (0.30 g, 1.50 mmol; Astatech) and 2-chloro-5-iodopyridine (0.287 g, 1.50 mmol; Aldrich) were processed according to the procedure of Example 1A to provide the title compound as a yellow oil (0.202 g, 43%). (DCI/NH$_3$) m/Z 312 (M+H)$^+$.

EXAMPLE 37B 1-(6-chloro-3-pyridinyl)-4-piperidinylamine 4-methylbenzenesulfonate The product from Example 37A (0.60 mmol, 0.202 g) in ethanol (10 mL) was treated with 4N HCl in 1,4-dioxane (10 mL). After stirring for 1 hour at ambient temperature, the reaction mixture was concentrated under reduced pressure and the residue was purified by chromatography on SiO$_2$ (CH$_2$Cl$_2$:MeOH:NH$_4$OH, 90:10:1) to provide the free base of the title compound as a colorless oil (0.045 g, 36%). The obtained free base was treated with p-toluenesulfonic acid according to the procedure of Example 4B to provide the title compound. $^1$H NMR (CD$_3$OD, 300 MHz) δ 1.62–1.80 (m, 2H), 2.03–2.14 (m, 2H), 2.82–2.97 (m, 2H), 3.79–3.90

(m, 3H), 7.28 (d, J=10 Hz, 1H), 7.94 (dd, J=10, 3 Hz, 1H), 8.03 (d, J=3 Hz, 1H); MS (DCI/NH$_3$) m/z 212 (M+H)$^+$; Anal. Calcd for C$_{17}$H$_{22}$N$_3$O$_3$SCl: C, 53.19; H, 5.78; N, 10.95. Found C, 53.59; H, 5.75; N, 10.73.

EXAMPLE 38

1-(6-chloro-3-pyridinyl)-3-piperidinylamine 4-methylbenzenesulfonate

3-Piperidinylamine dihydrochloride (0.50 g, 2.90 mmol; Aldrich) and 2-chloro-5-iodopyridine (0.650 g, 2.90 mmol) were processed according to the procedure of Example 1A to provide the free base of the title compound as a yellow oil (9%, 0.054 g). The obtained free base was then treated with p-toluenesulfonic acid according to the procedure of Example 4B to provide the title compound as a gummy solid. $^1$H NMR (CD$_3$OD, 300 MHz) δ 1.20–1.35 (m, 1H), 1.60–1.78 (m, 1H), 1.80–1.91 (m, 1H), 1.93–2.04 (m, 1H), 2.60 (t, J=11 Hz, 1H), 2.65–2.78 (m, 1H), 2.94–3.05 (m, 1H), 3.34–3.45 (m, 1H), 3.48–3.58 (m, 1H), 7.25–7.30 (m, 2H), 8.01 (d, J=3 Hz, 1H); MS (DCI/NH$_3$) m/z 212.00 (M+H)$^+$.

EXAMPLE 39

(cis) 1-(6-chloro-3-pyridinyl)-4-methyl-3-piperidinylamine hydrochloride

EXAMPLE 39A

3-amino-4-methylpyridine

4-Methyl-3-nitropyridine (3.642 g, 26.37 mmol; Lancaster) in ethyl acetate (36 mL) was treated with 10% Pd/C (0.25 g) under a hydrogen atmosphere (60 psi) for 30 minutes. The catalyst was removed by filtration and the solution was concentrated to provide the title product as a white solid (2.92 g, 100%). MS (DCI/NH$_3$) m/z 109 (M+H)$^+$.

EXAMPLE 39B tert-butyl 4-methyl-3-pyridinylcarbamate

3-Amino-4-methylpyridine (2.9 g, 27 mmol) in anhydrous THF (50 mL) was cooled to 0° C. and treated with a solution of sodium hexamethyldisilazide (27 mL, 2M in THF; Fluka). The reaction mixture was stirred at ambient temperature for 5 minutes and then cooled again to 0° C. and treated with a solution of di-tert-butyl dicarbonate (5.4 g, 24.8 mmol; Aldrich) in THF. After stirring for 3 hours at ambient temperature, the residue was partitioned between ethyl acetate and 0.1N HCl. The aqueous phase was neutralized with sodium bicarbonate and reextracted with ethyl acetate. The combined organic phases were dried with sodium sulfate and the residue was purified by chromatography on SiO$_2$ (ethyl acetate/hexanes, 5% to 50%) to provide the title compound (3.6 g, 70%). MS (CI/NH$_3$) m/z 209 (M+H)$^+$.

EXAMPLE 39C tert-butyl (trans)-4-methyl-3-piperidinylcarbamate tert-butyl (cis)-4-methyl-3-piperidinylcarbamate

The product from Example 39B (3.59 g, 17.3 mmol) in methanol (50 mL) was treated with 5% Rh/C (3.74 g) under a hydrogen atmosphere (60 psi) at 50° C. for 25 hours. The reaction mixture was filtered to remove the catalyst and concentrated. The resulting residue was purified by chromatography on SiO$_2$ (dichloromethane:ethanol:NH$_4$OH, 95:5:0.5 to 90:10:1) to provide the pure cis isomer (2.76 g, 75%) and pure trans isomer (0.165 g, 4%). cis isomer (R$_f$ 0.46, dichloromethane:methanol:NH$_4$OH, 90:10:1); MS (CI/NH$_3$) m/z 214 (M+H)$^+$.

trans isomer (R$_f$ 0.25, dichloromethane:methanol:NH$_4$OH, 90:10:1); MS (CI/NH$_3$) m/z 214 (M+H)$^+$.

EXAMPLE 39D tert-butyl (cis)-1-(6-chloro-3-pyridinyl)-4-methyl-3-piperidinylcarbamate

The cis product from Example 39C (0.428 g, 2.00 mmol) and 2-chloro-5-iodopyridine (0.523 g, 2.19 mmol; Aldrich) were processed according to the procedure in Example 1A to provide the title compound (0.13 g, 20%). MS (CI/NH$_3$) m/z 326/328 (M+H)$^+$.

EXAMPLE 39E

(cis) 1-(6-chloro-3-pyridinyl)-4-methyl-3-piperidinylamine hydrochloride

The product from Example 39D (0.103 g, 0.317 mmol) was converted to the title compound according to the procedure of Example 1C (0.043 mg, 51%). $^1$H NMR (CD$_3$OD, 300 MHz) δ 1.10 (d, J=7 Hz, 3H), 1.75 (m, 2H), 2.03 (m, 1H), 2.84 (td, J=12, 4 Hz, 1H), 3.07 (dd, J=13, 2 Hz, 1H), 3.47 (m, 1H), 3.61 (m, 1H), 3.69 (m, 1H) 7.32 (d, J=9 Hz, 1H), 7.49 (dd, J=9, 3 Hz, 1H), 8.07 (d, J=3 Hz, 1H); MS (CI/NH$_3$) m/z 226/228 (M+H)$^+$; Anal. Calcd for C$_{11}$H$_{16}$ClN$_3$.HCl: C, 50.39; H, 6.54; N, 16.03. Found: C, 50.29; H, 6.52; N, 16.13.

EXAMPLE 40

(trans) 1-(6-chloro-3-pyridinyl)-4-methyl-3-piperidinylamine hydrochloride

EXAMPLE 40A tert-butyl (trans)-1-(6-chloro-3-pyridinyl)-4-methyl-3-piperidinylcarbamate The trans product from Example 39C (0.146 g, 0.68 mmol) and 2-chloro-5-iodopyridine (0.21 g, 0.88 mmol; Aldrich) were processed according to the procedure in Example 1A to provide the title compound (0.054 g, 24%). MS (CI/NH$_3$) m/z 326/328 (M+H)$^+$.

EXAMPLE 40B

(trans) 1-(6-chloro-3-pyridinyl)-4-methyl-3-piperidinylamine hydrochloride

The product from Example 40A (0.051 g, 0.157 mmol) was converted to the title compound according to the procedure of Example 1C (0.028 g, 68%). $^1$H NMR (CD$_3$OD, 300 MHz) δ 1.15 (d, J=7 Hz, 3H), 1.52 (tdd, J=14, 11, 4 Hz, 1H), 1.75 (m, 1H), 1.95 (dq, J=14, 3 Hz, 1H), 2.84 (dd, J=12, 10 Hz, 1H), 2.91 (td, J=11, 3 Hz, 1H), 3.06 (td, J=9, 4 Hz, 1H), 3.61 (m, 1H), 3.81 (dd, J=11, 3 Hz, 1H), 7.31 (d, J=9 Hz, 1H), 7.45 (dd, J=9, 3 Hz, 1H), 8.03 (d, J=3 Hz, 1H); Anal. Calcd for C$_{11}$H$_{16}$ClN$_3$.HCl: C, 50.39; H, 6.54; N, 16.03. Found: C, 50.22; H, 6.57; N, 15.87.

EXAMPLE 41

(3S) 1-(3-pyridinyl)piperidinylamine bis(4-methylbenzenesulfonate)

EXAMPLE 41A tert-butyl (3S)-2-oxopiperidinylcarbamate

A slow stream of HCl (gas) was bubbled through a solution of (L)-ornithine hydrochloride (20.2 g, 120 mmol;

Aldrich) in methanol (400 mL) for 45 minutes at ambient temperature. After stirring for an additional 4 hours, the mixture was concentrated under reduced pressure to leave a brown oil. The brown oil was dissolved in methanol (300 mL) and treated with a solution of NaOCH$_3$ (prepared from 6.9 g Na and 100 mL of methanol). After stirring at ambient temperature for 4 hours, the mixture was concentrated under reduced pressure to provide a brown semisolid. The semisolid was dissolved in dichloromethane (300 mL) and treated with triethylamine (50.1 g, 360 mmol) and di-tert-butyl dicarbonate (38.7 g, 180 mmol; Aldrich). After stirring for 60 hours at 20–25° C., the mixture was concentrated under reduced pressure. The residue was taken up in dichloromethane (200 mL), washed successively with water (100 mL) and brine (100 mL), dried (MgSO$_4$), and concentrated. The residue was purified by chromatography on silica gel (dichloromethane:methanol:NH$_4$OH, 95:5:0.5) to provide the title compound as a white solid (20.1 g, 78%). MS (CI/NH$_3$) m/z 215 (M+H)$^+$.

EXAMPLE 41B tert-butyl (3S)-piperidinylcarbamate

The product from Example 41A (20.1 g, 94 mmol) in THF (250 mL) was treated with borane-THF complex (162 mL, 1M in THF, 162 mmol; Aldrich) dropwise over 45 minutes at 0° C. After 1 hour, the cold bath was removed and the solution was stirred at 20–25° C. for 6 hours. The reaction mixture was quenched by cautious addition of methanol (100 mL) and 5% NaHCO$_3$ (300 mL). The mixture was stirred vigorously for 16 hours and then the volume was reduced under reduced pressure. The residue was treated with methanol (200 mL), warmed to reflux for 30 minutes, and concentrated under reduced pressure. This process was repeated twice more. The residue was suspended in 20% K$_2$CO$_3$ (200 mL) and extracted with diethyl ether (3×200 mL). The combined extracts were dried (MgSO$_4$) and concentrated under reduced pressure. The residue was purified by chromatography on silica gel (dichloromethane:methanol:NH$_4$OH, 90:10:1) to provide the title compound as a white solid an (5.64 g, 30%). MS (CI/NH$_3$) m/z 201 (M+H)$^+$.

EXAMPLE 41C tert-butyl (3S)-1-(3-pyridinyl)piperidinylcarbamate

The product from Example 41B (2.16 g, 10.8 mmol) in toluene (120 mL) was heated at reflux under a Dean-Stark trap until 30 mL of solvent had been distilled. The solution was cooled to ambient temperature and tris(dibenzylideneacetone)dipalladium (Pd$_2$(dba)$_3$, 0.198 g, 0.22 mmol; Alfa Aesar) and (dl)-2,2'-bis(diphenylphosphino)-1,1'-binaphthyl (BINAP, 0.27 g, 0.43 mmol; Strem) were added. The mixture was warmed to 85° C. under N$_2$ for 15 minutes and then cooled to ambient temperature. 3-Bromopyridine (2.05 g, 13 mmol; Aldrich), and K$_3$PO$_4$ (3.44 g, 16 mmol) were added in succession. The mixture was warmed to reflux under a nitrogen atmosphere. Three additional charges of catalyst (0.198 g of Pd$_2$(dba)$_3$ and 270 mg of BINAP) were added at 5–8 hour intervals. After 30 hours, the mixture was cooled to ambient temperature, diluted with ethyl acetate (200 mL) and filtered through a plug of diatomaceous earth. The filtrate was concentrated under reduced pressure and the residue purified by chromatography on silica gel (dichloromethane:methanol:NH$_4$OH, 90:10:1) to provide the title compound (0.382 g, 13%). MS (CI/NH$_3$) m/z 278 (M+H)$^+$.

EXAMPLE 41D (3S)-1-(3-pyridinyl)piperidinylamine bis(4-methylbenzenesulfonate)

The product from Example 41C (0.142 g, 0.51 mmol) and p-toluenesulfonic acid monohydrate (0.205 g, 1.1 mmol) in dichloromethane (10 mL) were refluxed for 16 hours. The precipitate was isolated by filtration and dried under reduced pressure to provide the title compound as a tan solid (0.267 g, 99%). mp 64–66° C.; $^1$H NMR (500 MHz, D$_2$O) δ 1.75 (m, 2H), 1.88 (m, 1H), 2.07 (m, 1H), 2.34 (s, 6H), 3.25 (m, 1H), 3.31 (dd, J=12, 7 Hz, 1H), 3.47 (m, 1H), 3.54 (m, 1H), 3.73 (dd, J=12, 3 Hz, 1H), 7.31 (d, J=7 Hz, 4H), 7.63 (d, J=7 Hz, 4H), 7.78 (dd, J=9, 5 Hz, 1H), 8.01 (dd, J=9, 3 Hz, 1H), 8.06 (d, J=5 Hz, 1H), 8.23 (d, J=3 Hz, 1H); MS (ESI+) m/z 178 (M+H)$^+$; Anal. Calcd for C$_{10}$H$_{15}$N$_3$.2.5C$_7$HsO$_3$S0.4H$_2$O: C, 53.72; H, 5.87; N, 6.85. Found: C, 53.84; H, 5.87; N, 6.55.

EXAMPLE 42

N-methyl-N-[(3S)-1-(3-pyridinyl)piperidinyl]amine bis(4-methylbenzenesulfonate)

EXAMPLE 42A tert-butyl (3S)-1-(trifluoroacetyl)piperidinylcarbamate

The product from Example 41B (1.39 g, 6.9 mmol) and triethylamine (0.91 g, 9 mmol) in THF (20 mL) were treated with rifluoroacetic anhydride (1.18 mL, 8.3 mmol) at 0° C. After s stirring at 20–25° C. for 2 hours, the mixture was concentrated under reduced pressure. The residue was dissolved in dichloromethane (100 mL) and the resulting solution was washed with saturated brine (30 mL), dried (MgSO$_4$), and concentrated under reduced pressure. The residue was purified by chromatography on silica gel (hexanes/ethyl acetate, 4:1) to provide the title compound as a light yellow solid (1.78 g, 87%). MS (CI/NH$_3$) m/z 314 (M+NH$_4$)$^+$.

EXAMPLE 42B tert-butyl methyl[(3S)piperidinyl]carbamate

The product from Example 42A (1.78 g, 6.0 mmol) in THF (30 mL) was treated with NaH (0.360 g of 60% dispersion, 9.0 mmol) at 0° C. After 20 minutes, the mixture was treated with methyl iodide (1.12 mL, 18 mmol) and the mixture was allowed to warm to ambient temperature. After stirring for 4 hours, methanol (5 mL) was slowly added and the resulting mixture was concentrated under reduced pressure. The residue was taken up in fresh methanol (50 mL) and 20% K$_2$CO$_3$ (5 mL) was added. After stirring at ambient temperature for 16 hours, the mixture was concentrated under reduced pressure. The residue was partitioned with dichloromethane (50 mL) and brine (20 mL). The organic phase was dried (MgSO$_4$) and concentrated under reduced pressure. The residue was purified by chromatography on silica gel (dichloromethane:methanol:NH$_4$OH, 95:5:0.5) to provide the title compound as a hygroscopic yellow solid (1.14 g, 93%). MS (CI/NH$_3$) m/z 215 (M+H)$^+$.

EXAMPLE 42C tert-butyl methyl [(3S)-1-(3-pyridinyl)piperidinyl]carbamate

The product from Example 42B (200 mg, 0.93 mmol) and 3-bromopyridine (182 mg, 1.15 mmol; Aldrich) were processed according to the procedure of Example 1A. The crude product was purified by chromatography on silica gel (hexanes:ethyl acetate, 3:2) to provide the title compound as a yellow oil (0.108 g, 40%). MS (CI/NH$_3$) m/z 292 (M+H)$^+$.

EXAMPLE 42D

N-methyl-N-[(3S)-1-(3-pyridinyl)piperidinyl]amine bis(4-methylbenzenesulfonate)

The product from Example 42C (0.103 g, 0.35 mmol) was treated with p-toluenesulfonic acid according to the procedure of Example 41D to provide the title compound as a light yellow solid (0.85 g, 45%). mp 89–91° C.; $^1$H NMR (300 MHz, D$_2$O) δ 1.72–1.95 (m, 3H), 2.14 (m, 1H), 2.47 (s, 6H), 2.78 (s, 3H), 3.29 (m, 1H), 3.43 (m, 3H), 3.76 (br d, J=9 Hz, 1H), 7.33 (d, J=7 Hz, 4H), 7.67 (d, J=7 Hz, 4H), 7.78 (dd, J=7, 4 Hz, 1H), 8.02 (dd, J=7, 2 Hz, 1H), 8.12 (br d, J=4 Hz, 1H), 8.28 (br s, 1H); MS (ESI+) m/z 192 (M+H)$^+$; Anal. Calcd for C$_{11}$H$_{17}$N$_3$.2.4C$_7$H$_8$O$_3$S.1.9H$_2$O: C, 52.29; H, 6.32; N, 6.60. Found: C, 52.69; H, 6.12; N, 6.18.

EXAMPLE 43

(3R)-1-(3-pyridinyl)piperidinylamine bis(4-methylbenzenesulfonate)

EXAMPLE 43A tert-butyl (3R)-2-oxopiperidinylcarbamate (D)-Ornithine hydrochloride (7.30 g, 43 mmol; Aldrich) was processed as described in Example 41A to provide the title compound (8.11 g, 87%). MS (CI/NH$_3$) m/z 215 (M+H)$^+$.

EXAMPLE 43B tert-butyl (3R)-piperidinylcarbamate

The product from Example 43A (8.11 g, 38 mmol) was processed as described in Example 41B to provide the title compound as a white solid (2.26 g, 25%). MS (CI/NH$_3$) m/z 201 (M+H)$^+$.

EXAMPLE 43C tert-butyl (3R)-1-(3-pyridinyl)piperidinylcarbamate

The product from Example 43B (1.12 g, 5.6 mmol) and 3-bromopyridine (1.07 g, 6.7 mmol; Aldrich) were processed according to the procedure of Example 41C to provide the title compound as an oil (0.068 g, 4%). MS (CI/NH$_3$) m/z 278 (M+H)$^+$.

EXAMPLE 43D (3R)-1-(3-pyridinyl)piperidinylamine bis(4-methylbenzenesulfonate)

The product from Example 43C (0.064 mg, 0.23 mmol) and p-toluenesulfonic acid monohydrate (0.088 g, 0.46 mmol) in dichloromethane (10 mL) was refluxed for 16 hours. The precipitate was filtered, washed with diethyl ether, and dried under reduced pressure to provide the title compound as a tan solid (0.060 g, 50%). $^1$H NMR (400 MHz, D$_2$O) δ 1.75 (m, 2H), 1.91 (m, 1H), 2.10 (m, 1H), 2.38 (s, 6H), 3.27 (m, 1H), 3.31 (dd, 3=12, 7 Hz, 1H), 3.49 (m, 1H), 3.56 (m, 1H), 3.73 (dd, J=12, 3 Hz, 1H), 7.34 (d, J=7 Hz, 4H), 7.66 (d, J=7 Hz, 4H), 7.79 (dd, (=9, 5 Hz, 1H), 8.02 (dd, g=9, 3 Hz, 1H), 8.08 (d, J=5 Hz, 1H), 8.25 (d, J=3 Hz, 1H); MS (ESI+) m/z 178 (M+H)$^+$; Anal. Calcd for C$_{10}$H$_{15}$N$_3$.2.0C$_7$H$_{803}$S2.5H$_2$O: C, 50.93; H, 6.40; N, 7.42. Found: C, 51.33; H, 6.03; N, 7.02.

EXAMPLE 44

N-methyl-N-[(3R)-1-(3-pyridinyl)piperidinyl]amine dihydrochloride

EXAMPLE 44A tert-butyl (3R)-1-(trifluoroacetyl) piperidinylcarbamate

The product from Example 43B (1.42 g, 7.1 mmol) was processed according to the procedure described in Example 42A to provide the title compound as a white solid (1.61 g, 77%). MS (CI/NH$_3$) m/z 314 (M+NH$_4$)$^+$.

EXAMPLE 44B tert-butyl methyl[(3R)-piperidinylcarbamate

The product from Example 44A (1.61 g, 5.4 mmol) was processed according to the procedure described in Example 42B to provide the title compound as a light yellow oil (0.768 g, 88%). MS (CI/NH$_3$) m/z 215 (M+H)$^+$.

EXAMPLE 44C tert-butyl (3R)-1-(6-chloro-3-pyridinyl)piperidinyl (methyl)carbamate The product from Example 44B (0.760 g, 3.55 mmol) and 2-chloro-5-iodopyridine (1.02 g, 4.26 mmol; Aldrich) were processed as described in Example 1A. The crude product was purified by chromatography on silica gel (hexanes:ethyl acetate, 4:1) to provide the title compound as a brown oil (0.821 g, 71%). MS (CI/NH$_3$) m/z 326/328 (M+H)$^+$.

EXAMPLE 44D tert-butyl methyl[(3R)-1-(3-pyridinyl)piperidinyl] carbamate

The product from Example 44C (0.560 g, 1.72 mmol) in methanol (5 mL) was treated with triethylamine (0.6 mL, 4.3 mmol) and 20% Pd(OH)$_2$/C (0.056 g). The mixture was stirred under H$_2$ (4 atm) at 50° C. for 30 minutes. The reaction mixture was filtered and the filtrate was concentrated. The residue was purified by chromatography on silica gel (hexanes:ethyl acetate, 3:1) to provide the title compound as a pale yellow oil (0.404 g, 81%). MS (CI/NH$_3$) m/z 292 (M+H)$^+$.

EXAMPLE 44E

N-methyl-N-[(3R)-1-(3-pyridinyl)piperidinyl]amine dihydrochloride

The product from Example 44D (0.396 g, 1.36 mmol) in diethyl ether (2 mL) was treated with HCl/diethyl ether (1M, 4.5 mL, 4.5 mmol). After stirring at 20–25° C. for 2 hours, the precipitate was filtered and dried under reduced pressure to provide the title compound as a light yellow solid (0.328 g, 92%). mp 79–81° C.; $^1$H NMR (400 MHz, D$_2$O) δ 1.72–1.95 (m, 3H), 2.10 (m, 1H), 2.73 (s, 3H), 3.33 (m, 1H), 3.45 (m, 3H), 3.74 (br d, J=8 Hz, 1H), 7.80 (dd, J=7, 4 Hz, 1H), 8.06 (dd, J=7, 2 Hz, 1H), 8.09 (d, J=4 Hz, 1H), 8.29 (d, J=3 Hz, 1H); MS (ESI+) m/z 192 (M+H)$^+$; Anal. Calcd for C$_{11}$H$_{17}$N$_{32}$HCl0.1H$_2$O: C, 49.67; H, 7.78; N; 12.65. Found: C, 49.69; H, 7.95; N, 12.93.

EXAMPLE 45

(3S)-1-(6-chloro-3-pyridinyl)piperidinylamine bis(4-methylbenzenesulfonate)

EXAMPLE 45A tert-butyl (3S)-1-(6-chloro-3-pyridinyl) piperidinylcarbamate

The product from Example 41B (1.0 g, 5.0 mmol) and 2-chloro-5-iodopyridine (1.43 g, 6.0 mmol; Aldrich) were processed according to the procedure described in Example 1A. The crude product was purified by chromatography on silica gel (hexanes:ethyl acetate, 4:1) to provide the title compound as a tan solid (0.070 g, 4.5%). MS (CI/NH$_3$) m/z 312/314 (M+H)$^+$.

EXAMPLE 45B (3S)-1-(6-chloro-3-pyridinyl)piperidinylamine bis(4-methylbenzenesulfonate)

The product from Example 45A (0.097 g, 0.31 mmol) and p-toluenesulfonic acid monohydrate (0.062 g, 0.33 mmol) in dichloromethane (8 mL) were refluxed for 16 hours. The precipitate was isolated by filtration and dried under reduced pressure to provide the title compound as a tan solid (0.064 g, 54%). mp 182–184° C.; $^1$H NMR (400 MHz, D$_2$O) δ 1.75 (m, 2H), 1.92 (m, 1H), 2.07 (m, 1H), 2.38 (s, 6H), 3.13 (m, 1H), 3.18 (dd, J=12, 7 Hz, 1H), 3.44 (m, 1H), 3.58 (m, 2H), 7.34 (d, J=7 Hz, 4H), 7.45 (d, J=9 Hz, 1H), 7.59 (dd, J=9, 3 Hz, 1H), 7.68 (d, J=7 Hz, 4H), 8.07 (d, J=3 Hz, 1H); MS (ESI+) m/z 212/214 (M+H)$^+$; Anal. Calcd for C$_{10}$H$_{14}$N$_3$Cl$_2$.7C$_7$H$_8$O$_3$S.1.6H$_2$O: C, 49.20; H, 5.54; N, 5.96. Found: C, 49.39; H, 5.57; N, 5.70.

EXAMPLE 46

N-[(3S)-1-(6-chloro-3-pyridinyl)piperidinyl]-N-methylamine dihydrochloride

The product from Example 42B (1.24 g, 5.8 mmol) and 2-chloro-5-iodopyridine (1.52 g, 6.4 mmol; Aldrich) were processed according to the procedure of Example 1A. The crude product was purified by chromatography on silica gel (hexanes:ethyl acetate, 4:1) to provide the title compound as a brown oil (0.629 g, 33%). MS (CI/NH$_3$) m/z 326/328 (M+H)$^+$.

EXAMPLE 46B

N-(3S)-1-(6-chloro-3-pyridinyl)piperidinyl]-N-methylamine dihydrochloride

The product from Example 46A (0.140 g, 0.43 mmol) was processed according to the procedure described in Example 44E to provide the title compound as a pale yellow solid (0.097 g, 76%). mp 120–122° C.; $^1$H NMR (500 MHz, D$_2$O) δ 1.82 (m, 2H), 1.93 (m, 1H), 2.07 (m, 1H), 2.79 (s, 3H), 3.25 (m, 1H), 3.37 (m, 2H), 3.47 (m, 1H), 3.66 (dd, J=12, 3 Hz, 1H), 7.56 (d, l=9 Hz, 1H), 7.75 (dd, J=9, 3 Hz, 1H), 8.14 (d, J=3 Hz, 1H); MS (ESI+) m/z 226/228 (M+H)$^+$; Anal. Calcd for C$_{11}$H$_{16}$N$_3$Cl.2HCl.0.1H$_2$O: C, 43.98; H, 6.11; N, 13.99. Found: C, 44.38; H, 6.16; N, 13.58.

EXAMPLE 47

(3R)-1-(6-chloro-3-pyridinyl)piperidinylamine bis (4-methylbenzenesulfonate)

EXAMPLE 47A tert-butyl (3R)-1-(6-chloro-3-pyridinyl) piperidinylcarbamate

The product from Example 43B (1.1 g, 5.5 mmol) and 2-chloro-5-iodopyridine (1.45 g, 6.0 mmol; Aldrich) were processed according to the procedure described in Example 41C. The crude product was purified by chromatography on silica gel (dichloromethane:methanol:NH$_4$OH, 90:10:1) to provide the title compound (0.075 g, 4.4%). MS (CI/NH$_3$) m/z 312/314 (M+H)$^+$.

EXAMPLE 47B (3R)-1-(6-chloro-3-pyridinyl)piperidinylamine bis (4-methylbenzenesulfonate)

The product from Example 47A (0.070 g, 0.22 mmol) in dichloromethane (4 mL) was treated with trifluoroacetic acid (1 mL). After stirring at 20–25° C. for 2 hours, the mixture was concentrated under reduced pressure. The residue was purified by chromatography on silica gel (dichloromethane:methanol:NH$_4$OH, 95:5:0.5) to provide the free base of the title compound as a light yellow oil (0.020 g, 0.096 mol). The resultant free base was combined with p-toluenesulfonic acid monohydrate (0.038 g, 0.199 mmol) in ethyl acetate/diethyl ether to provide the title compound as a yellow solid (0.020 g, 34%). $^1$H NMR (400 MHz, D$_2$O) δ 1.74 (m, 2H), 1.91 (m, 1H), 2.07 (m, 1H), 2.38 (s, 6H), 3.13 (m, 2H), 3.33 (m, 1H), 3.58 (m, 2H), 7.34 (d, J=7 Hz, 4H), 7.42 (d, J=9 Hz, 1H), 7.56 (dd, J=9, 3 Hz, 1H), 7.68 (d, J=7 Hz, 4H), 8.06 (d, J=3 Hz, 1H); MS (ESI+) m/z 212/214 (M+H)$^+$; Anal. Calcd for C$_{10}$H$_{14}$N$_3$Cl.2.4C$_7$H$_8$O$_3$S.1.5H$_2$O: C, 49.37; H, 5.60; N, 6.44. Found: C, 49.43; H, 5.59; N, 6.38.

EXAMPLE 48

N-[(3R)-1-(6-chloro-3-pyridinyl)piperidinyl]-N-methylamine dihydrochloride

The product from Example 44C (0.252 g, 0.77 mmol) in diethyl ether (3 mL) was treated with HCl/diethyl ether (1 M, 2.3 mL, 2.3 mmol). The mixture was agitated in an ultrasonic bath for 1 hour and then concentrated under reduced pressure. The residual solid was triturated with diethyl ether (20 mL) and dried under reduced pressure to provide the title compound as a yellow solid (0.110 g, 43%). mp 103–105° C.; $^1$H NMR (400 MHz, D$_2$O) δ 1.79 (m, 2H), 1.89 (m, 1H), 2.10 (m, 1H), 2.78 (s, 3H), 3.21 (m, 1H), 3.30 (m, 2H), 3.45 (m, 1H), 3.60 (dd, J=12, 3 Hz, 1H), 7.47 (d, J=9 Hz, 1H), 7.63 (dd, J=9, 3 Hz, 1H), 8.10 (d, J=3 Hz, 1H); MS (ESI+) m/z 226/228 (M+H)$^+$; Anal. Calcd for C$_{11}$H$_{16}$N$_3$Cl.1.7HCl.0.4H$_2$O: C, 44.80; H, 6.32; N, 12.25. Found: C, 44.72; H, 6.58; N, 12.35.

EXAMPLE 49

N-[(3S)-1-(6-chloro-5-methyl-3-pyridinyl) piperidinyl]-N-methylamine hydrochloride

EXAMPLE 49A 5-bromo-2-hydroxy-3-methylpyridine

Sodium nitrite (5.0 g, 72.5 mmol) in water (10 mL) was added dropwise to a cooled (0° C.) mixture of 2-amino-5-bromo-3-methylpyridine (5.0 g, 26.7 mmol; Lancaster) in 2:6 M sulfuric acid (70 mL). The mixture was allowed to warm to ambient temperature, stir for 1.5 hours, filtered, and the filtercake was washed with cold water and air dried. The precipitate was dissolved in dichloromethane (100 mL), dried (MgSO$_4$), and concentrated to provide the title compound as a solid (4.2 g, 84%). MS (DCI/NH$_3$) m/z 348 (M+H)$^+$.

EXAMPLE 49B

5-bromo-2-chloro-3-methylpyridine

The product from Example 49A (4.1 g, 221.8 mmol) in DMF (40 mL) was treated with phosphorous oxychloride (10 g, 65.4 mmol) dropwise at 0° C. The resulting solution was heated at 120° C. for 2 hours, cooled and poured onto ice/$H_2O$. The mixture was made basic with $NH_4OH$. The precipitate was filtered, washed with ice water, dissolved in dichloromethane (100 mL), washed with brine, and dried ($MgSO_4$). The solution was filtered through a pad of silica (dichloromethane) and concentrated to leave the title compound as a white solid (3.48 g, 78%). MS ($DCI/NH_3$) m/z 348 $(M+H)^+$.

EXAMPLE 49C tert-butyl (3S)-1-(6-chloro-5-methyl-3-pyridinyl) piperidinyl(methyl)carbamate The product from Example 42B (0.518 g, 2.4 mmol) and the product from Example 49B (0.500 g, 2.4 mmol) were processed according to the procedure escribed in Example 1A. The crude product was purified by chromatography on silica gel (hexanes:ethyl acetate, 4:1) to provide the title compound as a brown oil (0.252 g, 31%). MS ($CI/NH_3$) m/z 340/342 $(M+H)^+$.

EXAMPLE 49D

N-[(3S)-1-(6-chloro-5-methyl-3-pyridinyl) piperidinyl]-N-methylamine hydrochloride The product from Example 49C (0.245 g, 0.72 mmol) in dichloromethane (4 mL) was treated with trifluoroacetic acid (2 mL). After stirring at 20–25° C. for 12 hours, the mixture was concentrated under reduced pressure. The residue was purified by chromatography on silica gel (dichloromethane:methane:$NH_4OH$, 95:5:0.5) to provide the free base of the title compound as a brown oil (0.154 g). The resultant free base was dissolved in diethyl ether (2 mL) and treated with HCl/diethyl ether (1 M, 5 mL). The mixture was concentrated and the residual solid was triturated with diethyl ether (10 mL) and dried under reduced pressure to provide the title compound as an off white solid (0.150 g, 67%). mp 75–77° C.; $^1$H NMR (400 MHz, $D_2O$) δ 1.80 (m, 2H), 1.92 (m, 1H), 2.13 (m, 1H), 2.37 (s, 3H), 2.79 (s, 3H), 3.21 (m, 1H), 3.32 (m, 2H), 3.46 (m, 1H), 3.63 (dd, J=12, 3 Hz, 1H), 7.63 (d, J=2 Hz, 1H), 8.00 (br s, 1H); MS (ESI+) m/z 240/242 $(M+H)^+$; Anal. Calcd for $C_{12}H_{18}N_3Cl·HCl·0.3H_2O$: C, 45.31; H, 6.53; N, 13.21. Found: C, 45.31; H, 6.86; N, 12.86.

EXAMPLE 50

1-(6-chloro-3-pyridinyl)-3-azetidinylamine 4-methylbenzenesulfonate

EXAMPLE 50A tert-butyl 1-(6-chloro-3-pyridinyl)-3-azetidinylcarbamate tert-Butyl 3-azetidinylcarbamate (0.70 g, 4.0 mmol) and 2-chloro-5-iodopyridine (1.46 g, 6.0 mmol; Aldrich) were processed according to the procedure described in Example 1A to provide the title compound (0.53 g, 47%). MS ($CI/NH_3$) m/z 284/286.

EXAMPLE 50B

1-(6-chloro-3-pyridinyl)-3-azetidinylamine 4-methylbenzenesulfonate

The product from Example 50A (0.26 g, 0.90 mmol) in dichloromethane (4 mL) was cooled to 0° C. and treated with trifluoroacetic acid (1 mL) in dichloromethane (1 mL). The solution was allowed to warm to ambient temperature and stir for 4 hours. The volatiles were removed under reduced pressure and the residue purified by chromatography on $SiO_2$ (dichloromethane:methanol:$NH_4OH$, 89:10:1). The free base was taken up and concentrated under reduced pressure to remove residual ammonia. The process was repeated twice more using toluene in place of in ethyl acetate. Finally, the free base was taken up in ethanol:ethyl acetate (1:1) and treated with p-toluenesulfonic acid monohydrate (0.10 g, 0.53 mmol). The precipitate was isolated by filtration and dried under reduced pressure to provide the title compound (0.180 g, 65%). mp 194–195.5° C.; $^1$H NMR (300 MHz, $CD_3OD$) δ 2.36 (s, 3H), 3.93 (m, 2H), 4.24 (m, 3H), 6.98 (dd, J=9, 3 Hz, 1H), 7.23 (d, J=7 Hz, 3H), 7.27 (d, J=9 Hz, 1H), 7.59 (d. J=3 Hz, 1H), 7.68 (d, J=7 Hz, 2H); MS ($CI/NH_3$) m/z 184/186 $(M+H)^+$, 201/203 $(M+NH_4)^+$; Anal. Calcd for $C_9H_{10}ClN_3·C_7H_8O_3S$: C, 50.63; H, 5.10; N, 11.81. Found: C. 50.65; H, 5.18; N, 11.65.

EXAMPLE 51

(2S,3R)-2-(chloromethyl)-1-(3-pyridinyl) pyrrolidinylamine dihydrochloride

EXAMPLE 51A

(2S,3S)-1-(tert-butoxycarbonyl)-3-hydroxy-2-pyrrolidinecarboxylic acid trans-3-Hydroxy-(L)-proline (10.0 g, 76.3 mmol) in THF (50 mL) was treated with sodium hydroxide (3.36 g, 84 mmol) in $H_2O$ (34 mL) and then treated with di-tert-butyl dicarbonate (16.63 g, 76.3 mmol) portionwise. After stirring at ambient temperature for 10 hours, the mixture was concentrated under reduced pressure to remove the THF. The residue was acidified to pH 2–3 with saturated $KHSO_4$, and extracted with ethyl acetate (2×200 mL). The organic extracts were combined, washed with brine (2×30 mL) and concentrated to provide the title compound as a white solid (12.3 g, 70%). mp 156–157° C.

EXAMPLE 51B tert-butyl (2R,3 S)-3-hydroxy-2-(hydroxymethyl)-1-pyrrolidinecarboxylate

The product from Example 51A (7.73 g, 33.5 mmol) in dry THF (100 mL) was treated with borane-methyl sulfide complex (10 M in THF, 7.4 mL, 74 mmol) dropwise over 10 minutes. The solution was refluxed for 1 hour, cooled to 10–20° C., and methanol was added cautiously until there was no obvious evolution of hydrogen. The mixture was concentrated under reduced pressure and the white residue was stirred with water (50 mL) for 10 minutes and then extracted with ethyl acetate (3×100 mL). The extracts were combined, washed with brine (2×10 mL), dried ($Na_2SO_4$), and concentrated to provide the title compound as a white solid (7.24 g, 99%). MS ($DCI/NH_3$) m/z 218 $(M+H)^+$.

EXAMPLE 51C tert-butyl (2R,3S)-3-[(methylsulfonyl)oxy]-2-{[(methylsulfonyl)oxy]methyl}-1-pyrrolidinecarboxylate The product from Example 51B (4.6 g, 21.2 mmol) and triethylamine (9.0 g, 89.0 mmol) in dichloromethane (100 mL) were treated with methanesulfonyl chloride (4.9 mL, 63.5 mmol) over 20 minutes at 0° C. After stirring at ambient temperature for 16 hours, the mixture was quenched with saturated sodium bicarbonate (50 mL) and extracted with dichloromethane (2×100 mL). The combined extracts were washed with brine (2×10 mL), dried ($Na_2SO_4$), and concentrated. The residual brown oil was purified by chromatography ($SiO_2$, hexanes:ethyl acetate, 3:2) to provide the title compound as a pale yellow solid (4.6 g, 58%). MS (DCI/$NH_3$) m/z 391 $(M+NH_4)^+$, 374 $(M+H)^+$.

EXAMPLE 51D tert-butyl (1R,5R)-6-benzyl-2,6-diazabicyclo[3.2.0]heptane-2-carboxylate The product from Example 51C (4.5 g, 12 mmol) in anhydrous toluene (100 mL) was treated with benzylamine (7.7 g, 36 mmol) and the solution was refluxed for 20 hours. The mixture was cooled to 25° C. and filtered. The filtrate was concentrated and the residue purified by chromatography ($SiO_2$, hexanes:ethyl acetate, 2:3) to provide the title compound as a white solid (2.4 g, 70%). MS (DCI/$NH_3$) m/z 289 $(M+H)^+$.

EXAMPLE 51E (1R,5R)-6-benzyl-2,6-diazabicyclo[3.2.0]heptane

The product from Example 51D (1.00 g, 3.4 mmol) in ethanol (10 mL) was treated with concentrated HCl (1 mL). The mixture was heated at 50° C. for 1 hour, cooled and concentrated under reduced pressure. The residue was taken up in isopropyl acetate and concentrated to remove ethanol and water. The title compound was purified by recrystallization from i-isopropyl acetate/heptane (1:1) to provide a white solid (0.74 g, 84%). MS (DCI/$NH_3$) m/z 189 $(M+H)^+$.

EXAMPLE 51F (1R,5R)-6-benzyl-2-(6-chloro-3-pyridinyl)-2,6-diazabicyclo[3.2.0]heptane The product from Example 51 E (0.26 g, 1.0 mmol) and 2-chloro-5-iodopyridine were processed according to the procedure described in Example 1A, except that a larger amount of sodium tert-butoxide (0.384 g, 4.0 mmol) was used. The crude product was purified by chromatography on $SiO_2$ (dichloromethane:methanol, 95:5) to provide the title compound (0.25 g, 84%). MS (DCI/$NH_3$) m/z 300/302 $(M+H)^+$.

EXAMPLE 51G

N-benzyl-N-[(2S,3R)-2-(chloromethyl)-1-(6-chloro-3-pyridinyl)pyrrolidinyl]amine hydrochloride The product from Example 51F (0.25 g, 0.83 mmol) in 1,2-dichloroethane (10 mL) was treated with 1-chloroethyl chloroformate (ACE-Cl; 0.13 g, 0.91 mmol; Aldrich) at ambient temperature. After stirring for 30 minutes, the mixture was concentrated and the residue was stirred with methanol for 16 hours and the solvent removed to provide the title compound (0.34 g, 100%). MS (DCI/$NH_3$) m/z 336/338/340 $(M+H)^+$.

EXAMPLE 51H (2S,3R)-2-(chloromethyl)-1-(3-pyridinyl)pyrrolidinylamine dihydrochloride The product from Example 51G (0.15 g, 0.44 mmol) in ethanol (10 mL) was treated with 10% Pd/C (0.10 g) under $H_2$ (1 atm) at 50° C. for 16 hours. The mixture was cooled, and the catalyst removed by filtration through diatomaceous earth with an ethanol rinse (2×10 mL). The filtrate was concentrated under reduced pressure and the brown residue was dissolved in isopropanol (5 mL) and treated with HCl (1 mL, 4M in 1,4-dioxane). The crystals were collected and recrystallized from isopropyl alcohol/isopropyl acetate to provide the title compound (0.070 g, 56%). $^1$H NMR ($CD_3OD$, 300 MHz) δ 2.40 (m, 1H), 2.80 (m, 1H), 3.04 (dd, J=14, 10 Hz, 1H), 3.20 (dd, J=14, 4 Hz, 1H), 3.64 (m, 2H), 3.79 (t, J=10 Hz, 1H), 4.35 (dd, J=10, 4 Hz, 1H), 7.90 (m, 2H), 8.18 (d, J=5 Hz, 1H), 8.34 (d, J=2 Hz, 1H); MS (CI/$NH_3$) m/z 212/214 $(M+H)^+$; Anal. Calcd for $C_{10}H_{13}N_3 \cdot 2HCl \cdot (0.5\ H_2O)$: C, 40.91; H, 5.84. Found: C, 40.95; H, 5.85.

The foregoing description is merely illustrative and is not intended to limit the invention to the disclosed compounds. Variations and changes which are obvious to one skilled in the art of organic and/or medicinal chemistry are to be within the scope and nature of the invention which are defined in the appended claims.

We claim:
1. A compound of formula I

$$Z\text{—}R_3 \qquad \qquad I,$$

or pharmaceutically acceptable salts thereof wherein,

Z is selected from the group consisting of

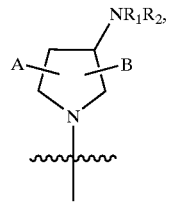

$R_1$ and $R_2$ are independently selected from the group consisting of hydrogen and alkyl;

A and B are independently absent or independently selected from the group consisting of alkenyl, alkoxy, alkoxycarbonyl, alkyl, alkynyl, carboxy, haloalkyl, halogen, hydroxy, and hydroxyalkyl;

$R_3$ is selected from the group consisting of

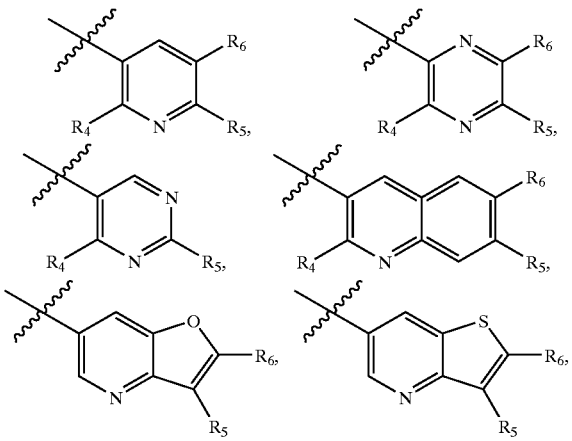

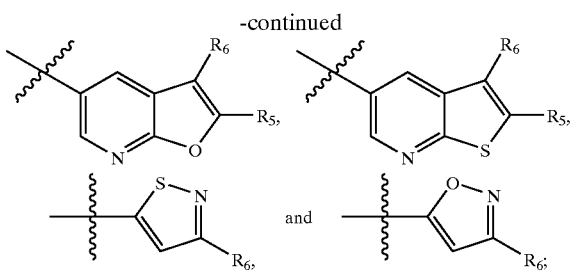

R₄ is selected from the group consisting of hydrogen, alkyl, and halogen;

R₅ is selected from the group consisting of hydrogen, alkoxy, alkyl, halogen, nitro, and —NR₁₀R₁₁ wherein R₁₀ and R₁₁ are independently selected from the group consisting of hydrogen and lower alkyl;

R₆ is selected from the group consisting of hydrogen, alkenyl, alkoxy, alkoxyalkoxy, alkoxyalkyl, alkoxycarbonyl, alkoxycarbonylalkyl, alkyl, alkylcarbonyl, alkylcarbonyloxy, alkylthio, alkynyl, amino, aminoalkyl, aminocarbonyl, aminocarbonylalkyl, aminosulfonyl, carboxy, carboxyalkyl, cyano, cyanoalkyl, formyl, formylalkyl, haloalkoxy, haloalkyl, halogen, hydroxy, hydroxyalkyl, mercapto, mercaptoalkyl, nitro, 5-tetrazolyl, —NR₇SO₂R₈, —C(NR₇)NR₈R₉, —CH₂C(NR₇)NR₈R₉, —C(NOR₇)R₈, —C(NCN)R₇, —C(NNR₇R₈)R₉, —S(O)₂OR₇, and —S(O)₂R₇; and R₇, R₈, and R₉ are independently selected from the group consisting of hydrogen and alkyl.

2. A compound according to claim 1 wherein R₃ is

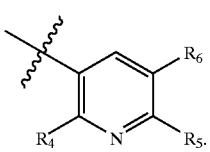

3. A compound according to claim 2 selected from the group consisting of
N-[(3S)-1-(6-chloro-3-pyridinyl)pyrrolidinyl]-N-methylamine;
(3S)-1-(6-chloro-3-pyridinyl)pyrrolidinylamine;
N-[(3S)-1-(6-chloro-3-pyridinyl)pyrrolidinyl]-N,N-dimethylamine;
(3R)-1-(6-chloro-3-pyridinyl)pyrrolidinylamine;
N-[(3R)-1-(6-chloro-3-pyridinyl)pyrrolidinyl]-N-methylamine;
N-[(3R)-1-(6-chloro-3-pyridinyl)pyrrolidinyl]-N,N-dimethylamine;
1-(6-chloro-3-pyridinyl)-3-pyrrolidinylamine;
(3S)-1-(3-pyridinyl)pyrrolidinylamine;
N-methyl-N-[(3S)-1-(3-pyridinyl)pyrrolidinyl]amine;
1-(3-pyridinyl)-3-pyrrolidinylamine;
(3R)-1-[5-(trifluoromethyl)-3-pyridinyl]pyrrolidinylamine;
N-methyl-N-{(3R)-1-[5-(trifluoromethyl)-3-pyridinyl]pyrrolidinyl}amine;
(3S)-1-[5-(trifluoromethyl)-3-pyridinyl]pyrrolidinylamine;
N-methyl-N-{(3S)-1-[5-(trifluoromethyl)-3-pyridinyl]pyrrolidinyl}amine;
(3R)-1-(6-chloro-5-methyl-3-pyridinyl)pyrrolidinylamine;
N-[(3R)-1-(6-chloro-5-methyl-3-pyridinyl)pyrrolidinyl]-N-methylamine;
(3S)-1-(6-chloro-5-methyl-3-pyridinyl)pyrrolidinylamine;
N-[(3S)-1-(6-chloro-5-methyl-3-pyridinyl)pyrrolidinyl]-N-methylamine;
(3S)-1-(5,6-dichloro-3-pyridinyl)pyrrolidinylamine;
N-[(3S)-1-(5,6-dichloro-3-pyridinyl)pyrrolidinyl]-N-methylamine;
(3R)-1-(5,6-dichloro-3-pyridinyl)pyrrolidinylamine;
N-[(3R)-1-(5,6-dichloro-3-pyridinyl)pyrrolidinyl]-N-methylamine;
(3S)-1-(6-chloro-5-methoxy-3-pyridinyl)pyrrolidinylamine;
N-[(3S)-1-(6-chloro-5-methoxy-3-pyridinyl)pyrrolidinyl]-N-methylamine;
(3S)-1-(6-fluoro-5-methyl-3-pyridinyl)pyrrolidinylamine;
N-[(3S)-1-(6-fluoro-5-methyl-3-pyridinyl)pyrrolidinyl]-N-methylamine;
(3R)-1-(6-fluoro-5-methyl-3-pyridinyl)pyrrolidinylamine;
N-[(3R)-1-(6-fluoro-5-methyl-3-pyridinyl)pyrrolidinyl]N-methylamine;
(3S)-1-(5-nitro-3-pyridinyl)pyrrolidinylamine;
N-methyl-N-[(3S)-1-(5-nitro-3-pyridinyl)pyrrolidinyl]amine;
(3R)-1-(5-nitro-3-pyridinyl)pyrrolidinylamine;
N-methyl-N-[(3R)-1-(5-nitro-3-pyridinyl)pyrrolidinyl]amine; and
(2S,3R)-2-chloromethyl)-1-(3-pyridinyl)pyrrolidinylamine.

4. A compound according to claim 1 selected from the group consisting of
(3R)-1-(3-pyridinyl)pyrrolidinylamine;
N-methyl-N-[(3R)-1-(3-pyridinyl)pyrrolidinyl]amine;
(3R)-1-(6-chloro-5-methoxy-3-pyridinyl)pyrrolidinylamine;
N-[(3R)-1-(6-chloro-5-methoxy-3-pyridinyl)pyrrolidinyl]-N-methylamine;
(3S)-1-(5-methoxy-3-pyridinyl)pyrrolidinylamine;
N-[(3S)-1-(5-methoxy-3-pyridinyl)pyrrolidinyl]-N-methylamine;
(3R)-1-(5-methoxy-3-pyridinyl)pyrrolidinylamine;
N-[(3R)-1-(5-methoxy-3-pyridinyl)pyrrolidinyl]-N-methylamine;
(3S)-1-(6-bromo-3-pyridinyl)pyrrolidinylamine;
N-[(3S)-1-(6-bromo-3-pyridinyl)pyrrolidinyl]-N-methylamine;
(3R)-1-(6-bromo-3-pyridinyl)pyrrolidinylamine;
N-[(3R)-1-(6-bromo-3-pyridinyl)pyrrolidinyl]-N-methylamine;
(3S)-1-(5-fluoro-3-pyridinyl)pyrrolidinylamine;
N-[(3S)-1-(S-fluoro-3-pyridinyl)pyrrolidinyl]-N-methylamine;
(3Rd 1-(S-fluoro-3-pyridinyl)pyrrolidinylamine;
N-[(3R)-1-(5-fluoro-3-pyridinyl)pyrrolidinyl]-N-methylamine;
(3S)-1-(6-chloro-5-fluoro-3-pyridinyl)pyrrolidinylamine;
N-[(3S)-1-(6-chloro-5-fluoro-3-pyridinyl)pyrrolidinyl]-N-methylamine;
(3R)-1-(6-chloro-5-fluoro-3-pyridinyl)pyrrolidinylamine;
N-[(3R)-1-(6-chloro-5-fluoro-3-pyridinyl)pyrrolidinyl]-N-methylamine;
(3S)-1-(6-bromo-5-fluoro-3-pyridinyl)pyrrolidinylamine;
N-[(3S)-1-(6-bromo-5-fluoro-3-pyridinyl)pyrrolidinyl]-N-methylamine;
(3R)-1-(6-bromo-5-fluoro-3-pyridinyl)pyrrolidinylamine;
N-[(3R)-1-(6-bromo-5-fluoro-3-pyridinyl)pyrrolidinyl]-N-methylamine;
(3S)-1-(5-bromo-6-chloro-3-pyridinyl)pyrrolidinylamine;
N-[(3S)-1-(5-bromo-6-chloro-3-pyridinyl)pyrrolidinyl]-N-methylamine;

(3R)-1-(5-bromo-6-chloro-3-pyridinyl)pyrrolidinylamine;
N-[(3R)-1-(5-bromo-6-chloro-3-pyridinyl)pyrrolidinyl]-N-methylamine;
(3S)-1-(6-bromo-5-chloro-3-pyridinyl)pyrrolidinylamine;
N-[(3S)-1-(6-bromo-5-chloro-3-pyridinyl)pyrrolidinyl]-N-methylamine;
(3R)-1-(6-bromo-5-chloro-3-pyridinyl)pyrrolidinylamine;
N-[(3R)-1-(6-bromo-5-chloro-3-pyridinyl)pyrrolidinyl]-N-methylamine;
(3S)-1-(6-bromo-5-ethoxy-3-pyridinyl)pyrrolidinylamine;
N-[(3S)-1-(6-bromo-5-ethoxy-3-pyridinyl)pyrrolidinyl]-N-methylamine;
(3R)-1-(6-bromo-5-ethoxy-3-pyridinyl)pyrrolidinylamine;
N-[(3R)-1-(6-bromo-5-ethoxy-3-pyridinyl)pyrrolidinyl]-N-methylamine;
(3S)-1-(5-cyano-3-pyridinyl)pyrrolidinylamine;
N-[(3S)-1-(5-cyano-3-pyridinyl)pyrrolidinyl]-N-methylamine;
(3R)-1-(5-cyano-3-pyridinyl)pyrrolidinylamine;
N-[(3R)-1-(5-cyano-3-pyridinyl)pyrrolidinyl]-N-methylamine;
(3S)-1-(5-ethynyl-3-pyridinyl)pyrrolidinylamine;
N-[(3S)-1-(5-ethynyl-3-pyridinyl)pyrrolidinyl]-N-methylamine;
(3R)-1-(5-ethynyl-3-pyridinyl)pyrrolidinylamine;
N-[(3R)-1-(5-ethynyl-3-pyridinyl)pyrrolidinyl]-N-methylamine;
(3S)-1-furo[3,2-b]pyridin-6-ylpyrrolidinylamine;
N-[(3S)-1-furo[3,2-b]pyridin-6-ylpyrrolidinyl]-N-methylamine;
(3R)-1-furo[3,2-b]pyridin-6-ylpyrrolidinylamine;
N-[(3R)-1-furo[3,2-b]pyridin-6-ylpyrrolidinyl]-N-methylamine;
1-(6-chloro-3-pyridinyl)-3-methyl-3-pyrrolidinylamine;
N-[1-(6-chloro-3-pyridinyl)-3-methyl-3-pyrrolidinyl]-N-methylamine;
1-(3-pyridinyl)-3-methyl-3-pyrrolidinylamine; and
N-[1-(3-pyridinyl)-3-methyl-3-pyrrolidinyl]-N-methylamine.

5. A pharmaceutical composition comprising a therapeutically effective amount of a compound of claim 1 in combination with a pharmaceutically acceptable carrier.

6. A method of treating a disorder wherein the disorder is selected from the group consisting of Alzheimer's disease, Parkinson's disease, attention deficit hyperactivity disorder, depression, nicotinic withdrawal syndrome, pain, Tourette's syndrome, and schizophrenia in a host mammal in need of such treatment comprising administering a therapeutically effective amount of a compound of claim 1.

7. The method according to claim 6 wherein the disorder is pain.

* * * * *

UNITED STATES PATENT AND TRADEMARK OFFICE
CERTIFICATE OF CORRECTION

PATENT NO.   : 6,833,370 B1
DATED        : December 21, 2004
INVENTOR(S)  : Michael R. Schrimpf et al.

It is certified that error appears in the above-identified patent and that said Letters Patent is hereby corrected as shown below:

Column 66,
Line 48, replace "N-[(3S)-1-(S-fluoro-3-pyridinyl)" with -- N-[(3S)-1-(5-fluoro-3-pyridinyl) --.
Line 50, replace "(3Rd 1-(S-fluoro-3-pyridinyl)" with
-- (3R)-1-(5-fluoro-3-pyridinyl) --.

Signed and Sealed this

Fourteenth Day of February, 2006

JON W. DUDAS
*Director of the United States Patent and Trademark Office*